United States Patent
Matula, Jr. et al.

(10) Patent No.: US 8,118,027 B2
(45) Date of Patent: Feb. 21, 2012

(54) PATIENT INTREFACE ASSEMBLY SUPPORTED UNDER THE MANDIBLE

(75) Inventors: Jerome Matula, Jr., Apollo, PA (US); Peter Chi Fai Ho, Pittsburgh, PA (US); Jason P. Eaton, Hunker, PA (US); Elias G. Diacopoulos, Export, PA (US); Steven B. Radney, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1284 days.

(21) Appl. No.: 11/516,880

(22) Filed: Sep. 7, 2006

(65) Prior Publication Data

US 2007/0000495 A1 Jan. 4, 2007

Related U.S. Application Data

(63) Continuation of application No. 11/048,680, filed on Feb. 1, 2005, now Pat. No. 7,178,525.

(60) Provisional application No. 60/542,750, filed on Feb. 6, 2004.

(51) Int. Cl.
*A62B 18/02* (2006.01)
*A61M 16/00* (2006.01)

(52) U.S. Cl. ......... 128/206.21; 128/207.13; 128/204.18; 128/205.25

(58) Field of Classification Search ............. 128/204.18, 128/206.18, 206.21, 206.28, 207.11, 207.13, 128/207.18
See application file for complete search history.

(56) References Cited

U.S. PATENT DOCUMENTS

| | | |
|---|---|---|
| 2,241,535 A | 5/1941 | Boothby et al. |
| 4,437,462 A | 3/1984 | Piljay et al. |
| 4,671,271 A | 6/1987 | Bishop et al. |
| 4,677,977 A | 7/1987 | Wilcox |
| 4,782,832 A | 11/1988 | Trimble et al. |
| 4,827,923 A | 5/1989 | Bishop et al. |
| 4,944,310 A | 7/1990 | Sullivan |
| 5,269,296 A | 12/1993 | Landis |
| 5,295,480 A | 3/1994 | Zemo |
| 5,437,273 A | 8/1995 | Bates et al. |
| 5,560,354 A | 10/1996 | Berthon-Jones et al. |
| 5,687,713 A | 11/1997 | Bahr et al. |

(Continued)

FOREIGN PATENT DOCUMENTS

EP 0 549 299 B1 3/2002

OTHER PUBLICATIONS

"CPAP Mask Options", APNEWS, pp. 4-5.

(Continued)

*Primary Examiner* — Justine Yu
*Assistant Examiner* — Rachel Young
(74) *Attorney, Agent, or Firm* — Michael W. Haas

(57) ABSTRACT

A patient interface assembly that includes a substantially rigid support and a patient interface device coupled to a first end of the support. A first arm is coupled to a first side of the support and a second arm is coupled to a second side of the support. A cross member spans between the first arm and the second arm such that the cross member is disposed under a patient's mandible when the patient interface assembly is worn by a user. An addition, a conduit is coupled to a second end of the support.

7 Claims, 46 Drawing Sheets

U.S. PATENT DOCUMENTS

| | | | |
|---|---|---|---|
| 5,724,965 | A | 3/1998 | Handke et al. |
| 5,954,048 | A | 9/1999 | Thornton |
| 6,012,455 | A | 1/2000 | Goldstein |
| 6,016,807 | A | 1/2000 | Lodge |
| 6,119,694 | A | 9/2000 | Correa et al. |
| 6,324,701 | B1 | 12/2001 | Alexander et al. |
| 6,347,631 | B1 | 2/2002 | Hansen et al. |
| 6,418,928 | B1 * | 7/2002 | Bordewick et al. ...... 128/205.25 |
| 6,431,172 | B1 | 8/2002 | Bordewick |
| 6,470,886 | B1 | 10/2002 | Jestrabek-Hart |
| 6,526,978 | B2 * | 3/2003 | Dominguez ............. 128/207.14 |
| 6,860,268 | B2 | 3/2005 | Bohn et al. |
| D505,489 | S | 5/2005 | Sleeper |
| 6,889,689 | B1 | 5/2005 | Neuman |
| 6,926,004 | B2 | 8/2005 | Schumacher |
| 7,047,971 | B2 | 5/2006 | Ho et al. |
| 7,225,811 | B2 * | 6/2007 | Ruiz et al. ................. 128/207.11 |
| 2002/0189614 | A1 * | 12/2002 | Dominguez ............. 128/200.26 |
| 2003/0145859 | A1 | 8/2003 | Bohn et al. |
| 2004/0083534 | A1 | 5/2004 | Ruiz et al. |

OTHER PUBLICATIONS

Blitzer, "Directory of Sources for Ventilation Face Masks", International Ventilator Users Network, pp. 1-12, Gazette International Networking Institute.
Vital Signs, Inc., Mask brochure.
Vacu Med, "Full Face Mask for CPAP and BiPAP™".
Viasys™ Healthcare, "Spiritus™ Respiratory System The Breath of Life", www.viasyshealthcare.com/Products/Spiritus/Spiritus.asp.
Innomed Technologies, Inc., "InnoMed's Nasal-Aire® C.P.A.P. Interface", www.innomedinc.com.
Sullivan, "Nasal Cannulas Gain Traction", www.hmenews.com/2003.01/depts/vendors/vendors2.htm.

* cited by examiner

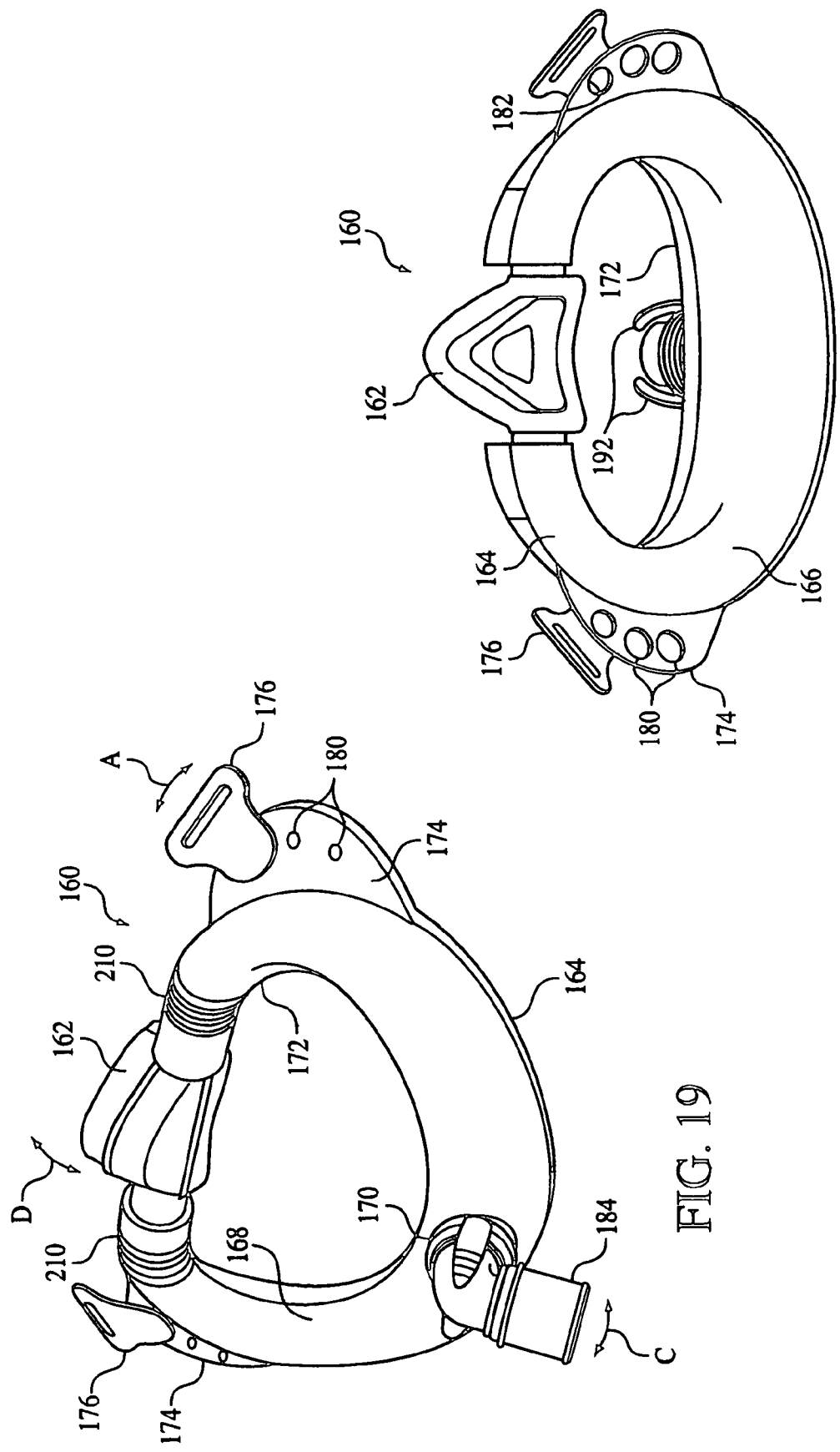

PATIENT INTREFACE ASSEMBLY SUPPORTED UNDER THE MANDIBLE

CROSS-REFERENCE TO RELATED APPLICATIONS

This application is a Continuation of U.S. patent application Ser. No. 11/048,680 filed Feb. 1, 2005, which claims priority under 35 U.S.C. §119(e) from provisional U.S. patent application No. 60/542,750 filed Feb. 6, 2004, the contents of which are incorporated herein by reference.

BACKGROUND OF THE INVENTION

1. Field of the Invention

The present invention generally relates to a patient interface assembly for use in a pressure support system, and, in particular, to a patient interface assembly that is supported under at least a portion of the patient's mandible, and to a gas delivery system that incorporates such a patient interface assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask having a rigid frame supporting a mask cushion, on the face of a patient to interface the ventilator or pressure support device with the airway of the patient so that a flow of breathing gas can be delivered from the pressure/flow generating device to the airway of the patient. It is known to maintain such masks on the face of a patient by a headgear situated on top of the patient's head having upper and lower straps, each having opposite ends threaded through connecting elements provided on the opposite sides and top of a mask.

Because such masks are typically worn for an extended period of time, it is important the headgear maintain the mask in a tight enough seal against a patient's face without discomfort. For example, in providing CPAP to treat OSA, the patient normally wears the patient interface device all night long while he or she sleeps. One concern in such a situation is that the patient interface device be supported on the user in a stable fashion so that the mask does not shift on the patient as he or she moves during sleep. Another concern is that the user does not perceive the mask to be suffocating, i.e., minimize any claustrophobic effects the user may perceive. If these concerns are not addressed, the patient may avoid wearing the interface device, defeating the purpose of the prescribed pressure support therapy. It is also important that the interface device provide a tight enough seal against a patient's face without discomfort.

U.S. Pat. No. 2,241,535 shows an apparatus for delivering breathing gas to a patient including a nose piece having two tubes extending from lower corners of the nose piece on either side of the patient's mouth and joining together in a transverse tubular member directly resting on the anterior portion of the patient's chin. The transverse tubular member rests on or above the anterior portion of the mandible. The term "mental protuberance" is used to describe the protrusion of the anterior portion of the mandible that constitutes the chin. While this term refers to a part of a bone, it is used herein to define the entire structure of bone and overlaying skin. Thus, the device taught by the '535 patent rests just above the mental protuberance.

While the mask assembly shown in the '535 patent addresses some of the above concerns, for example, by avoiding placing portions of the interface near the patient's eyes, it does not provide a stable platform that supports the nose piece. Thus, a need still exists for a mask that more completely addresses these concerns.

SUMMARY OF THE INVENTION

An exemplary embodiment of the present invention comprises a patient interface assembly and a system and method for supplying a flow of gas to a patient that incorporates such a patient interface assembly.

The patient interface assembly according to the present invention includes a substantially rigid support and a patient interface device coupled to a first end of the support. A first arm is coupled to a first side of the support and a second arm is coupled to a second side of the support. A cross member spans between the first arm and the second arm such that the cross member is disposed under a patient's mandible when the patient interface assembly is worn by a user. An addition, a conduit is coupled to a second end of the support.

These features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 19 is a front perspective view of a third embodiment of a patient interface assembly according to the principles of the present invention;

FIG. 20 is a rear view of the patient interface assembly of FIG. 19;

DETAILED DESCRIPTION OF THE EXEMPLARY EMBODIMENTS

Figure 1:
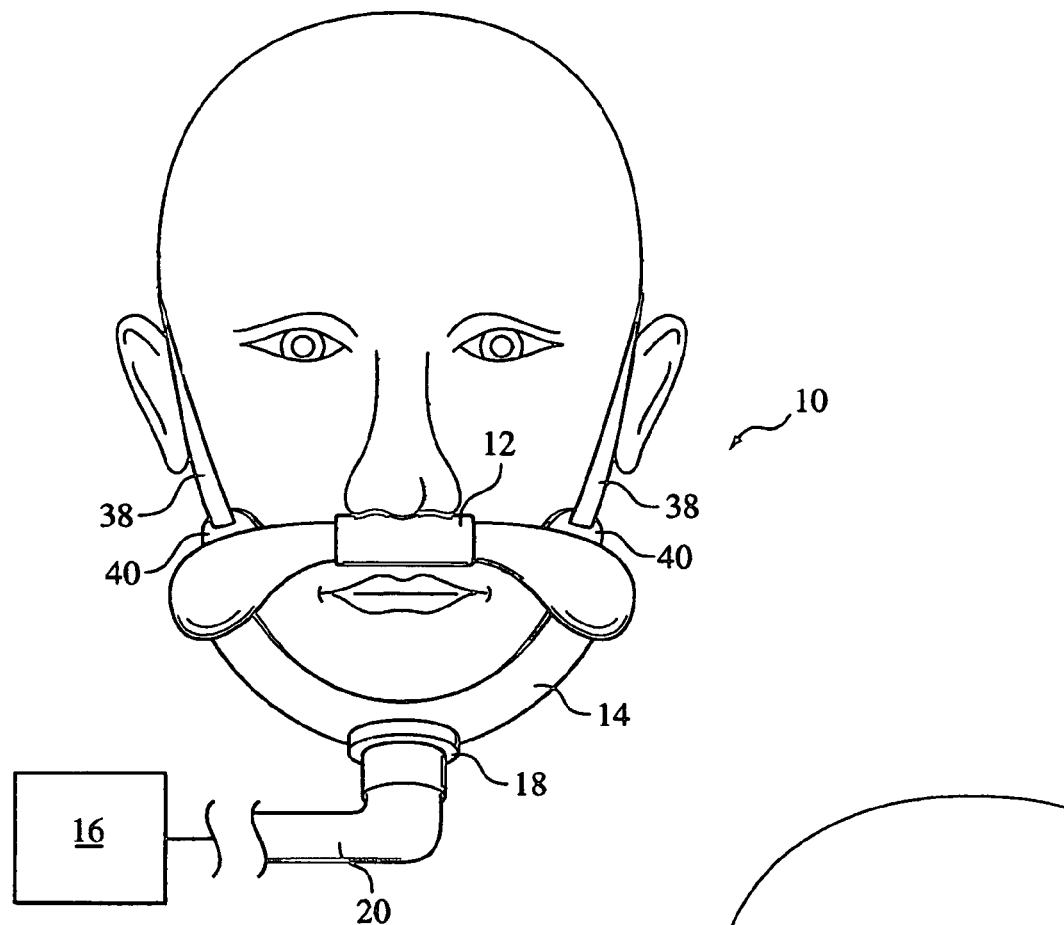
FIG. 1 is a front view of a first embodiment of a patient interface assembly and schematically illustrates a gas delivery system connected to such an interface assembly according to the principles of the present invention.
Figure 2:
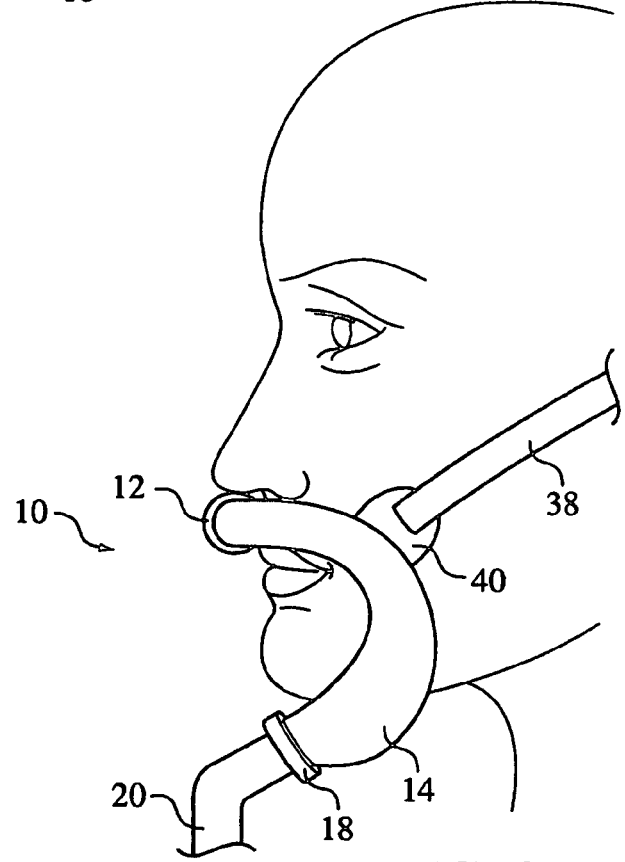
FIG. 2 is a side of the patient interface assembly of FIG. 1.

A patient interface assembly 10 according to a first embodiment of the present invention is shown in FIGS. 1-6 and includes a patient interface 12 fluidly and rotatably coupled to a chin support 14. Patient interface assembly 10 communicates a flow of breathing gas between a patient's airway and a pressure generating system 16, such as a ventilator, CPAP device, or variable pressure device, e.g. an auto-titrating device, proportional assist ventilation (PAV) device, proportional positive airway pressure (PPAP) device, C-Flex device, Bi-Flex device, or a BiPAP® device manufactured and distributed by Respironics, Inc. of Murrysville, Pa., in which the pressure provided to the patient varies with the patient's respiratory cycle so that a higher pressure is delivered during inspiration than during expiration, or other pressure support device.

Chin support 14 is preferably formed from a hollow chambered support made from a flexible plastic compound and extends from either side of patient interface 12 curving downwardly in front of the patient's cheeks around the outside of the patient's mouth to a position beneath the patient's chin. Specifically, chin support 14 extends to a position beneath or rearward the mental protuberance of the chin. Chin support 14 closely follows the contour of the patient's face and directly contacts the skin of the patient. Chin support 14 further includes a swivel port 18 located near the position beneath or rearward the mental protuberance of the chin for fluid and rotatably connection with a conduit 20, which is connected to the pressure generating device 16.

While it was noted above that the chin support can be made from a flexible plastic compound, it is to be understood that the present invention contemplates using other materials to form the chin support. That is, any semi-rigid or rigid material, whether plastic or not, can be used as the chin support. For example, chin support 14 can be formed from silicone. If necessary, the silicone can be reinforced using any conventional stiffening material to increase stiffness where needed.

Conduit 20 is typically a flexible conduit and is typically referred to as a patient circuit. The combination of the pressure generating device, the patient circuit, and the patient interface assembly, define a pressure support system that provides gas to a patient. The present invention contemplates that the pressure support system of the present invention includes any features, elements, or functions, typically present in a conventional pressure support system. For example, conduit 20 can be either a single-limb circuit or a dual-limb circuit. Accessories, such as a humidifier, pressure sensor, flow sensor, temperature sensor, humidity sensor, bacteria filter, etc. can be used in conjunction with the patient interface assembly and pressure support system of the present invention.

Patient interface 12 is fluidly and rotatably connected to chin support 14 by a rotatable coupling 22 provided on either side of patient interface 12. See FIGS. 4 and 6. In an exemplary embodiment of the present invention, rotatable coupling 22 is a two-piece relatively hard plastic device, which also provides rigidity. Rotatable coupling 22 comprises a hollow cylindrical piece 24 having a flange 26 on one end. Flange 26 is receivable within a flange receiving coupling 28 defined in patient interface 12. A rotatable flange 30 is coupled to the other end of cylindrical piece 24 and is receivable within a flange receiving coupling 32 in chin support 14. A relatively small flange 33 is provided in cylindrical piece 24 to retain rotatable flange 30 on the cylindrical piece such that they are rotatable relative to each other. In this manner, each end of chin support 14 coupled to patient interface 12 is also rotatable relative to the patient interface.

Figure 5:
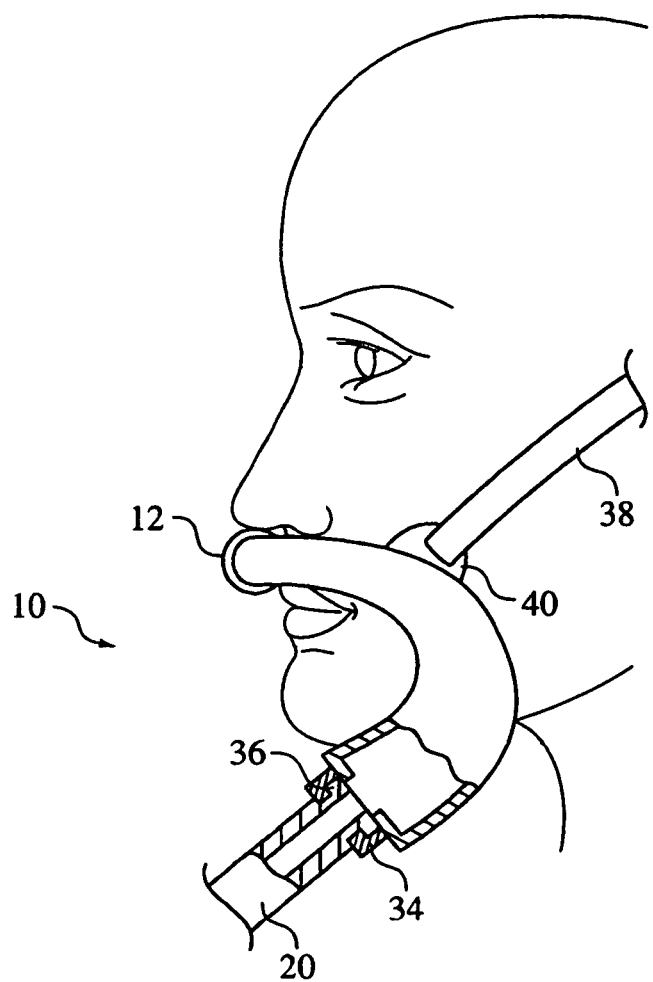
FIG. 5 is a cross-sectional view of FIG. 2.
Figure 6:
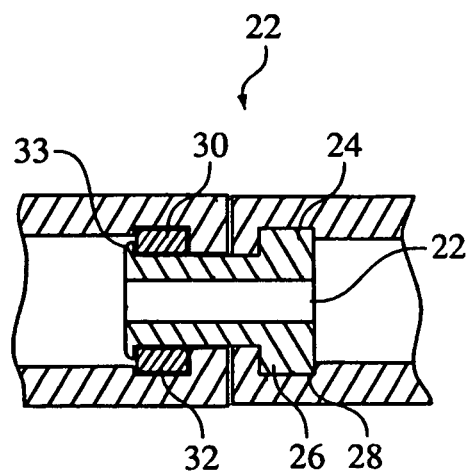
FIG. 6 is a close-up cross-sectional view of the coupling/rotation device of FIG. 4.

Swivel port 18, shown in FIG. 5, includes a flange receiving coupling 34 for receiving a flange 36 from the conduit 20 or a coupling piece for rotatable coupling between the conduit 20 and chin support 14. It is to be understood that other configurations and techniques for rotatably coupling chin support 14 to patient interface 12 and conduit 20 are contemplated by the present invention. For example, the flange and flange coupling technique used to attach chin support 14 to conduit 20 can be used in place of coupling 22 between the chin support and the patient interface, and vice versa.

The present invention also contemplates that either or both of these couplings can be non-rotatable couplings. However, in a preferred embodiment, each of these couplings are rotatable and allow the patient interface to be adjustable in discrete or an infinite number of positions relative to the chin support. An example of a coupling that provides discrete positioning of the patient interface relative to the chin support is discussed below.

Patient interface assembly 10 is held in place on the patient's head by an adjustable head strap 38, which is attachable to connection pieces 40 on chin support 14 on either side of the patient interface 12. It is to be understood that other connection pieces and other head straps can be provided in addition to or in place of those shown to secure the interface to the patient.

Figure 3:
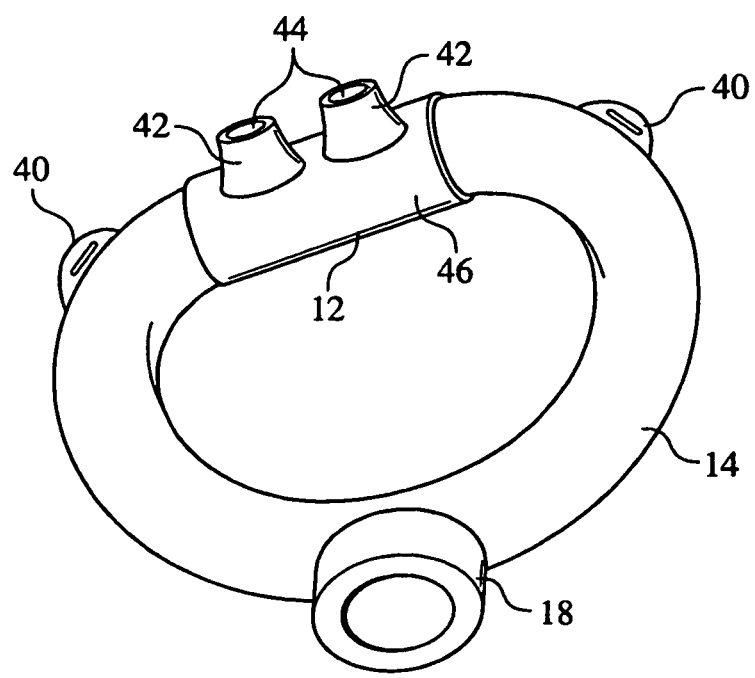
FIG. 3 is a perspective view of the patient interface assembly of FIG. 1.
Figure 4:
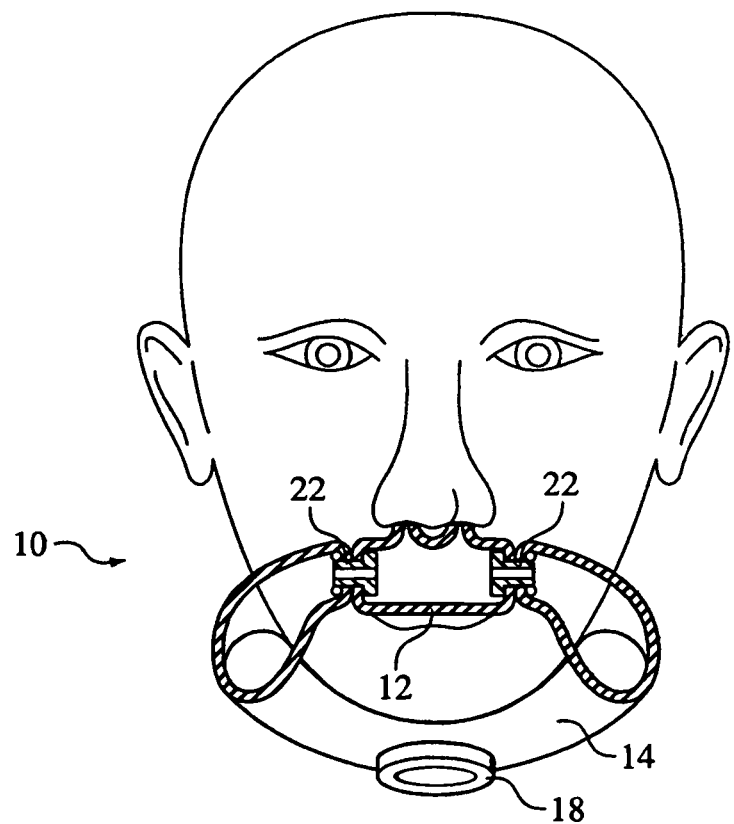
FIG. 4 is a cross-sectional view of the patient interface assembly of FIG. 1.

The modular design of patient interface assembly 10 allows a variety of patient interfaces 12 to be used to couple the patient interface assembly to the airway of the patient. Examples of other such patient interfaces include nares interfaces, nasal masks, and nasal/oral masks. FIGS. 1-6 show a nares interface being used with the patient interface assembly. In this embodiment, as best shown in FIG. 3, patient interface 12 includes a substantially cylindrical support piece 46 supporting a pair of spaced nares elements 42. Each nares element 42 has an opening 44 for communicating with the nasal passages of the patient with an interior of cylindrical support piece 46 and, hence, an interior of chin support 14. In addition, each end of the cylindrical support piece 46 includes the flange receiving coupling 28 as discussed above.

Figure 7:
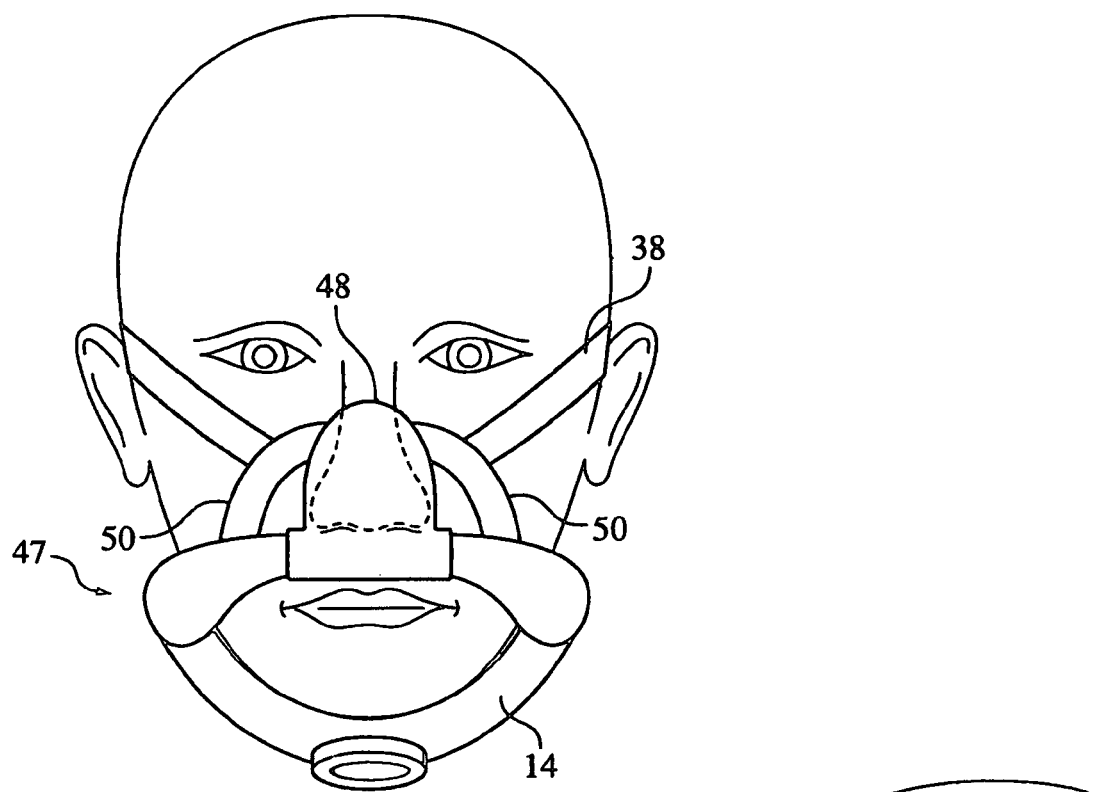
FIG. 7 is a front view of a second embodiment of a patient interface assembly according to the principles of the present invention.
Figure 8:
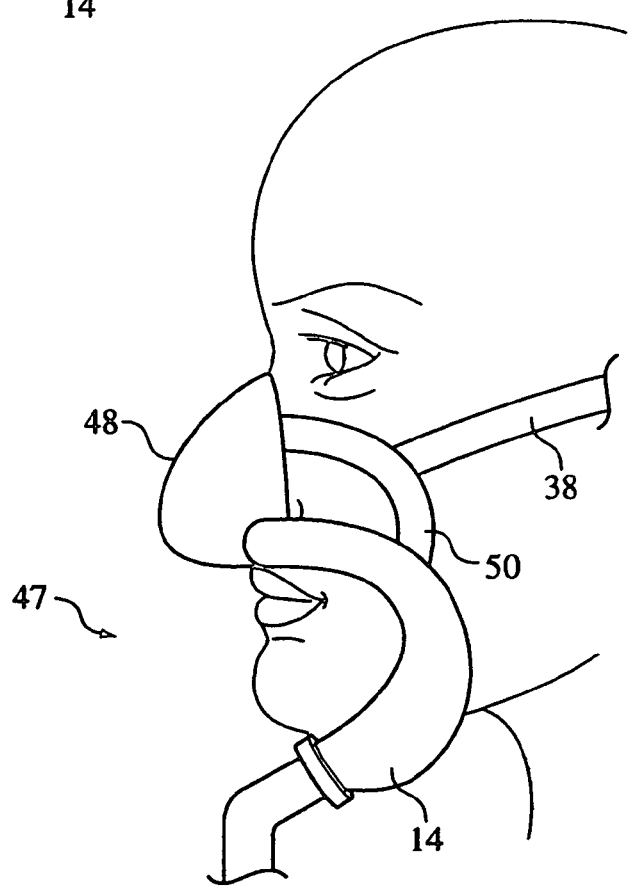
FIG. 8 is a side view of the patient interface assembly of FIG. 7.

A second embodiment of a patient interface assembly 47 is shown in FIGS. 7-8. This second embodiment is generally similar to the first embodiment except that a nasal mask 48 is used as the patient interface instead of a nares interface. Nasal mask 48 includes a shell, seal, or cushion that covers at least a portion of the nose of the patient. The lower corners of the mask are connected to chin support 14 in any conventional manner, including the rotatable coupling techniques discussed above. Head strap 38 is attached to patient interface assembly 47 using an additional attachment piece 50 connected to both chin support 14 and nasal mask 48. Preferably, the attachment pieces are pivotally or moveably connected to the chin support and the nasal mask so they can move or flex to fit comfortably on the patient. Attachment piece 50 can be either rigid, semi-rigid, or flexible.

Alternate embodiments of the patient interface suitable for use in the patient interface assembly are shown in FIGS. 9-18B. The patient interface illustrated in each of these embodiments attaches to the chin support as discussed above. For example, each patient interface embodiment includes a pair of flange receiving couplings for receiving flanges from a pair of rotatable couplings as discussed above so that each patient interface is capable of rotating relative to the chin support.

Figure 9A:
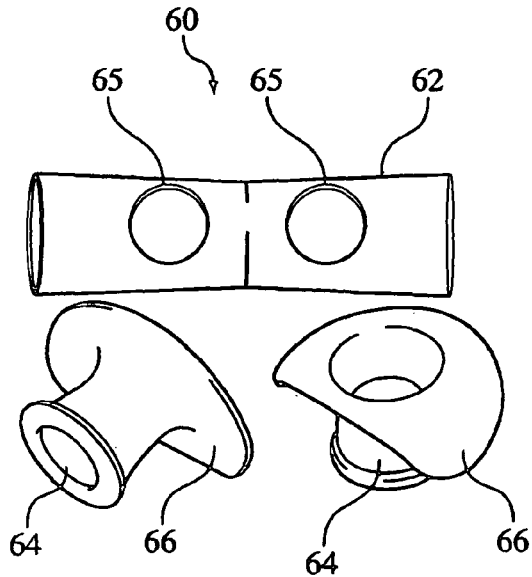
FIGS. 9A and 9B are exploded and rear views, respectively, of an exemplary embodiment of a patient interface portion of the patient interface assembly according to the principles of the present invention.
Figure 9B:
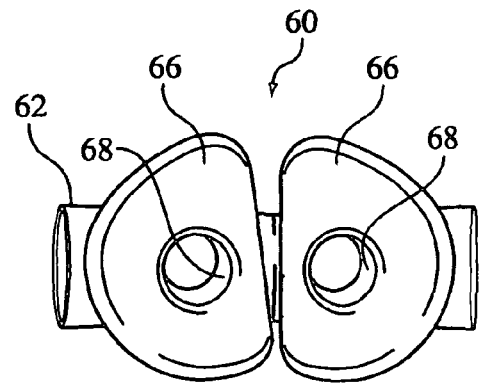

Patient interface 60 shown in FIGS. 9A and 9B includes a conduit 62 and a pair of nares pillows 64. Conduit 62 is preferably a rigid structure, made from plastic, for example, and nares pillows 64 are soft structures, made from gel, foam, silicone, or a soft rubber, for example. Nares pillows 64 are removable attached to openings 65 defined in conduit 62. For this purpose, small flanges are provided on the ends of the nares pillows that insert into the conduit.

The end of the nares pillows that contact the patient are mushroom-shaped so that the relatively large flange 66 is provided to contact the patient's nose area surrounding the nares. Flange 66 remains outside the patient. A channel 68 is defined through the nares pillows to communicate gas between the airway of the patient and the interior of the conduit.

Figure 10A:
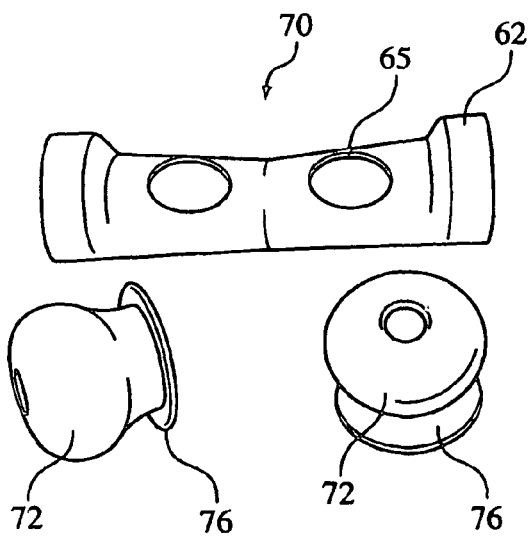
FIGS. 10A and 10B are exploded and rear views, respectively, of an exemplary embodiment of a patient interface portion of the patient interface assembly according to the principles of the present invention.
Figure 10B:
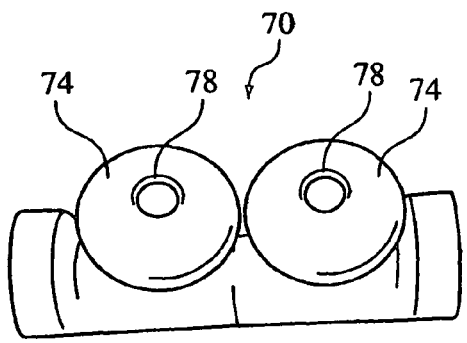

Patient interface 70 shown in FIGS. 10A and 10B uses conduit 62 but has a different configuration for a pair of nares pillows 72. Nares pillows 72 are generally balloon or bulbous-shaped so that a rounded end 74 of the nares pillows rests on the underside of the user's nose around each nare. As with the previous embodiment, a flange 76 is provided as the opposite end of each nares pillow to coupled the nares pillow to the conduit. A channel 78 is defined through the nares pillows to communicate gas between the airway of the patient and the interior of the conduit.

Figure 11A:
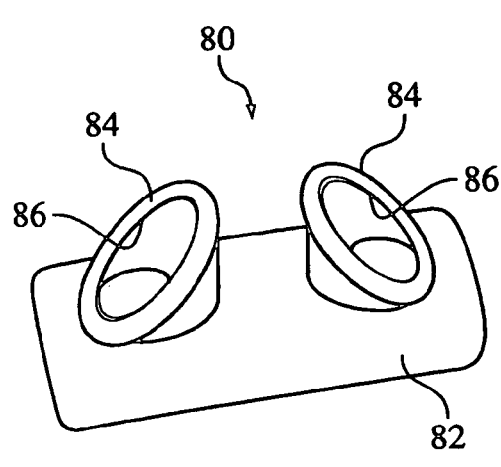
FIG. 11A is a rear view of an exemplary embodiment of a patient interface portion of the patient interface assembly according to the principles of the present invention.
Figure 11B:
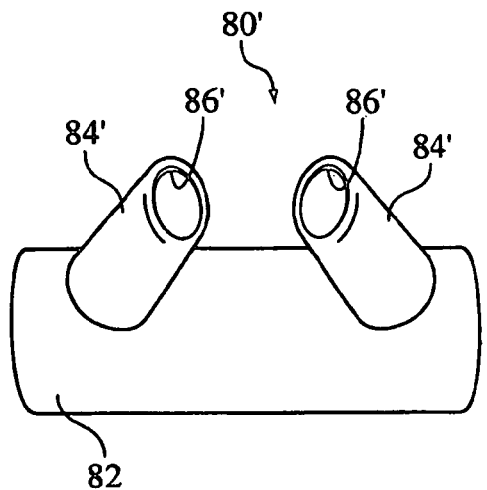
FIG. 11B is a rear view of an exemplary embodiment of a patient interface portion of the patient interface assembly according to the principles of the present invention.

Patient interface 80 shown in FIG. 11A includes a conduit 82 and a pair of prongs 84 that extend from the conduit. Prongs 84 are preferably integrally molded with conduit 82. For example, the present invention contemplates that the entire patient interface 80 is a single piece of molded silicone. Prongs 84 insert into the user's nares and extend from the conduit such that the prongs are angled toward one another. In the embodiment illustrated in FIG. 11A, each prong includes a cutout defined in the wall of the prong so that an opening 86 defined in each prong is configured like a relatively large ellipsoid. Patient interface 80' shown in FIG. 11B is configured similar to that shown in FIG. 11A, except that the walls of prongs 84' do not include such a cutout. As a result, opening 88' in prongs 84' that communicate with the interior or conduit 82' are much smaller ellipsoids and are provided mainly at the distal ends of the prongs.

Figure 12A:
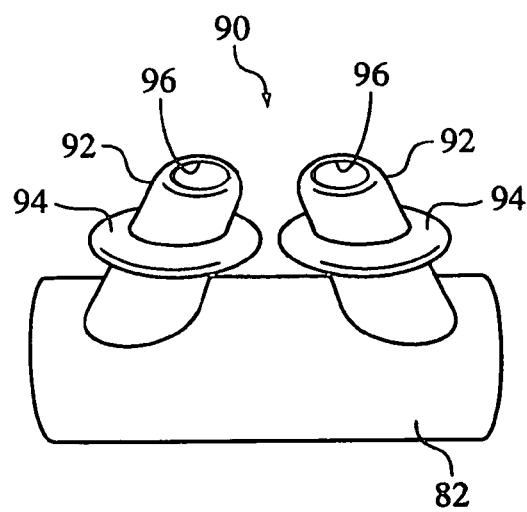
FIG. 12A is a rear view of an exemplary embodiment of a patient interface portion of the patient interface assembly according to the principles of the present invention.

Patient interfaces 90 shown in FIG. 12A is similar to that discussed above with respect to FIGS. 11A and 11B except for the configuration for the prongs. In the embodiment illustrated in FIG. 12A, each prong 92 attached to conduit 82 includes a flange 94 disposed around the perimeter of the prong at a location along the length of the prong. Flange 94 preferably is integrally molded with the prong and has a shape that is generally similar to that of the prong. The purpose of the flange is to facilitate sealing the prong against the user's nostril. An opening 96 is defined in the distal end of each prong to communicate gas with the interior of conduit 82.

Figure 12B:
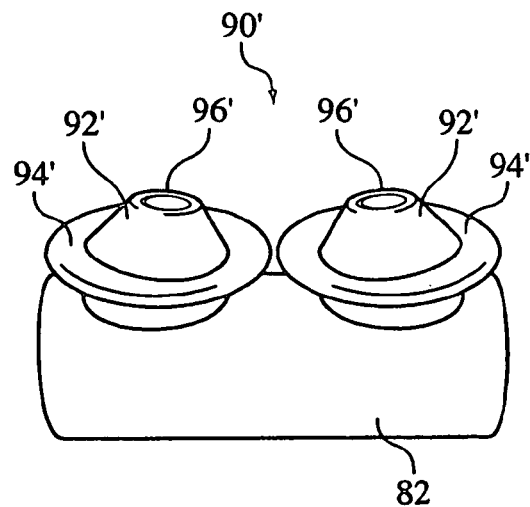
FIG. 12B is a rear view of an exemplary embodiment of a patient interface portion of the patient interface assembly according to the principles of the present invention.

Patient interface 90' shown in FIG. 12B is configured similar to that shown in FIG. 12A, except that the walls of prongs 92' are much shorter and need not be angled toward one another. In addition, flange 94' disposed on each prong is much larger than the flange in FIG. 12A, to the provide a larger sealing area.

While a single flange having a generally circular shape is shown in FIGS. 12A and 12B, it is to be understood that the present invention contemplates providing multiple flanges on each prong. The present invention also contemplates that the flanges can be shaped and sized to better match the contours of the human nostril. Indeed, the shapes of the prongs can also be contoured to better match the contours of the human nostril rather than use a standard generally cylindrical shape as shown in these figures.

Figure 13A:
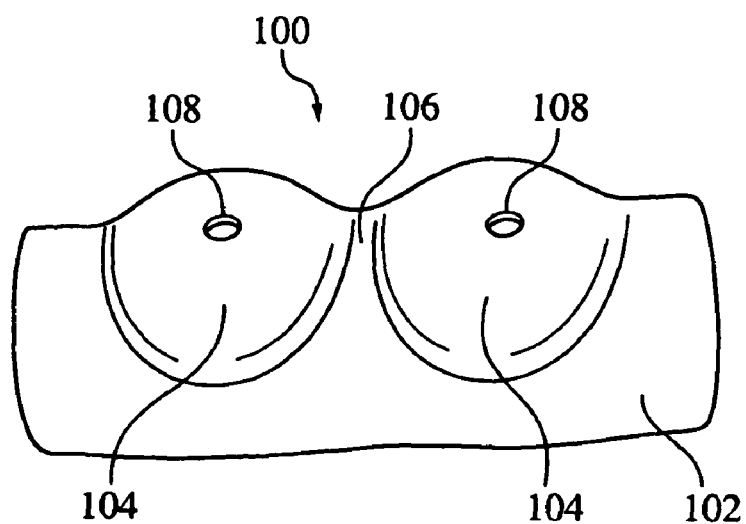
FIG. 13A is a rear view of an exemplary embodiment of a patient interface portion of the patient interface assembly according to the principles of the present invention.
Figure 13B:
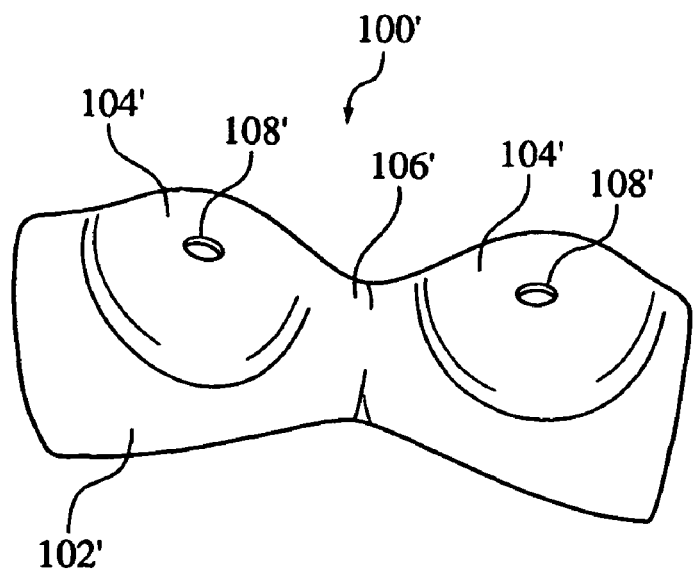
FIG. 13B is a rear view of an exemplary embodiment of a patient interface portion of the patient interface assembly according to the principles of the present invention.

FIGS. 13A and 13B illustrate patient interfaces 100 and 100', respectively, that are a type of nares pillows patient interface. Patient interface 100 includes a conduit 102. In place of a pair of nasal prongs or pillows, a pair of nostrils engaging portions 104 are formed directly into the conduit. The nostril engaging portions are a pair of bulbous regions defined in the conduit with a valley region 106 is provided between the nostrils engaging portions. The primary difference between the patient interfaces shown in FIGS. 13A and 13B reside in the depth of the valley between the bulbous regions. As in the previous embodiments, openings 108 are defined in the nostrils engaging portions 104 to communicate gas between the patient's nares and the interior of the conduit.

Figure 14A:
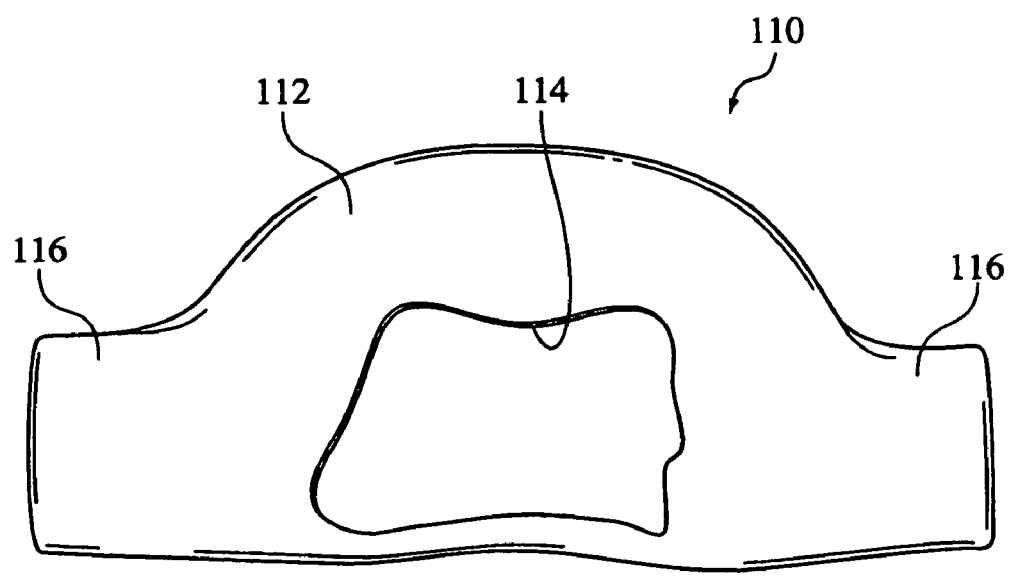
FIGS. 14A and 14B are front and rear views, respectively, of an exemplary embodiment of a patient interface portion of the patient interface assembly according to the principles of the present invention.
Figure 14B:
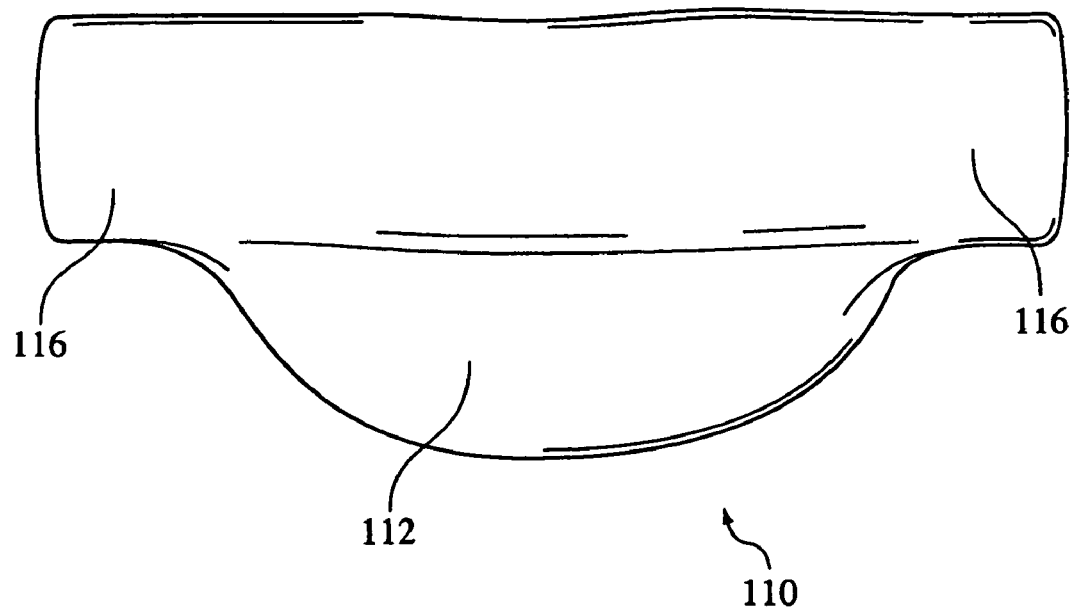

FIGS. 14A and 14B are front and rear views, respectively, of yet another patient interface 110 suitable for use with the patient interface assembly of FIG. 1. Patient interface 110 includes a flap portion 112 having an opening 114 defined therein and end portions 116 that coupled to chin support 14. The flap portion fits under the user's nose during use so that both nares are provided in opening 114. In the illustrated embodiment, opening 114 is shaped, and flap portion 112 is contoured, to generally match the underside of a human nose. This is done to improve comfort and fit. Preferably, the flap portion and the end portion are formed from a unitary material, such as silicone.

Figure 15A:
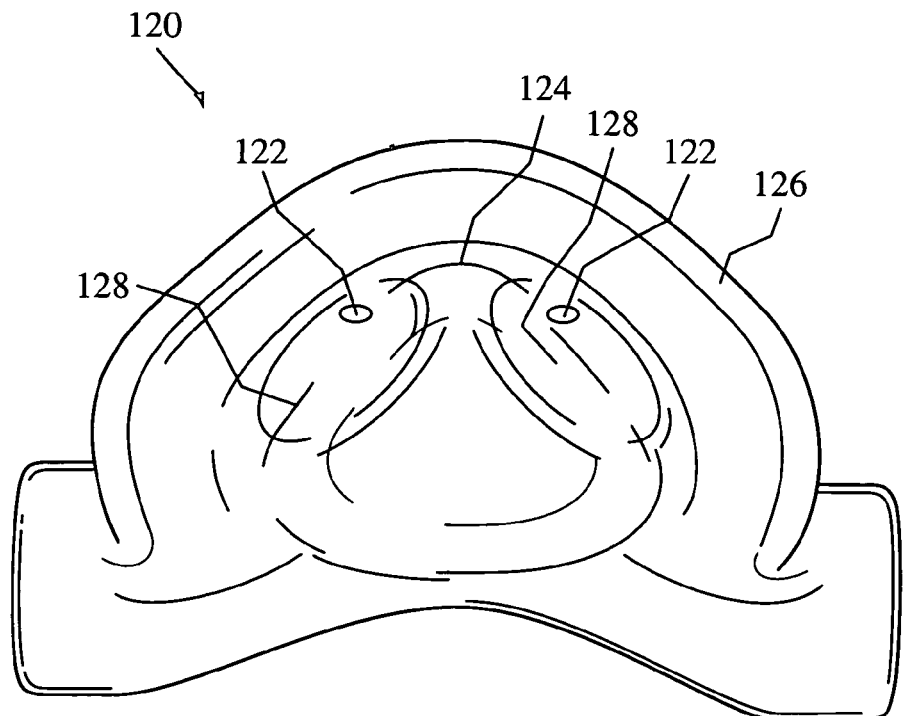
FIGS. 15A and 15B are front and rear views, respectively, of an exemplary embodiment of a patient interface portion of the patient interface assembly according to the principles of the present invention.
Figure 15B:
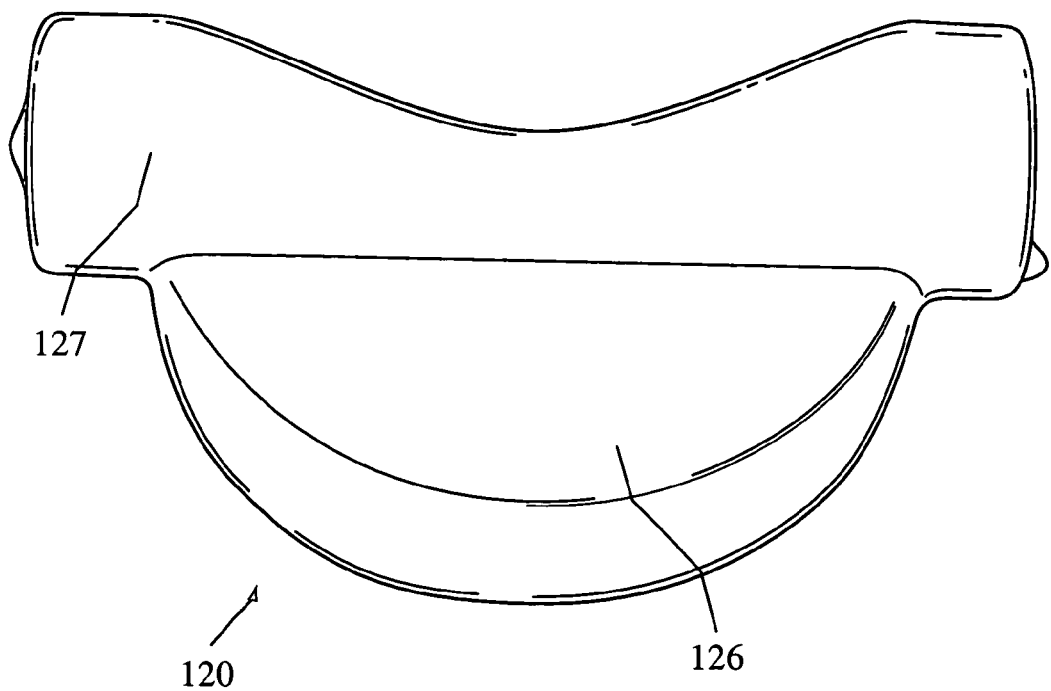

FIGS. 15A and 15B are front and rear views, respectively, of another embodiment of a patient interface 120 suitable for use with the patient interface assembly of FIG. 1. Patient interface 120 is similar to patient interface 110 in FIGS. 14A and 14B except that instead of a single, relatively large opening in which both nares are located, patient interface 120 includes a pair of openings 122 to communicate gas between the patient's nares and the interior of the patient interface. A sealing surface 124 is provided over a flap portion 126 disposed on a conduit portion 127. Openings 122 are provided in sealing surface 124. In a preferred embodiment, protrusions 128 are provided on sealing surface 124 and openings 122 are provided at an apex of the protrusions. The protrusions are shaped so as to correspond generally with a shape of a human nostril at the nares so that a good seal is formed at each nare when the patient interface is positioned at the nose. As with the previous embodiments, flap portion 126, sealing surface 124, and end portions 128, which coupled to the chin support, are preferably formed from a unitary material, such as silicone.

Figure 16A:
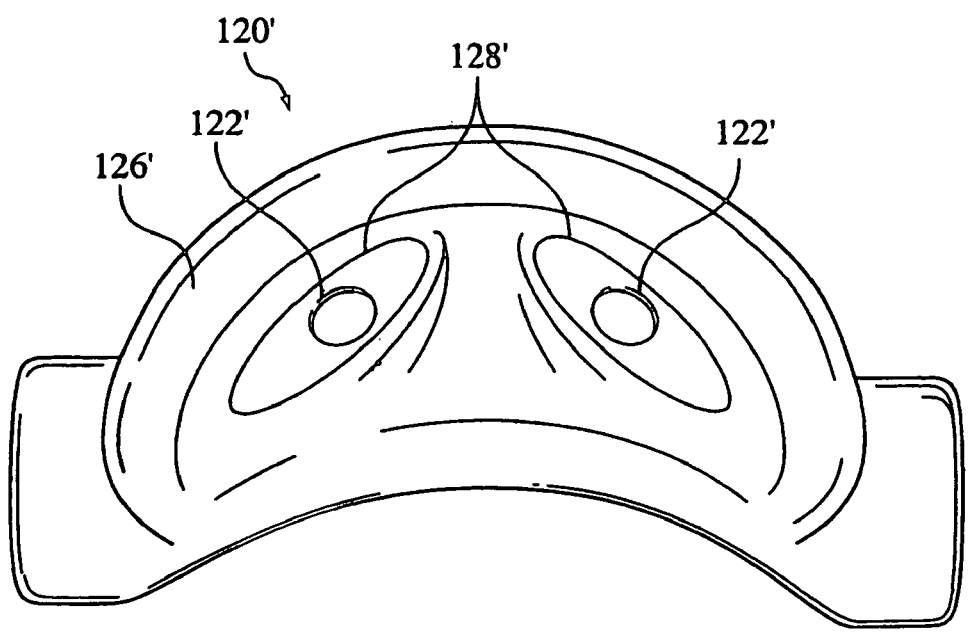
FIGS. 16A and 16B are front and rear views, respectively, of an exemplary embodiment of a patient interface portion of the patient interface assembly according to the principles of the present invention.
Figure 16B:
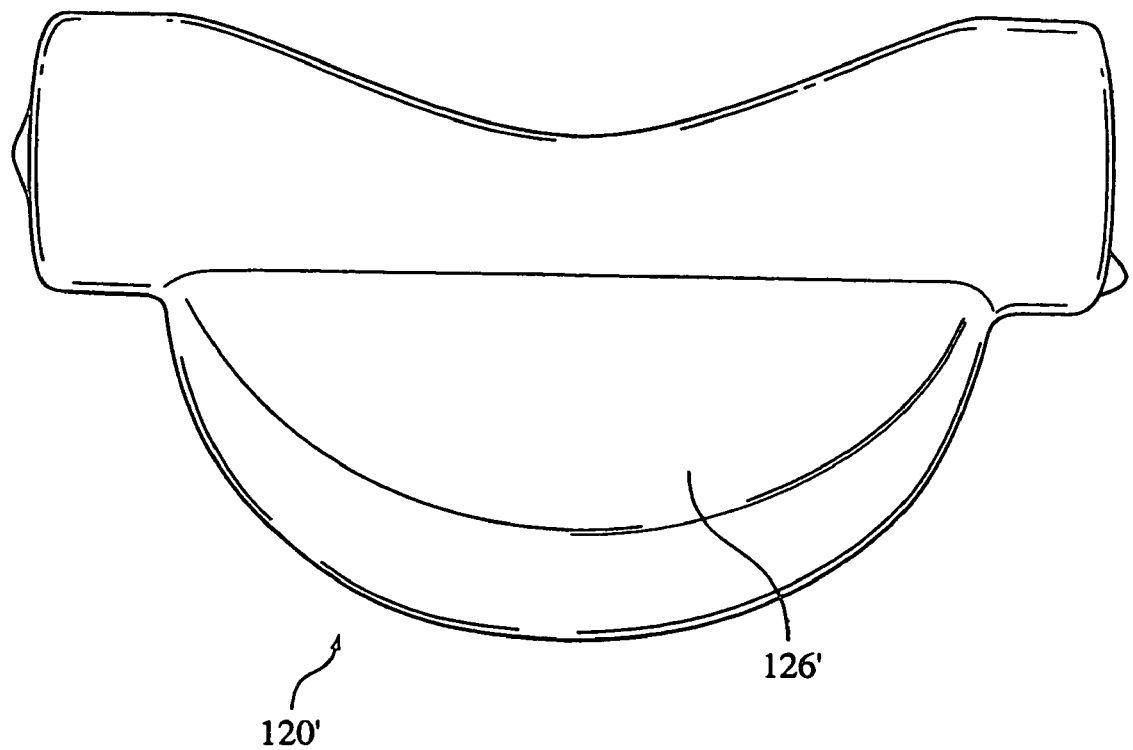

FIGS. 16A and 16B show a patient interface 120' that is similar to patient interface 120 except for the general shape and size of protrusions 128' and opening 122'. In addition, patient interface 120' lacks a flap portion (item no. 126 in FIGS. 15A and 15B) that otherwise encircles the user's nose.

Figure 17A:
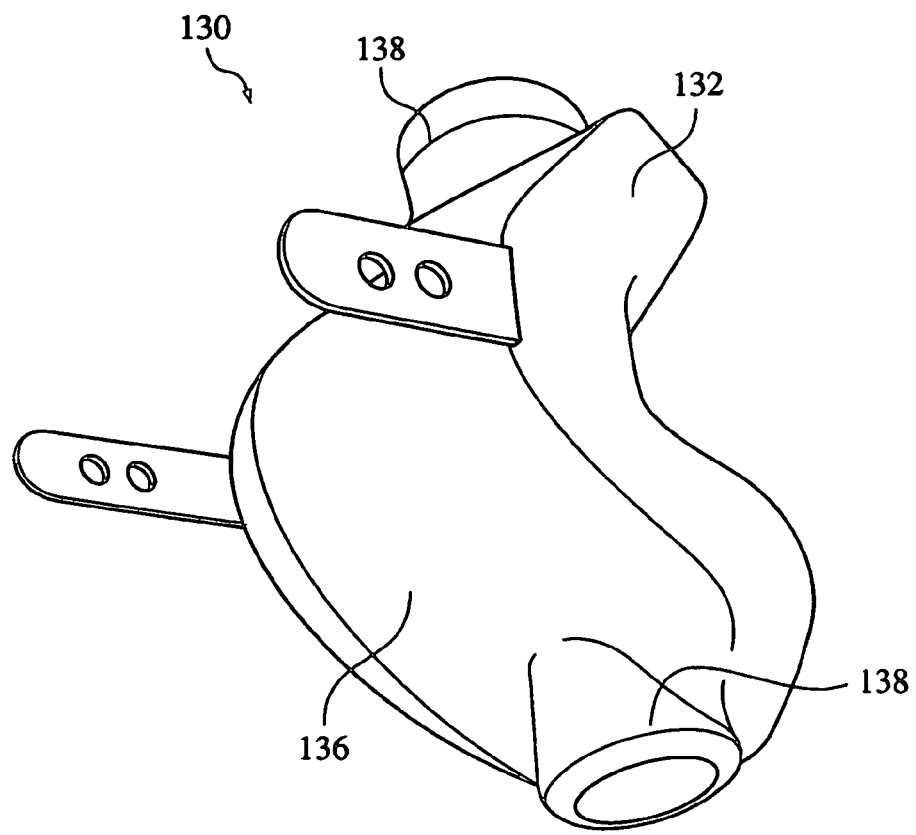
FIGS. 17A and 17B are perspective and rear views, respectively, of an exemplary embodiment of a patient interface portion of the patient interface assembly according to the principles of the present invention.
Figure 17B:
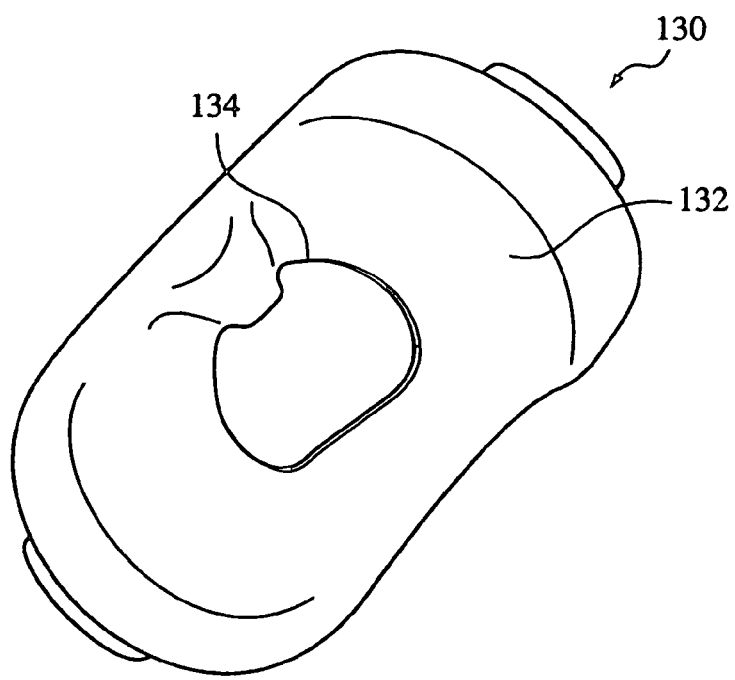

FIGS. 17A and 17B show a still further embodiment of a patient interface 130 suitable for use with the patient interface assembly of FIG. 1. Patient interface 130 is similar to the Monarch style interface manufactured by Respironics, Inc. of Murrysville, Pa., and disclosed in U.S. Pat. No. 5,724,965. Patient interface 130 includes a patient contacting portion 132, which is also referred to as a cushion or seal, that surrounds the nares. An opening 134 is provided in the cushion to communicate gas between the patient's airway and the interior of the patient interface. Patient contacting portion 132 is coupled to a support 136, which includes end portions 138 that couple the patient interface to the chin support. Patient contacting portion 132 and support 136 are angled to correspond to the underside of a patient's nose. Patient contacting portion 132 is also preferably removably coupled to support 136. It is to be understood that other variations for the patient interface, such as those taught by in U.S. Pat. No. 5,724,965, which include providing separate openings for each nostril, are contemplated by the present invention.

Figure 18A:
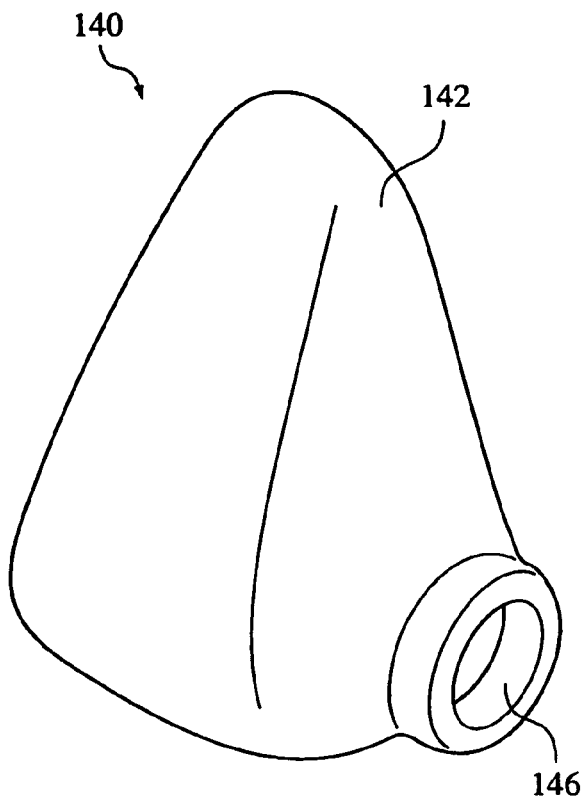
FIGS. 18A and 18B are front perspective and rear perspective views, respectively, of an exemplary embodiment of a patient interface portion of the patient interface assembly according to the principles of the present invention.
Figure 18B:
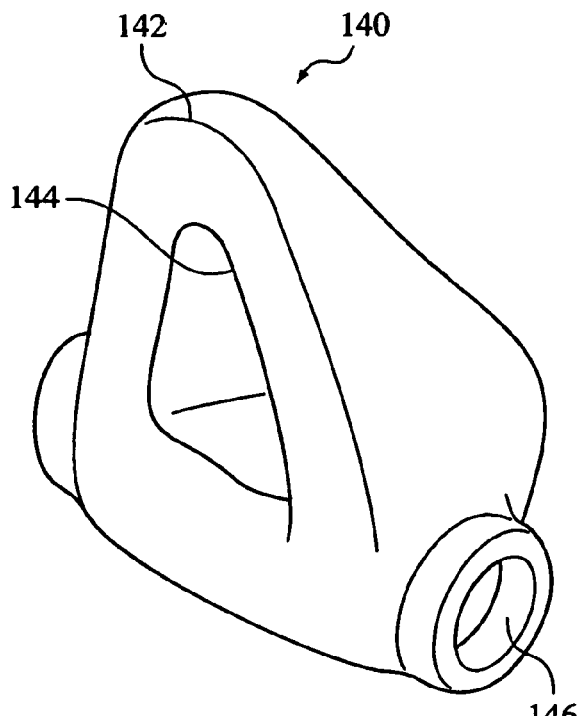
Figure 21:
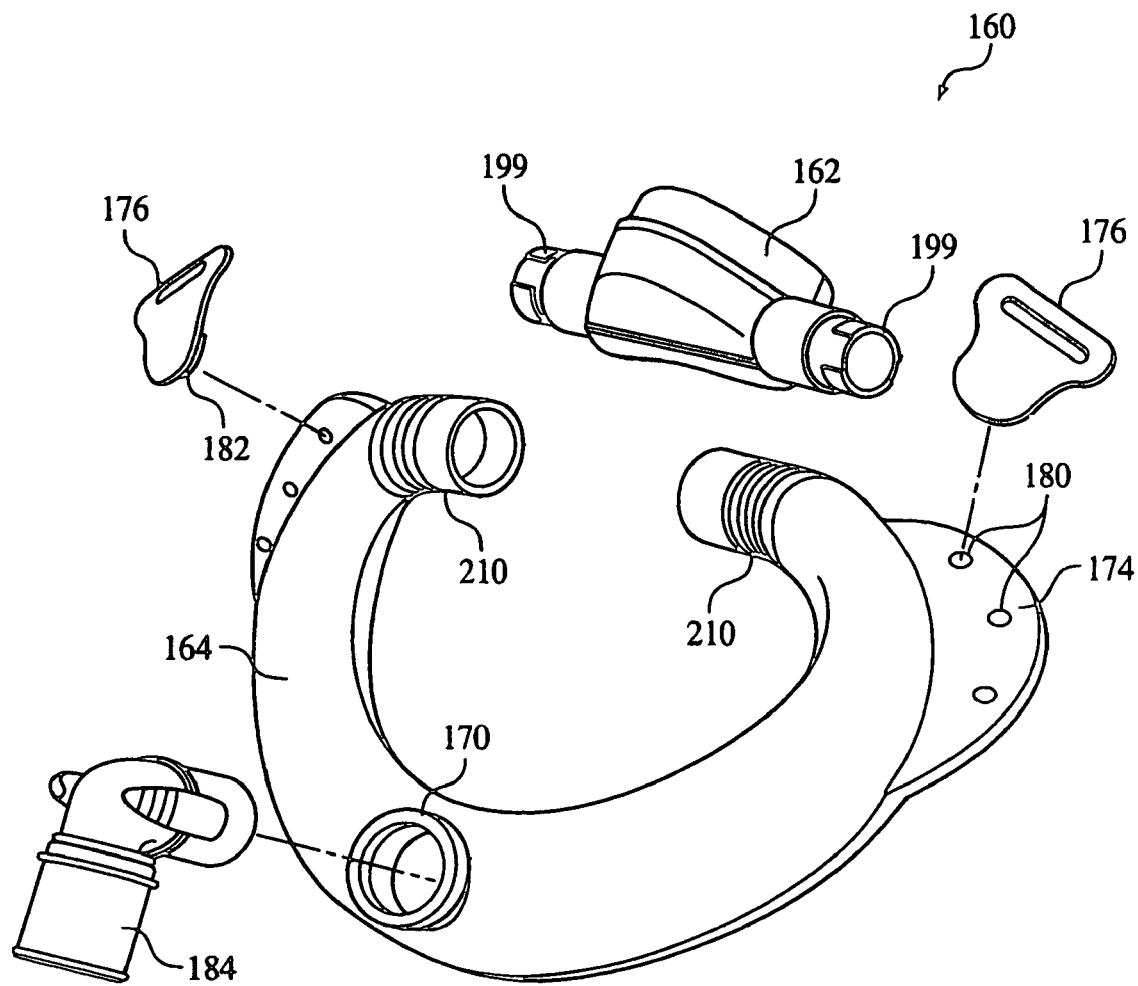
FIG. 21 is an exploded view of the patient interface assembly of FIG. 19.

FIGS. 18A and 18B show yet another embodiment of a patient interface 140 suitable for use with the patient interface assembly of FIG. 1. Patient interface 140 is similar to patient interface 48 of FIGS. 7 and 8. Patient interface 140 is a nasal mask 48 type of interface in that it encapsulates a least a portion of the nose. It includes a shell, seal, or cushion 142 that covers at least a portion of the nose of the patient with an opening 144 defined therein into which the nose is inserted. Lower corners 146 are connected to the chin support in any conventional manner, including the rotatable coupling techniques discussed above. In this exemplary embodiment, the entire patient interface assembly is formed from a unitary material, such as silicone or rubber.

FIGS. 19-26 illustrate a third embodiment of a patient interface assembly 160 according to the principles of the present invention. Patient interface 160 includes a patient interface 162 fluidly and rotatably coupled to a chin support 164, which is similar to chin support 14 discussed above with respect to FIGS. 1-5. Chin support 164 includes a patient contacting portion 166 and an exterior portion 168 that define a hollow tube suitable for communicating a flow of gas from a patient circuit coupling port 170 to patient interface 162. Patient contacting portion 166 is preferably formed from a soft substance, such as silicon, and/or includes a soft, patient contacting substance disposed thereon to maximize the comfort of the contact between the patient and the patient interface assembly.

For example, the present invention contemplates providing a removeable foam or fabric slip-on cover (not shown) that is provided over patient contacting portion 166. Such a slip-cover would provide benefits such as: (1) allow that patient's skin under the patient contacting portion to "breathe", (2) absorb moisture from the patient, and (3) maintain the cleanliness of the chin support over an extended period of time, especially if the slip-cover is periodically replaced with a new one or washed.

Chin support 164 is configured such that the patient's chin is received within opening 172 and the portion of the chin support proximate to port 170 is disposed under and supported against the mandible. This configuration provides a relatively secure mounting of the patient interface assembly on the patient. The relatively wide area of patient contacting portion 166 also enhances the stability of the interface on the patient.

Chin support 164 also includes connection pieces 174 to which a headgear attachment member 176 attaches. In a preferred exemplary embodiment, connection pieces 174 are provided on each leg of chin support 164 and are formed integrally with the chin support. It is to be understood, however, that connection pieces 174 can be separate structures that attach to the chin support in any conventional manner.

In the illustrated exemplary embodiment, a plurality of attachment openings 178 are provided in each attachment piece, and headgear attachment member 176 attaches to one of these openings by fitting a flange 180 provided on the headgear attachment member into the attachment opening. This configuration allows the headgear attachment member to swivel or rotate relative to the connection piece, as indicated by arrow A in FIG. 19. The multiple attachment openings provide adjustability in the location to which the headgear attaches to the chin support via the headgear attachment members. Slots are provided in each headgear attachment member 176 into which the headgear strap inserts. The present invention also contemplates proving openings in headgear attachment member 176 and multiple protrusions or flanges on the connection that fit into the opening on the headgear attachment member.

Patient circuit coupling port 170 is adapted to receive a patient circuit coupling 184 that attaches to a conventional conduit or patient circuit (not shown) to communicate a flow of gas from the pressure generating system to the interior of chin support 164. In use, patient circuit coupling port 170 is located near the position beneath or rearward the mental protuberance of the chin. Patient circuit coupling 184 includes a sleeve 186 and an elbow 188. Sleeve 186 preferably rotatably attaches to a first end of elbow 188 as indicated by arrow B in FIG. 23. The patient circuit attaches to sleeve 188. A second end of elbow 188 inserts into an opening in 190 of port 170.

An attachment mechanism is provided to couple the elbow patient circuit coupling port 170. In a preferred embodiment of the present invention, this attachment mechanism allows the elbow to rotate or swivel relative to chin support 164, as indicated by arrow C in FIG. 19, while also providing a quick attaching and detaching capability between the elbow and the chin support. This allows the patient to detach the entire patient interface assembly from the pressure generating system. This is important, for example, when a patient needs to get out of bed in the middle of the night for a short period of time and does not want to remove the entire patient interface assembly from their head, which may require readjusting the headgear.

The illustrated exemplary embodiment provides the rotating and removable coupling between the elbow and the chin support by providing a pair of attaching arms 192 attached to elbow 188 via an attachment support located generally in the middle of each arm. Attaching arms include a prong (not shown) at a first end 193 that inserts into a channel 194 provided in patient circuit coupling port 170. Channel 194 extends around the perimeter of port 170 that the elbow can rotate over a 360° range of angles relative to the chin support by allowing the prongs to slide along the channel. Of course a smaller range of rotation can be provided depending on the length of the channel.

Attaching arms 192 are biased such that the prongs remain engaged in channel 194 when the elbow is attached to the chin support. This biasing can be done by means of the materials used to construct the arms and/or by means of a dedicated bias mechanism, such as spring, coupled to the arms. Depressing on an end 196 of the arm deflects the prong outward from the axis of the elbow, so that the prong detaches from the channel. Attaching the prong into the channel is accomplished in a similar manner. It can be appreciated that other techniques can be used to provide these features of the present invention.

As in the embodiment shown in FIGS. 1-5, patient interface 162 is coupled to chin support 164 such that the patient interface is rotatable relative to the chin support, as indicated by arrow D in FIG. 19. Patient interface 162 includes a relatively rigid shell 198 that supports a cushion 200. Shell 198 is preferably formed from rigid plastic, such as polycarbonate and includes end portions 199 that include a conduit 201 defined therethrough to communicate a flow of gas from chin support 164 to patient interface 162. A channel 202 is formed in shell 198 that receives an edge 204 of cushion 200 in a tongue-and-groove fashion. Cushion 200 includes a flap 205 that attaches to shell 198. It is to be understood that the present invention contemplates that other techniques, such as a retaining ring or locking tabs, can be used to attach the cushion to the shell.

Cushion 200 is configured to contact a portion of the patient, such as the area of the face surrounding the nose, so that a portion of the patient, such as the nose, is received within the cavity defined within the shell and cushion. Cushion 200 is formed from any material suitable for this purpose, such as silicone, foam, rubber, gel, or any other conventional cushion material or combination of materials. Cushion 200 is generally triangular shaped having an apex 206 that rests on the center of the patient's nose. The end of the cushion opposite the apex includes a cutout 208 that rests on an area of the patient under the nose.

Figure 26:
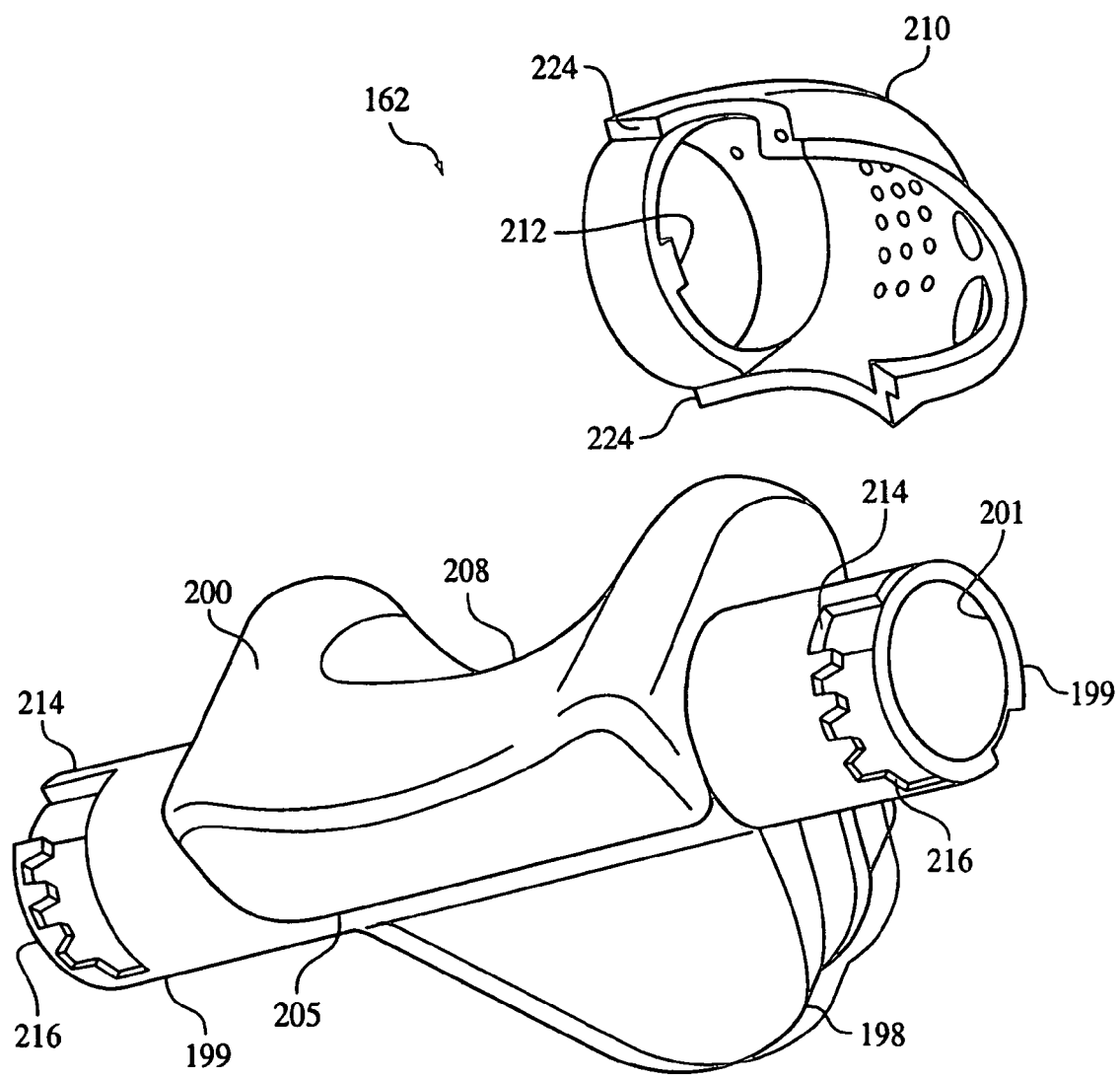
FIG. 26 is an exploded view showing the connection of the patient interface and the connecting tubing for the patient interface assembly of FIG. 19.

An exhaust port piece 210 is connected on each side of patient interface 162. Exhaust port piece 210 is preferably formed from rigid plastic, such as polycarbonate. A plurality of exhaust ports or openings are provided in the exhaust port pieces so as to allow an exhaust flow of gas exit the patient interface assembly. As shown in FIG. 26, exhaust pieces 210 preferably include an engaging tab 212 that inserts into a channel 214 defined in shell 198. A plurality of teeth 214 are provided in channel 216 to engage tab 212 in a ratchet-like fashion, so that the position of the patient interface can set in one of a number of discrete positions relative to the chin support.

Figure 22:
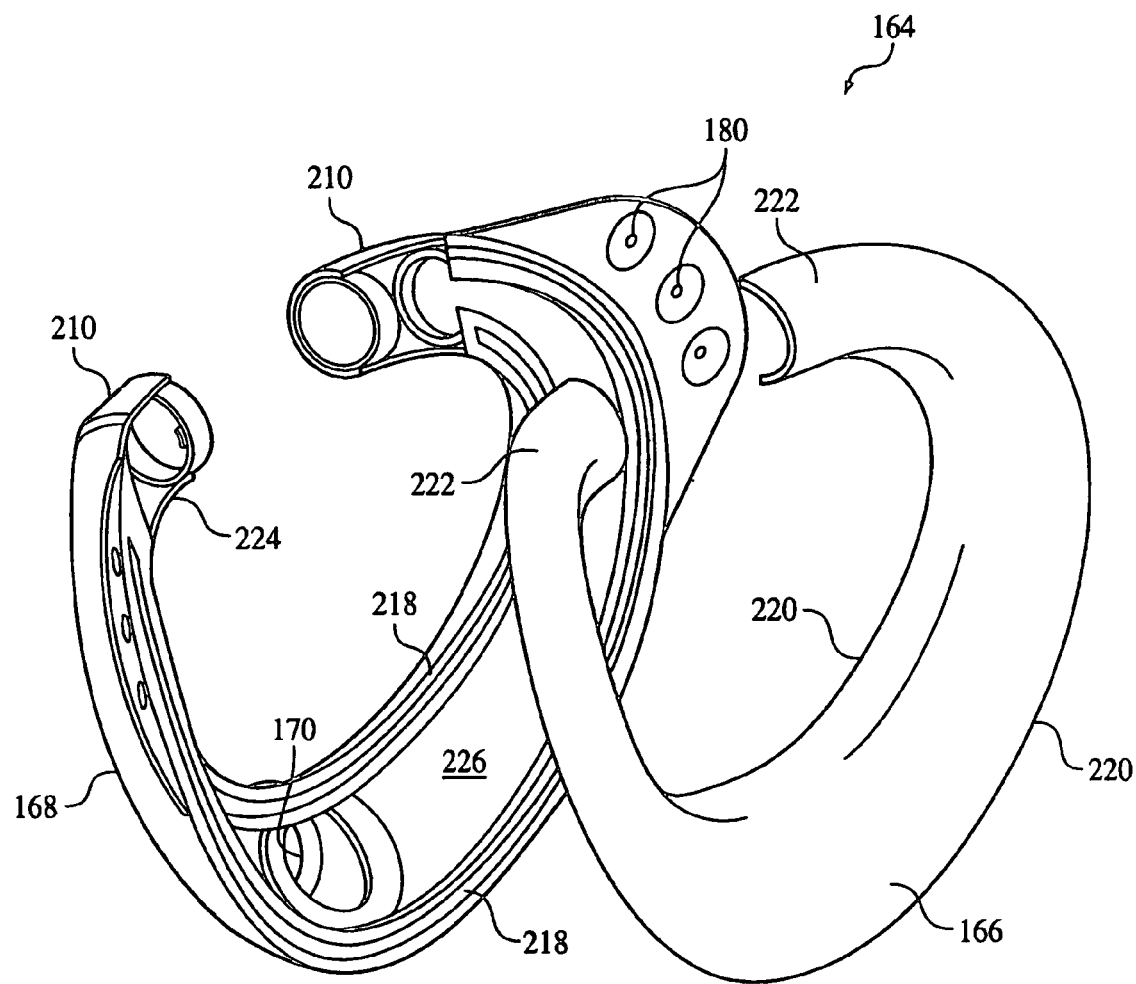
FIG. 22 is a further exploded view of the patient interface assembly of FIG. 1 showing how a portion of this interface is assembled.
Figure 23:
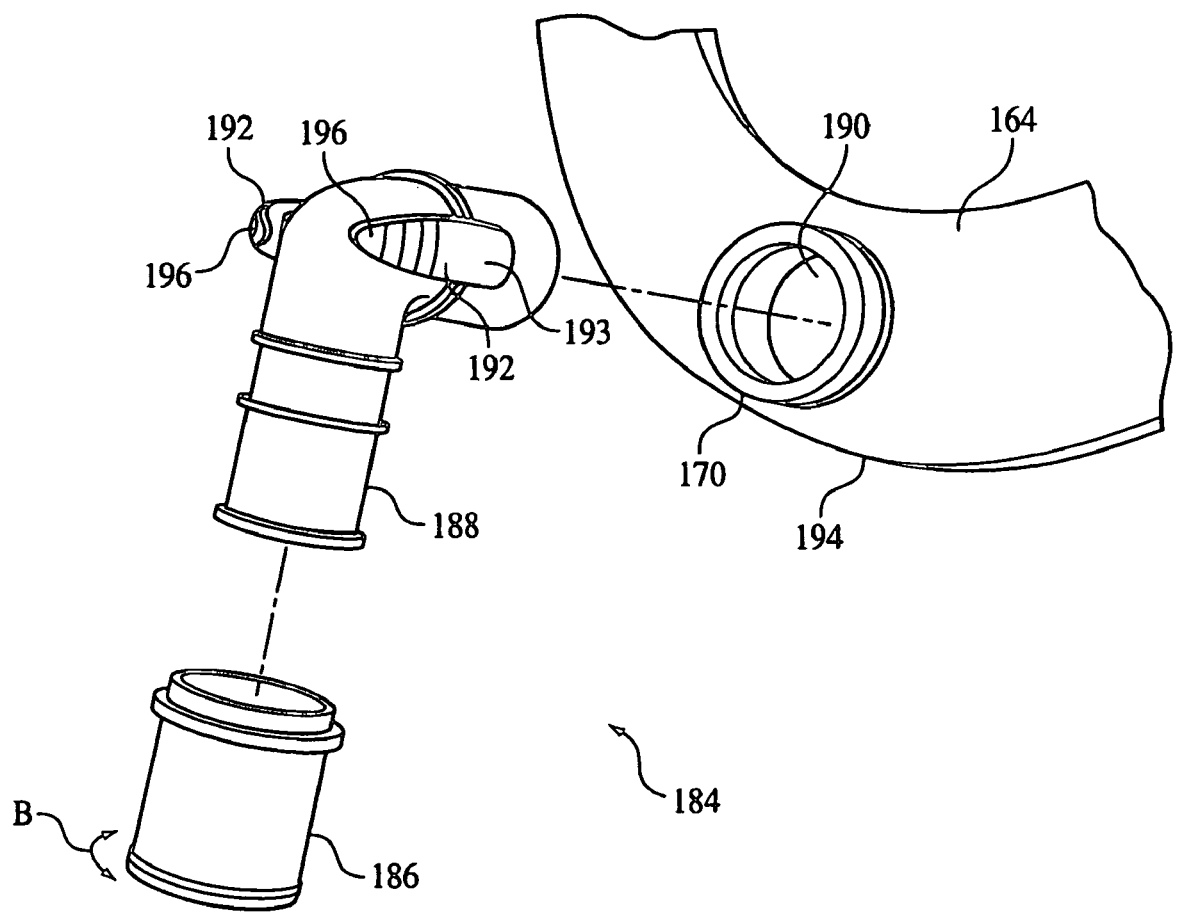
FIG. 23 is an exploded perspective view showing the connection of the patient circuit to the patient interface assembly of FIG. 19.
Figure 24:
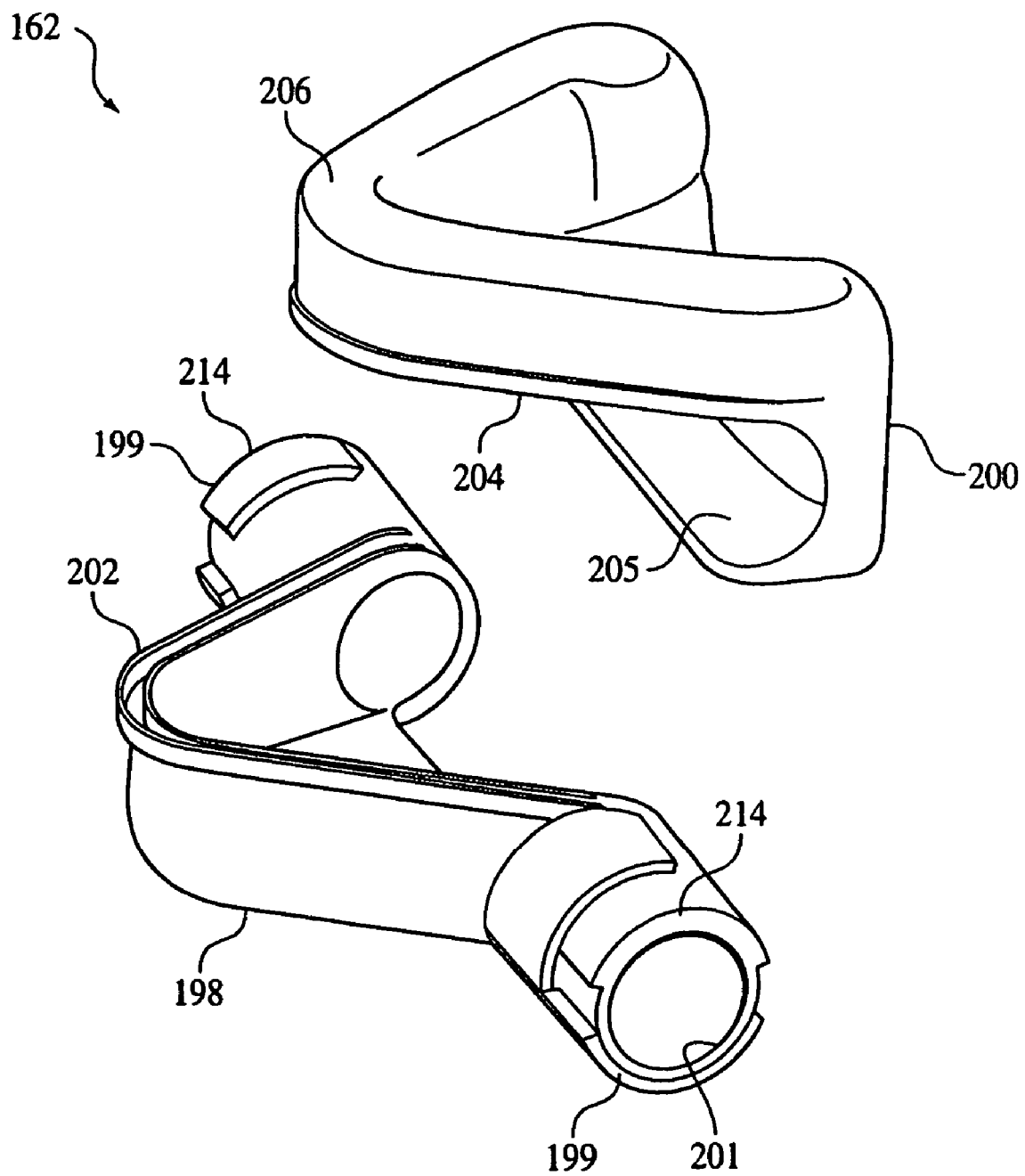
FIG. 24 is an exploded view of the patient interface, i.e., patient contacting portion of the patient interface assembly of FIG. 19.
Figure 25:
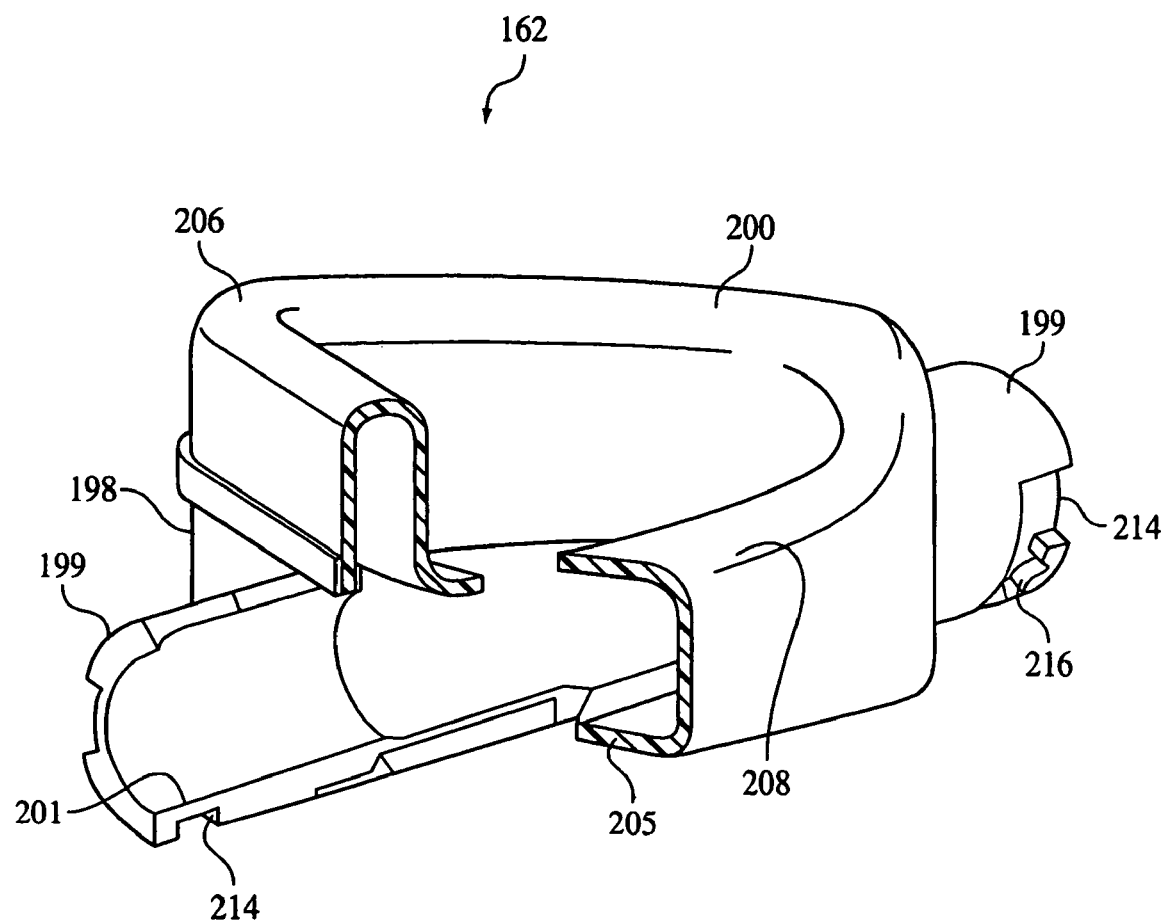
FIG. 25 is a cross-sectional view of the patient contacting portion shown in FIG. 19.

As shown in FIG. 22, the present invention contemplates forming chin support 164 by joining two halves: patient contacting portion 166, and an exterior portion 168. A channel 218 is provided in exterior portion 168 and a protrusion (not shown) is provided along edge 220 of patient contacting portion 166 that inserts into channel 218. The two halves can be joined in a permanent fashion using any conventional technique, such as an adhesive, weld, friction, or combination. End portions 222 of patient contacting portion 166 attach to exhaust port piece 210 such that edge 220 of patient contacting portion 166 align with a receiving channel 224 provided on exhaust port pieces 210. Thus, the rear side of the exhaust port piece is defined by end portion 222 of patient contacting portion 166. A cavity 226 is formed by the two halves of the chin support that carries gas from circuit coupling port 170 to patient interface 162.

It should be noted that the present invention contemplates that the two halves of the chin support need not have the same structural properties or characteristics. That is, patient contacting portion 166 and exterior portion 168 can be formed from different materials or from the same material but having different properties, such as different degrees of softness or hardness. For example, the exterior portion and patient contact portion can both be soft, one soft and one relatively hard, or both relatively hard. In the latter case, an additional slip-cover or other material can be provided over the patient contacting portion, either removably or permanently, to optimize patient comfort. In an exemplary embodiment of the present invention, exterior portion 168 is a relatively rigid to support exhaust port piece 210 and/or patient interface 162 and patient circuit coupling 184 and patient contacting portion 166 is a relatively soft piece to provide a comfortable surface that contacts the patient and gives a little to contour to the surface of the patient. It should also be noted that patient circuit coupling 184 and patient contacting portion 166 need not provide exactly one-half of the entire chin support. Rather, one piece of these pair of pieces can define a larger portion of the chin support than the other.

Figure 27:
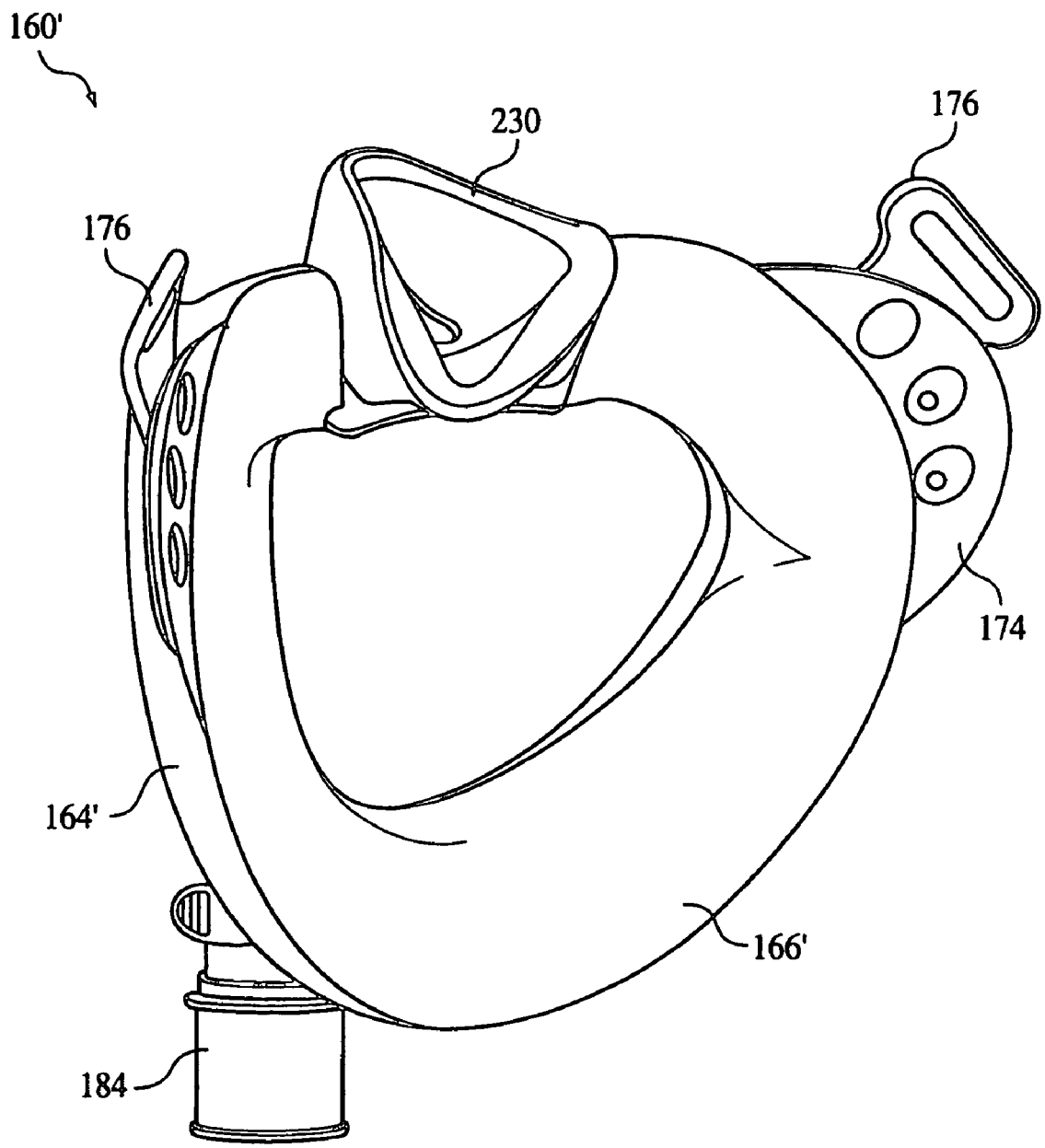
FIG. 27 is a rear perspective view illustrating another embodiment of a patient interface suitable for use in the patient interface assembly of FIG. 19.
Figure 28A:
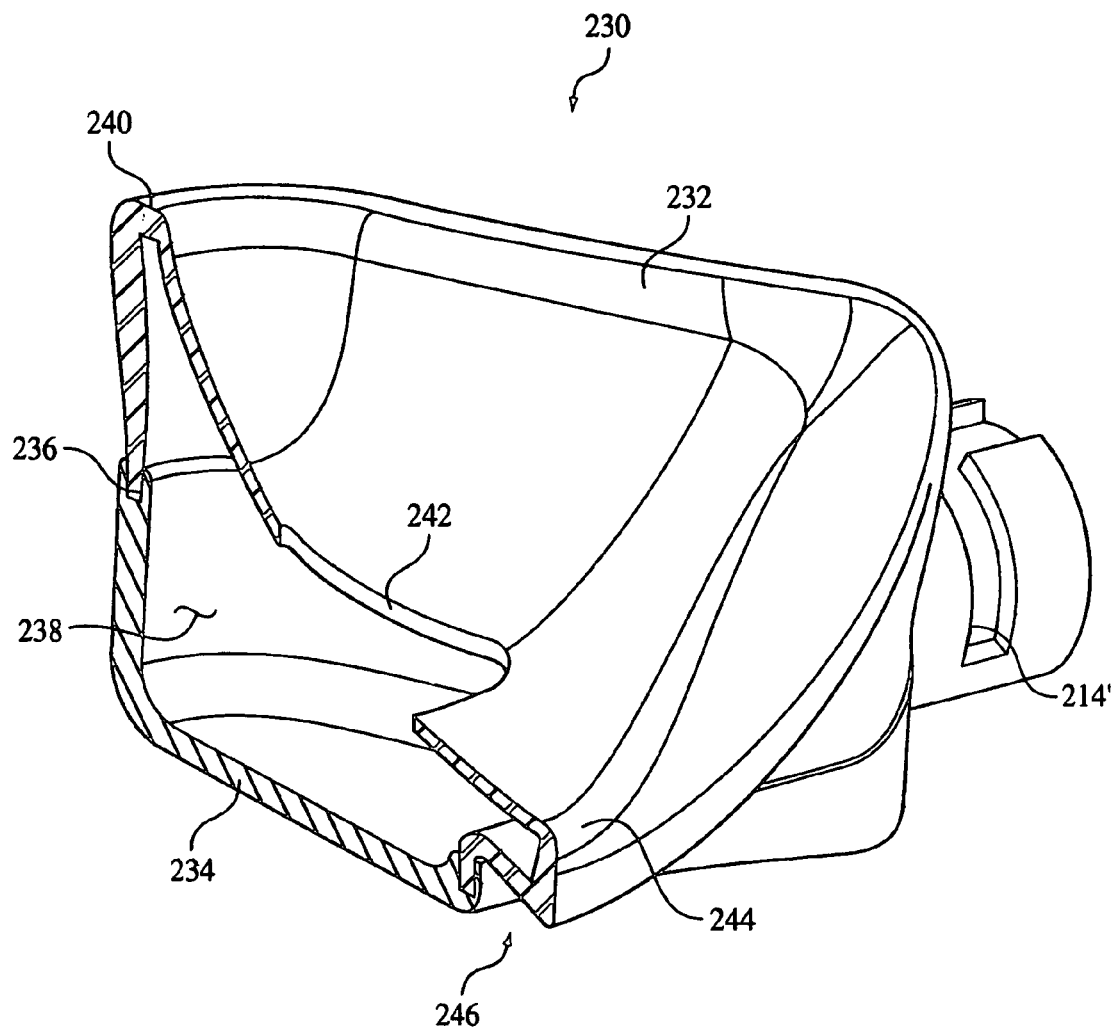
FIGS. 28A and 28B are cross-sectional views of the patient interface of FIG. 27.
Figure 28B:
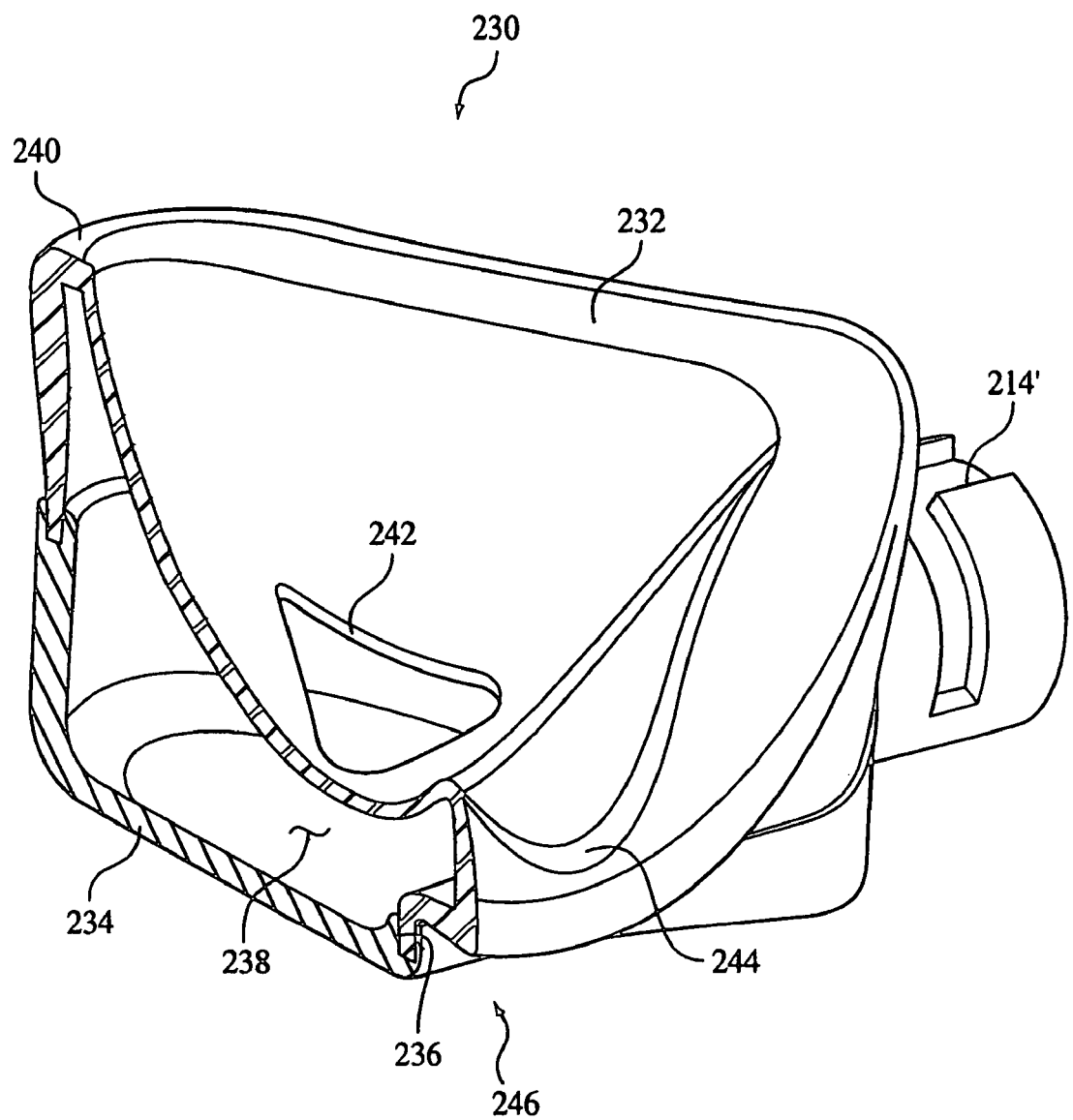
Figure 29:
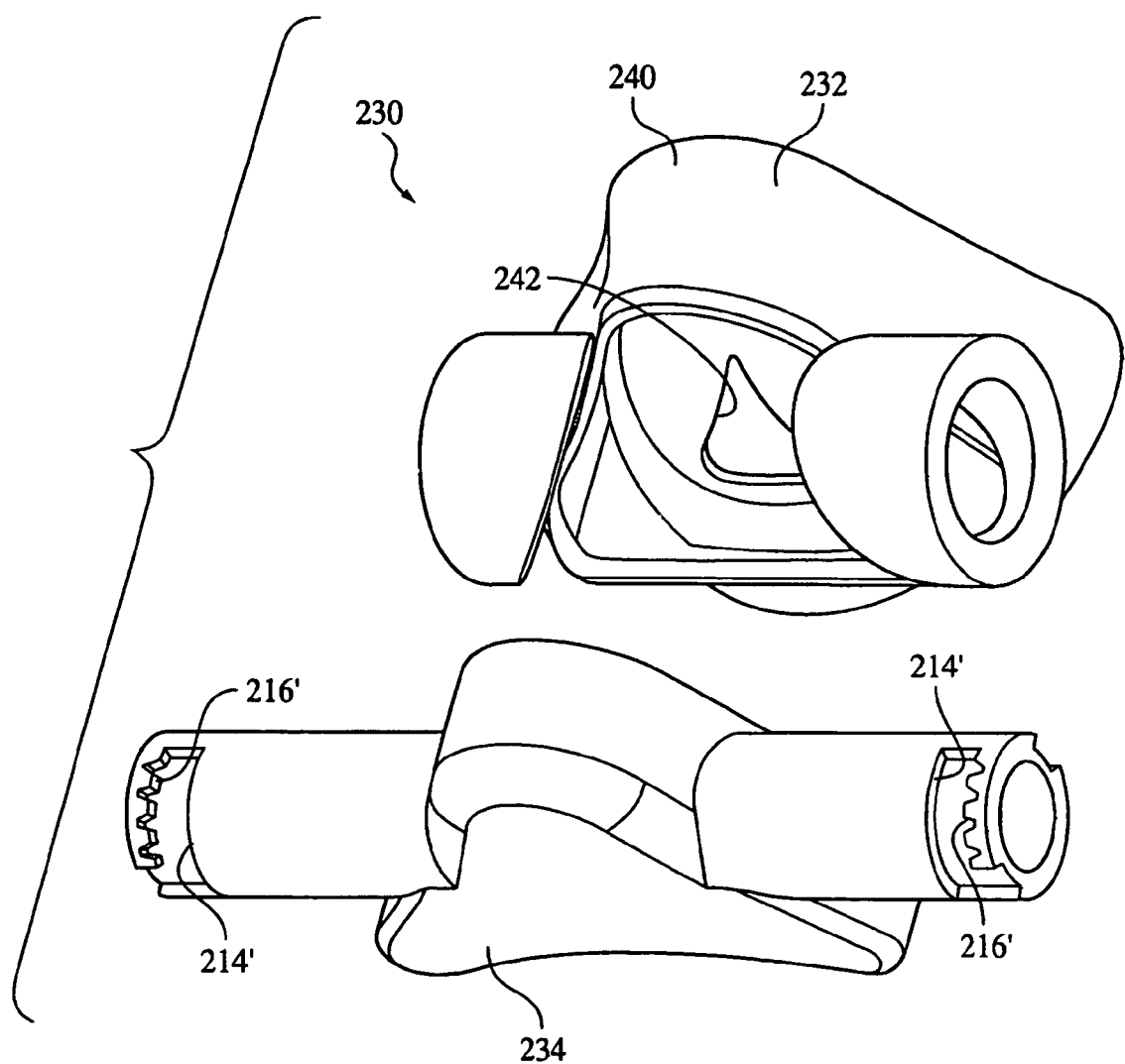
FIG. 29 is an exploded view of the patient interface of FIG. 27.

FIGS. 27-29 illustrate a patient interface assembly 160' that is similar to patient interface 160 except for the configuration for a patient interface 230 that attaches to chin support 164'. Therefore, the description of patient interface assembly 160' will focus the configuration of patient interface 230.

As perhaps best shown in FIGS. 28A-29, patient interface 230 includes a cushion 232 attached to a shell 234. In the illustrated exemplary embodiment, cushion 232 is attached to shell 234 by means of a channel 236 defined in the shell into which an edge of the cushion inserts. The edge of the cushion is fixed in the channel in any conventional manner, such as via friction, an adhesive, two-shot molding of the cushion of the shell, or any other conventional technique.

Cushion 232 is configured to contact a portion of the patient, such as the area of the face surrounding the nose, so that a portion of the patient, such as the nose, is received within a cavity 238 defined within the shell and cushion. Cushion 232 is formed from any material suitable for this purpose, such as silicone, foam, rubber, gel, or any other conventional cushion material or combination of materials. Cushion 232 is generally triangular shaped having an apex 240 that rests on the center of the patient's nose and is formed in a concave shape that overlies the nose of the patient.

An opening 242 is defined in the cushion. The patient's nose inserts into opening 242. The end of the cushion opposite apex 240 includes a cutout 244 that rests on an area of the patient under the nose. It can be appreciated that the concave shape of the cushion provides a folded-back feature, generally indicated at 246, at cutout 244 where the cushion is folded back on itself. This feature is believed to provide an increased comfort where the cushion contacts the patient as well as a good seal to prevent leakage of the gas at the patient-cushion interface.

It should again be noted that one advantage of the patient interface assembly illustrated in FIGS. 19-29 is that different patient interfaces can be used on the same chin support structure. This allows a health care provide to stock a common chin support, thereby avoiding inventory costs, while offering the patient a large selection of patient interface devices that can be mounted on the chin support, thereby maximizing interface design options for the patient. Another interesting aspect of the patient interface assembly shown in FIGS. 19-29 is that it can be reversed and worn by the patient such that the portion of the chin support that would otherwise rest below the mandible, rests on the user's forehead. This is made possible, should the user desire this configuration, by the ability to rotate the patient interface 180 degrees relative to the patient circuit.

Figure 30:
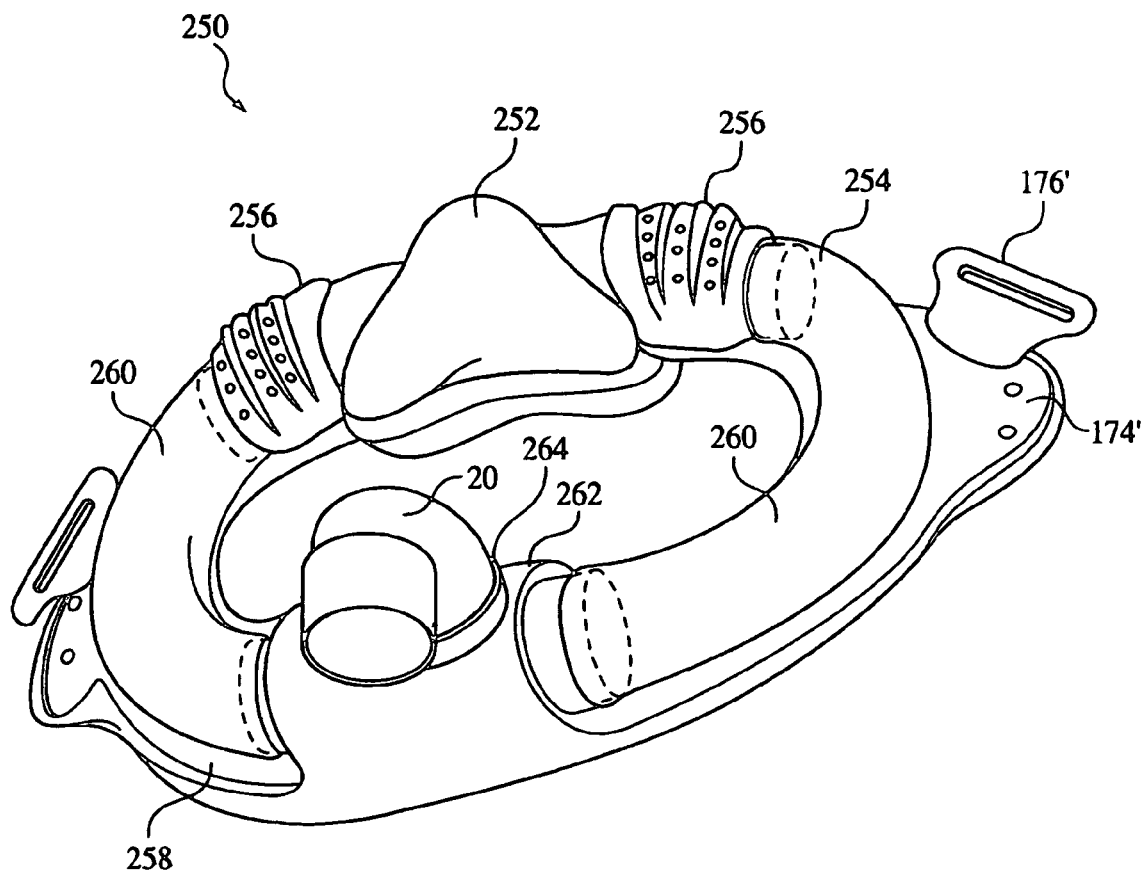
FIG. 30 is a front perspective view of a fourth embodiment of a patient interface assembly according to the principles of the present invention.
Figure 31:
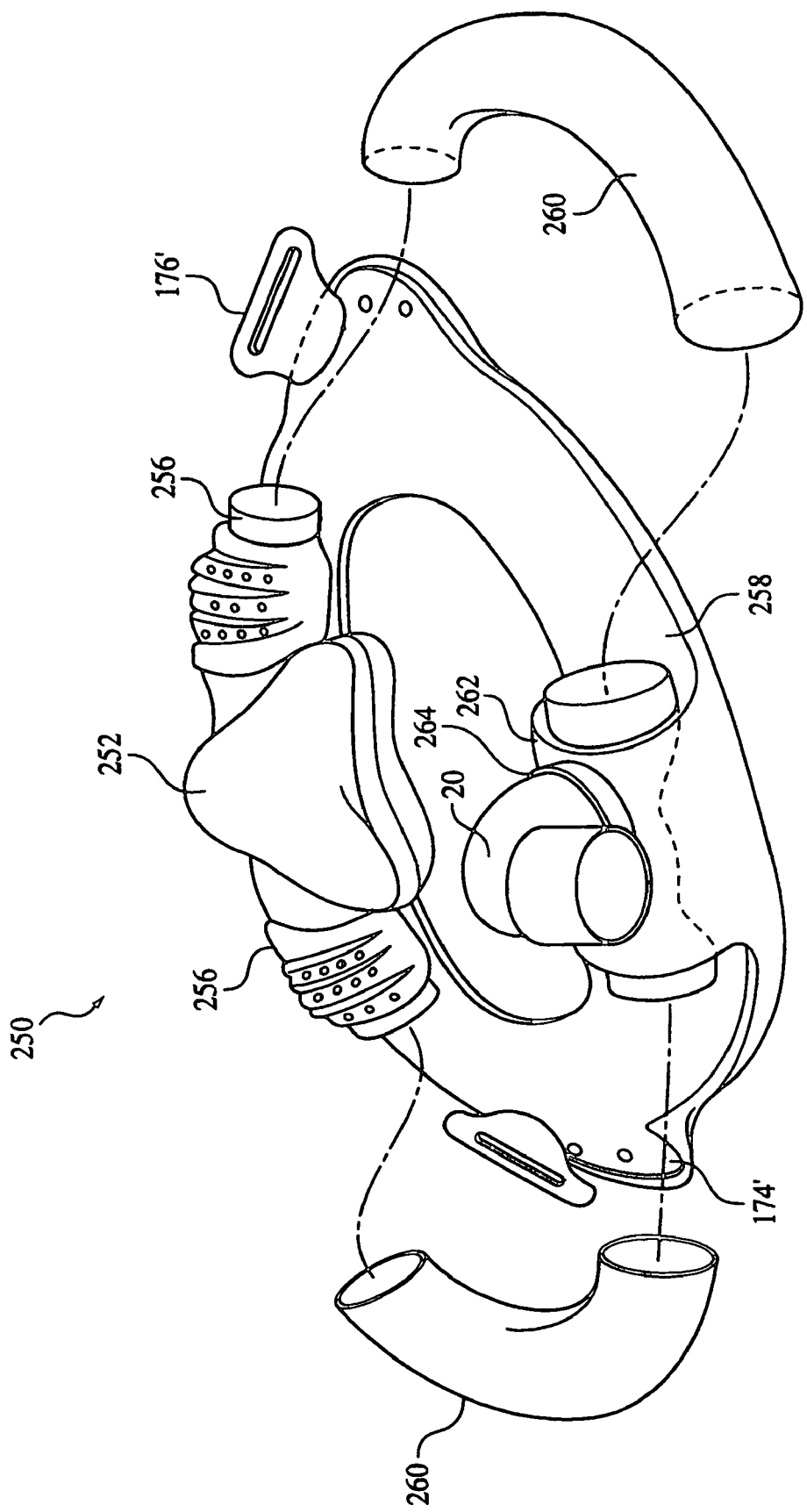
FIG. 31 is an exploded view of the patient interface assembly of FIG. 30.

FIGS. 30-31 illustrate a fourth embodiment of a patient interface assembly 250 according to the principles of the present invention. Patient interface assembly 250 includes a patient interface 252 coupled to a chin support 254. Patient interface 252 corresponds to any of the patient interfaces discussed herein and is preferably rotatably coupled to chin support 254 at exhaust port pieces 256 that include a plurality of openings that allow a flow of gas to be exhausted from the patient interface assembly.

Chin support 254 includes a support member 258 to which the other elements of the chin support, such as the exhaust port pieces, are mounted. Support member 258 is preferably rigid or semi-rigid so that it can support the components of the patient interface assembly. The patient contacting side of support member 258 is preferably formed from a soft substance, such as silicon, or includes a soft, patient contacting substance disposed thereon to maximize the comfort of the contact between the patient and the patient interface assembly.

Conduits 260 couple exhaust port pieces 256 to a patient circuit coupling portion 262 that is formed in support member 258. In a preferred embodiment, conduits 260 are detachably coupled to the remaining components of the patient interface assembly. Patient circuit coupling portion 262 couples the conduits to a patient circuit 20 via a patient circuit coupling port 264 such that the patient circuit can rotate relative to the chin support.

Figure 32:
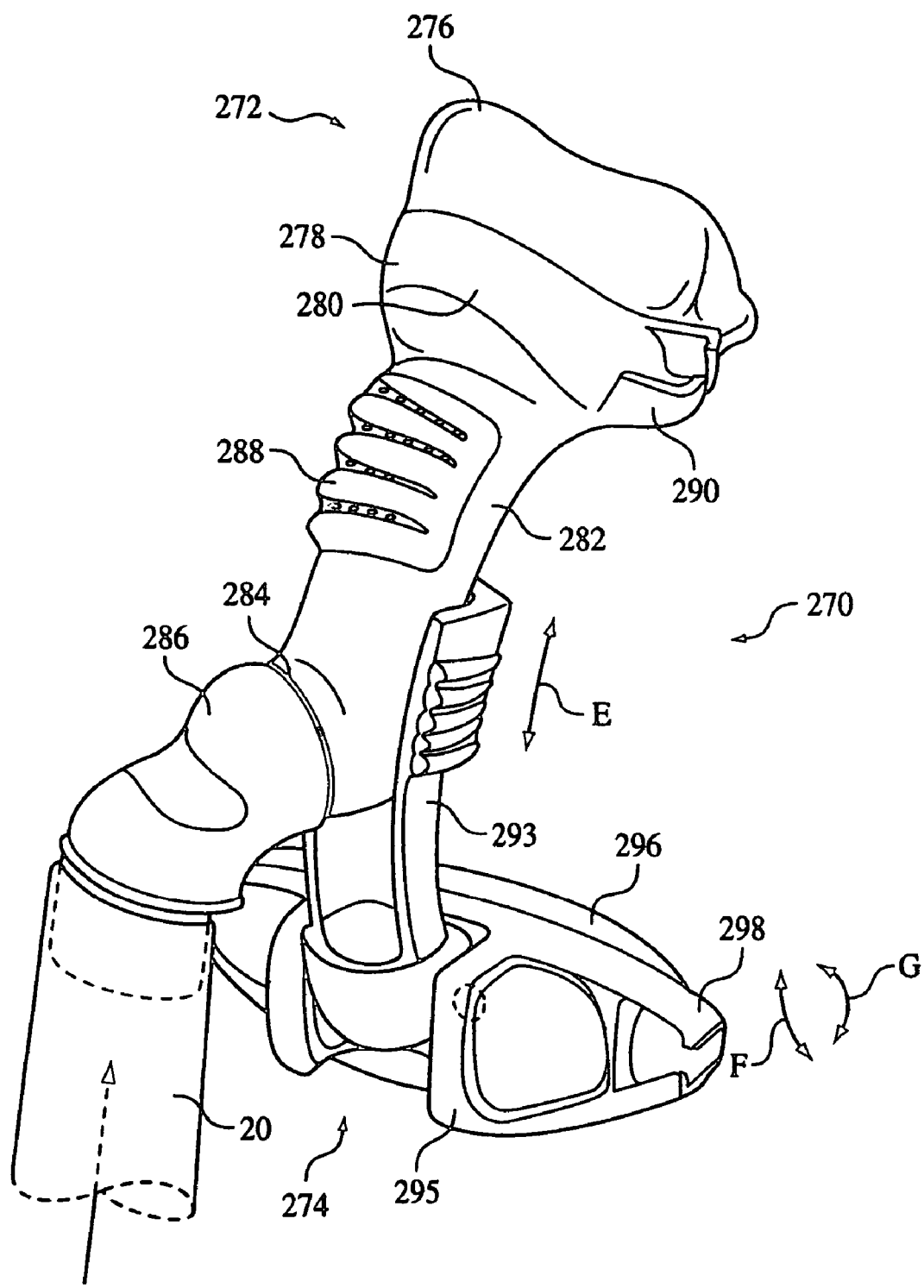
FIG. 32 is a front perspective view of a fifth embodiment of a patient interface assembly according to the principles of the present invention.
Figure 33:
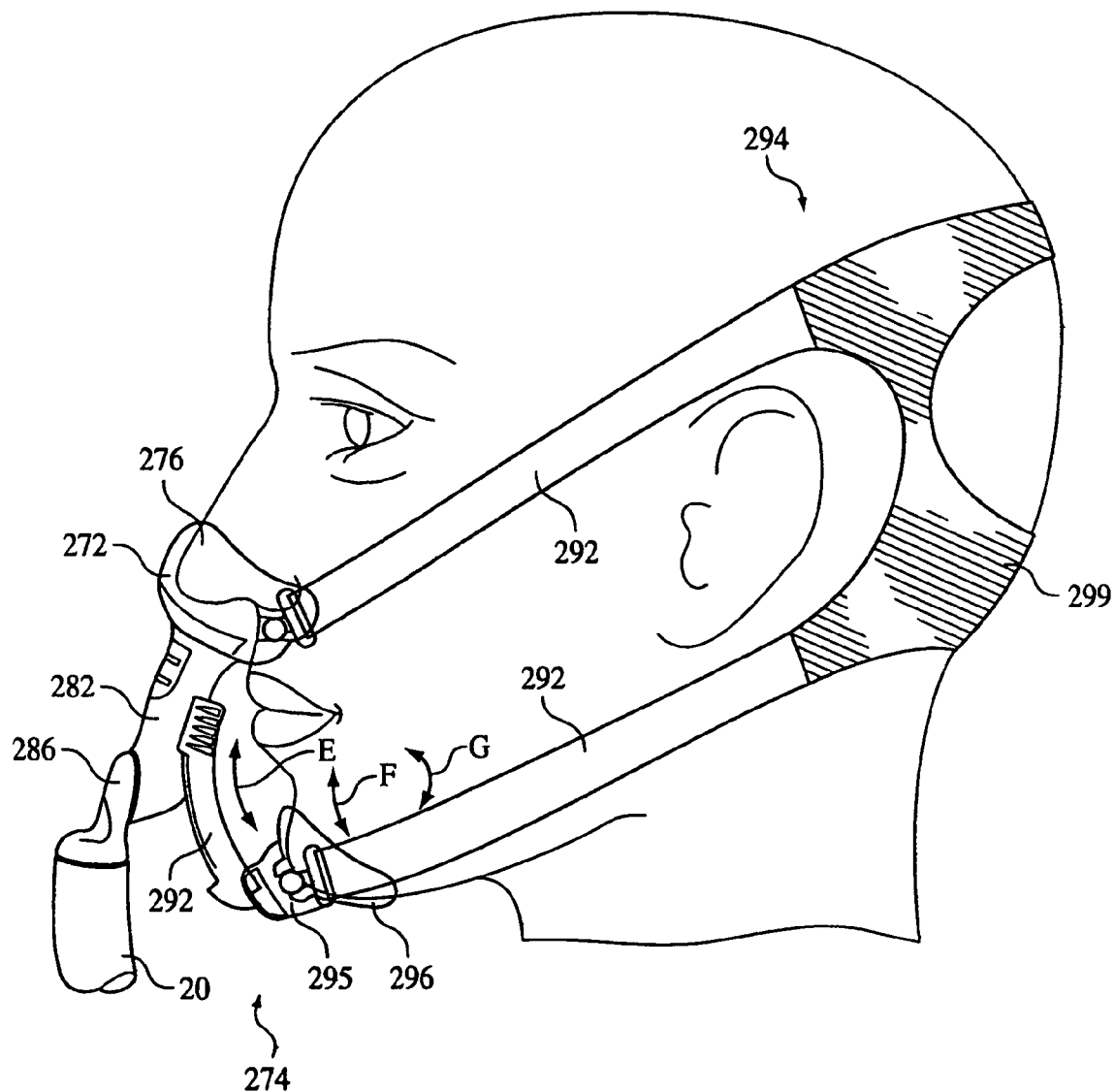
FIG. 33 is a side view of the patient interface assembly of FIG. 32 shown attached to a patient.

A fifth embodiment of a patient interface assembly 270 according to the principles of the present invention is shown in FIGS. 32 and 33. Patient interface assembly includes a patient interface 272 and a chin support assembly 274. Patient interface 272 includes a cushion 276 and a cushion support 278. Cushion support 278 includes a cushion mounting portion 280 to which the cushion is attached, and a hollow arm 282 that includes a patient circuit coupling port 284 that attaches to patient circuit 20. In the illustrated embodiment, an elbow coupling 286 connects the patient circuit to port 280. In an exemplary embodiment, elbow coupling 286 is rotatably attached to port 284. It is to be understood that the present invention contemplates connecting the patent circuit to arm 282 using any suitable coupling technique. Gas from the pressure generating system is provided to a cavity defined by cushion 276 via patient circuit 20, elbow coupling 286, and through the hollow interior of hollow arm 282.

An exhaust element 288 is also provided on arm 282. Exhaust element 288 includes a plurality of openings to exhaust gas from the patient interface assembly to ambient atmosphere. Headgear mounting elements 290 are provided on cushion mounting portion 280 of cushion support 278. In the illustrated exemplary embodiment, headgear mounting elements 290 are sockets to receive a ball portion attached to a headgear strap 292 in a ball-and-socket configuration. Such a ball-and-socket configuration is disclosed, for example, in pending published U.S. application Ser. No. 10/629,366 (publication no. US 2004-0025883 A1) the contents of which are incorporated herein by reference. It is to be understood that any conventional configuration for attaching the headgear strap to the cushion support 278 are contemplated by the present invention.

In the illustrated embodiment, cushion 276 is a nasal mask type interface and rests against the underside of the patient's nose. It is held in place by a headgear, generally indicated at 294. Cushion 276 is formed from any suitable material, such as foam, silicone, rubber, gel, or any combination thereof, and is preferably detachable from cushion support 278 so that it can be cleaned, or so that different sizes of cushions can be used on one size of cushion support. Chin support assembly 274, according to the illustrated exemplary embodiment, is generally T-shaped and includes a chin support arm 293 and a chin support bracket 295. Chin support bracket 295 is a substantially rigid member that supports a chin pad 296. Chin support assembly 274 includes headgear mounting elements 298 provided on chin support bracket 295 that are similar to headgear mounting elements 290, so that headgear straps 292 can be selectively attached to the chin support assembly. It is to be understood that the present invention contemplates using any conventional connection assembly for attaching the headgear straps 292 to the chin support assembly. Chin pad can have any suitable configuration and be formed from any material suitable for contacting the user.

Chin support arm 293 is adjustably coupled to arm 282 so that chin support assembly 274 is adjustable relative to cushion support 278. Arms 282 and 293 are preferably arc-shaped so that the chin support assembly takes place along an axis or curve, as indicated by arrow E, to allow the patient interface device to be adjusted to accommodate patients of different sizes, shapes, and comfort desires. This adjustment feature allows a patient to adjust the patient interface device in such a way as to minimize leakage and pressure on certain areas of the face. The attachment of chin support arm 293 to arm 282 is accomplished in any conventional manner, and controlling the relative position of the two arms can be achieved using any one of a variety of techniques. For example, the present invention contemplates providing a sliding friction engagement between arms 282 and 293. Of course, a ratchet-like mechanism can be used to control the relative positions between these arms. In addition, a locking pin or screw can be used to set the relative position of these two arms.

Chin support bracket 295 is adjustably connected to an end portion of chin support arm 293 via a slide-and-rotate arrangement. That is, chin support bracket 295 can both slide and rotate with respect to chin support arm 293. It can be appreciated that this configuration for the chin support bracket provides three independent positional adjustments for the chin support bracket relative to cushion support 278. First, the chin support bracket is capable of moving in a lengthwise direction, as indicated by arrow E. Second, the chin support bracket moves in a sliding direction, as indicated by arrow F. Finally, chin support bracket 295 pivots about an axis, as indicated by arrow G.

The present invention contemplates the headgear that can be used with the patient interface device can be any suitable headgear, i.e., any conventional headgear used in the patient interface field. For example, a typical headgear assembly comprises a headpiece 299 that overlies a portion of the patient's crania and with a pair of lower and a pair of upper headgear straps 292 extending therefrom to adjustably connect the headgear to the mask.

Figure 34:
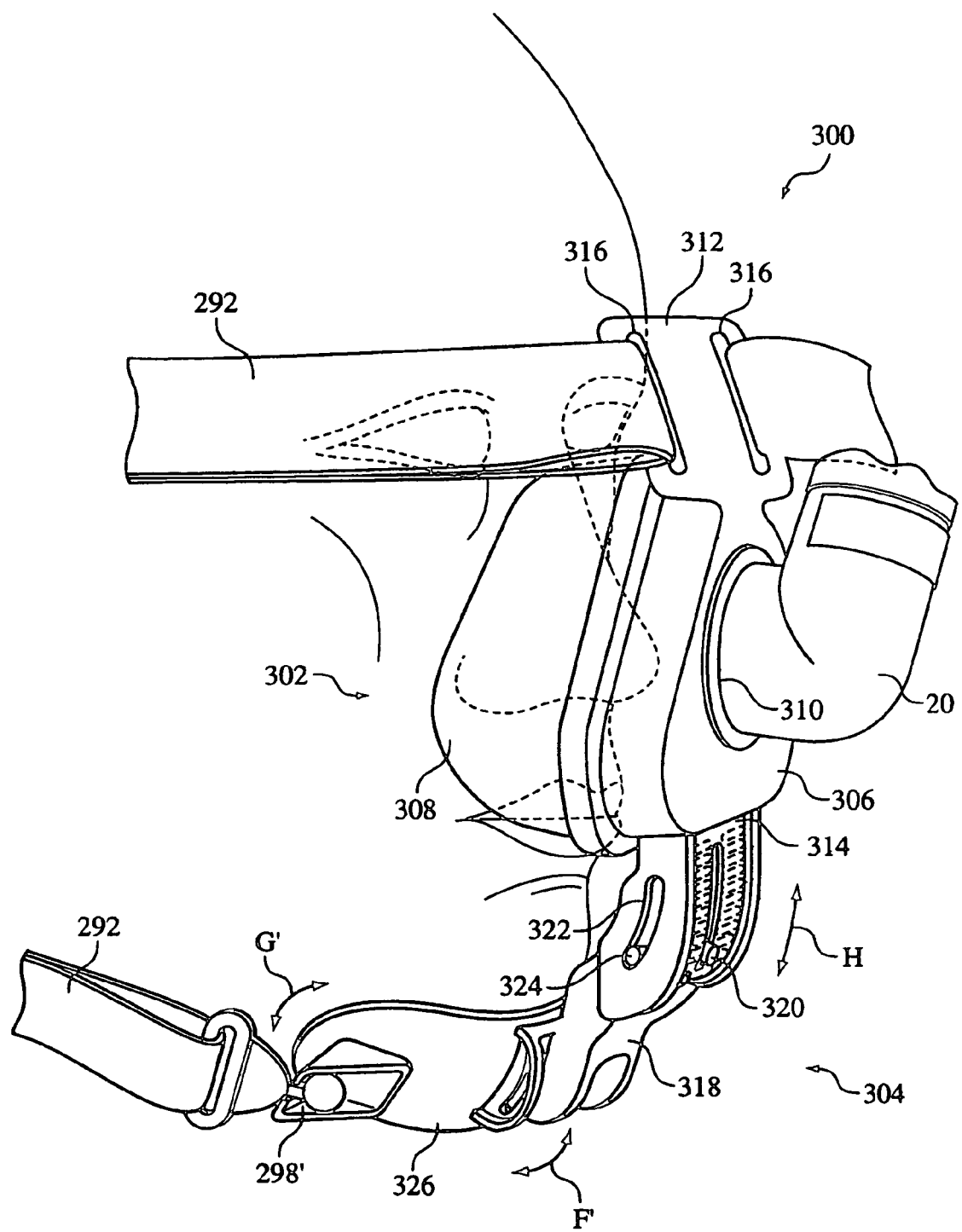
FIG. 34 is a front perspective view of a sixth embodiment of a patient interface assembly according to the principles of the present invention shown on a patient.

A sixth embodiment of a patient interface assembly 300, which is a variation of patient interface assembly 270 is shown in FIG. 34. Patient interface assembly 300 includes a patient interface 302 and a chin support assembly 304. In this embodiment, patient interface 302 includes a shell 306 that supports a cushion 308. Cushion 308 is a generally triangular shaped cushion that encompasses the user's nose, mouth, or both. The cushion is formed from any conventional material and is attached to shell 306 in any conventional manner. Shell 306 includes a patient circuit coupling port 310 that couples a patient circuit 20 to the shell in a rotatable fashion, so that gas is communicated from the patient circuit to a cavity defined by the shell and cushion, and ultimately to the patient's airway.

Shell 306 includes an upper extension 312 and a lower extension 314. In a preferred embodiment, the upper and lower extensions are integral with the shell. Upper extension 312 provides a location for attaching upper headgear straps to the patient interface assembly. In the illustrated embodiment, these attachment locations are in the form of slots 316 defined in upper extension 312. It is to be understood, however, that any conventional technique for attaching a headgear strap to the upper extension can be used.

A chin support arm 318 is coupled to lower extension 314 such that support arm 318 is slideable relative to lower extension 314 along an arc-shaped path, as indicated by arrow H. In this embodiment, a portion of support arm 318 is received within lower extension 314 and these two components are similarly shaped so that the support arm can slide within the lower extension. A plurality of teeth and teeth engaging members (not shown) are provided on support arm 318 and lower extension 314 so that the relative position between these two components can be controlled in a ratchet-like fashion. A push-button 320 is provided on support arm 318 to disengage the teeth engaging members and teeth. Push-button 320 also slides in a slot 321 to help guide the movement of the support relative to the lower extension. Guide slots 322 are also provided on the sides of lower extension 314 and guide members 324 are provided on support arm 318 to facilitate movement of support arm 318 relative to lower extension 314.

A chin support bracket 326 is adjustably coupled to support arm 318 and a chin pad is coupled to the patient contacting side of the chin support bracket. In this embodiment, chin support bracket 326 is a cup-shaped member that receives the user's chin. Chin support bracket 326 includes headgear mounting elements 298', which are similar to headgear mounting elements 290 and 298, so that headgear straps 292 can be selectively attached to chin support assembly 304. It is to be understood that the present invention contemplates using any conventional connection assembly for attaching the headgear straps 292 to the chin support assembly.

Chin support bracket 326 is adjustably connected to an end portion of support arm 318 via a slide-and-rotate arrangement, as done in the embodiment discussed above with respect to FIGS. 32 and 33. That is, chin support bracket 326 is configured to both slide and rotate with respect to support arm 318. It can be appreciated that this configuration for the chin support bracket provides three independent positional adjustments for the chin support bracket relative to patient interface 302. Lower extension 314 and the components coupled thereto, such as support arm 318 and chin support bracket 326, define chin support assembly 304.

Figure 35:
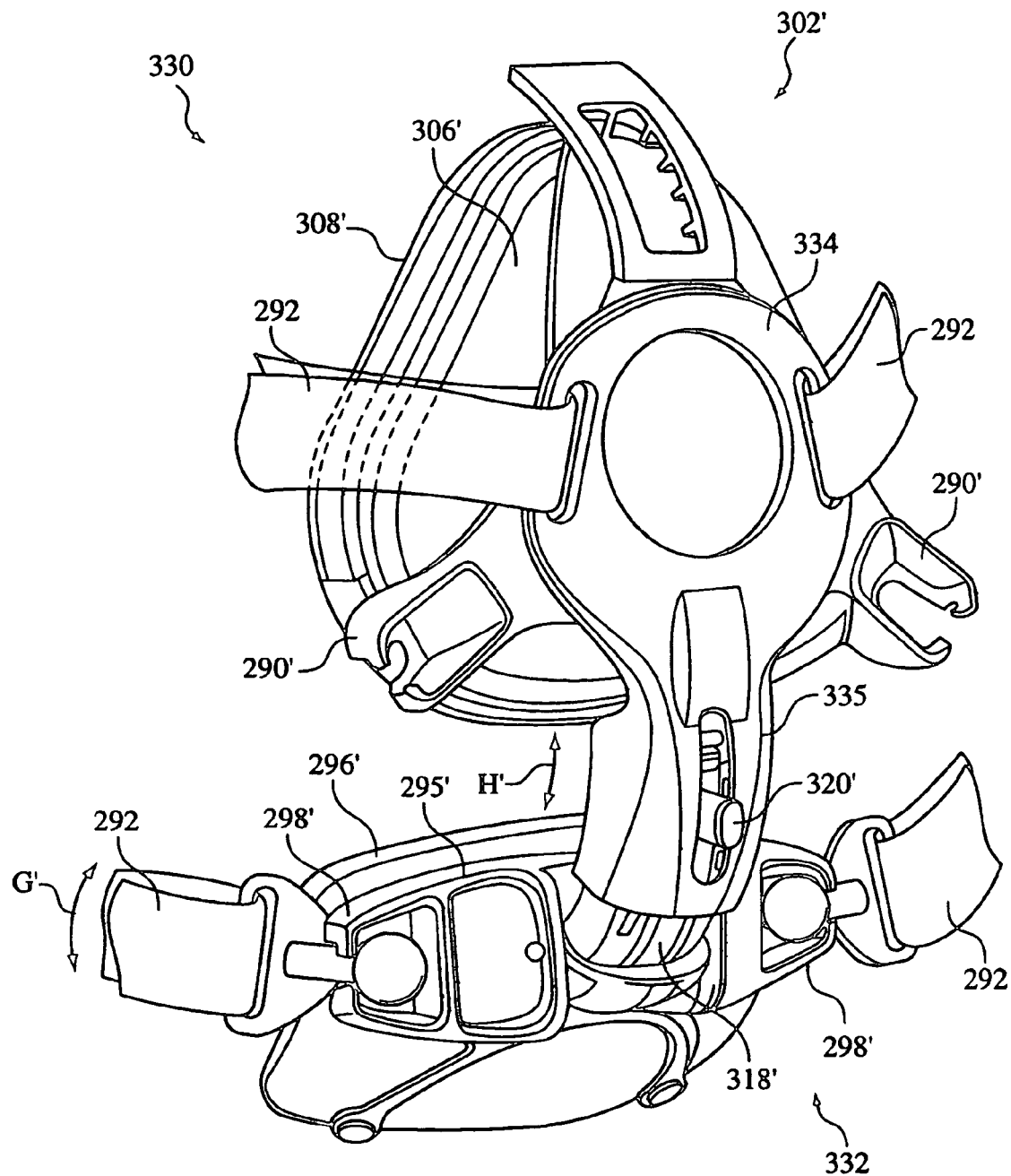
FIG. 35 is a front perspective view of a seventh embodiment of a patient interface assembly according to the principles of the present invention.
Figure 36:
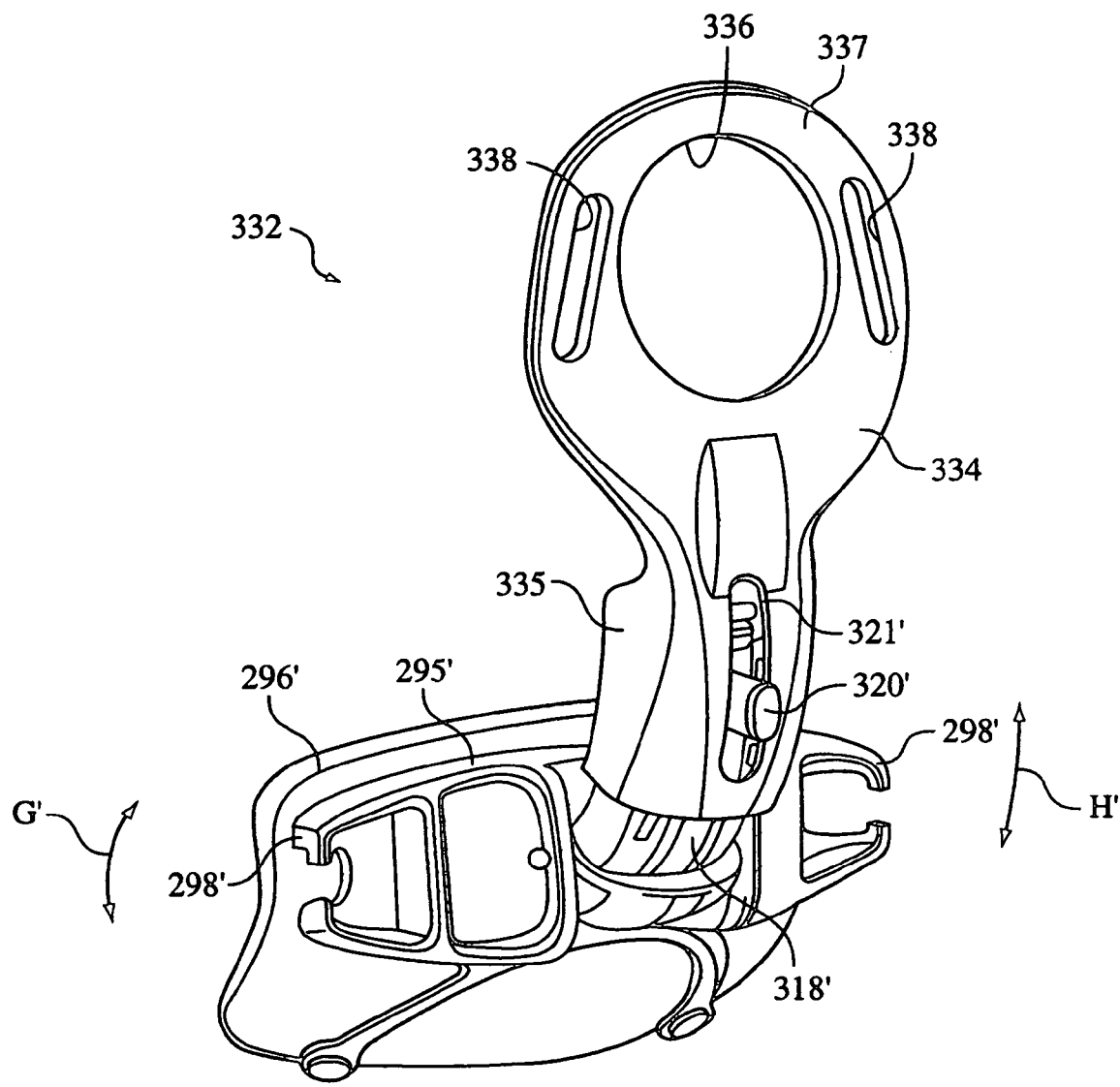
FIG. 36 is a front perspective view of the chin support portion of the patient interface assembly of FIG. 35.

A seventh embodiment of a patient interface assembly that is yet another variation of patient interface assembly 330 is shown in FIGS. 35-36. Patient interface 330 is generally similar to patient interface 300, except that a chin support assembly 332 in patient interface 330 is not integrally attached to shell 306'. In this embodiment, chin support assembly 332 includes a mounting member 334 that attaches to a patient interface 302'. Mounting member 334 includes a lower extension 335 that attaches to a chin support arm 318' in generally the same manner that lower extension 318 attached to chin support arm 318 discussed above.

Preferably mounting member 334 is capable of being retrofit onto an existing mask so that the chin support assembly can be added, if necessary, to a conventional mask. For example, mounting member 334 illustrated in the figures includes an opening 336 defined in an upper end 337 of the mounting member. The chin support assembly fits over a patient circuit coupling port defined in the patient interface to enable the patient circuit, elbow coupling, or other gas carrying conduit passes through opening 336.

Although not necessary, the present invention contemplates attaching the headgear directly to mounting member 334. For this purpose, slots 338 are provided on the mounting member to which the headgear straps attach. Of course, the headgear can be attached to the mounting member using any conventional technique. It should be noted that mounting member 334 can have shapes, sizes, and features other than those shown in the figures, for example, to accommodate other types of headgear attachments elements, such as sockets, snaps, claps, hooks, etc.

Figure 37:
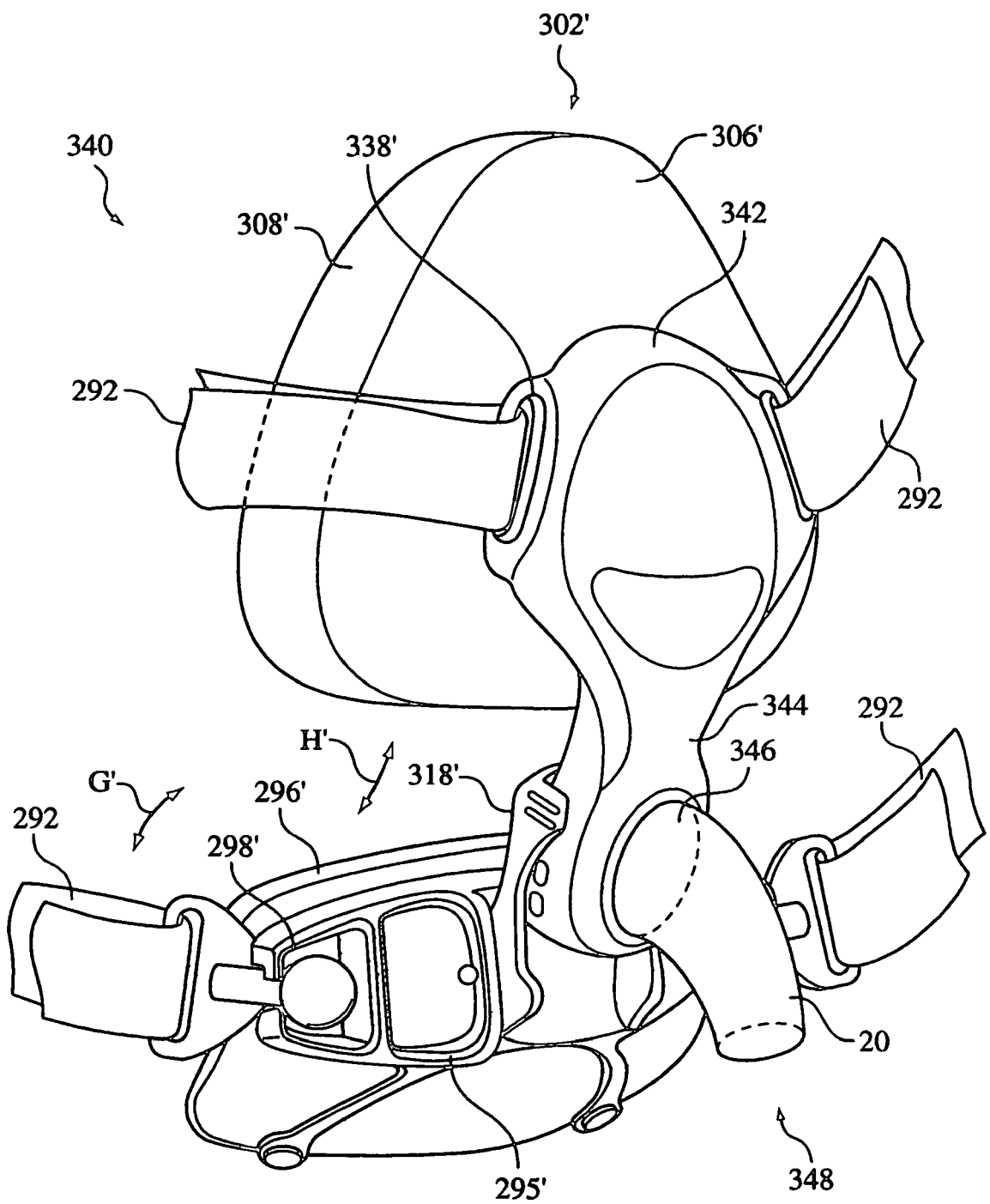
FIG. 37 is a front perspective view of an eighth embodiment of a patient interface assembly according to the principles of the present invention.

An eighth embodiment of a patient interface assembly 340, which is generally similar to patient interface assembly 330, is shown in FIG. 37. Patient interface assembly 340 includes a mounting member 342 that is attached to shell 306' in patient interface 302'. Preferably mounting member 342 is rotatably attached to shell 306' and includes headgear mounting elements, such as slots 338', to attach the headgear to the mounting member. Unlike mounting member 334, mounting member 342 includes a hollow lower extension 344 that attaches to a patient circuit 20 via a patient circuit coupling port 346 and defines a portion of a chin support assembly, generally indicated at 348.

As in the previous embodiment, chin support assembly 347 includes a chin support arm 318' that is slideably coupled to lower extension 344. Preferably, patient circuit 20 is rotatably attached to coupling port 346. This embodiment moves the attachment of the patient circuit to a point lower on the face of the patient, so that any torque present on the patient circuit is more equally distributed on patient interface 302' and chin support assembly 348.

Figure 39:
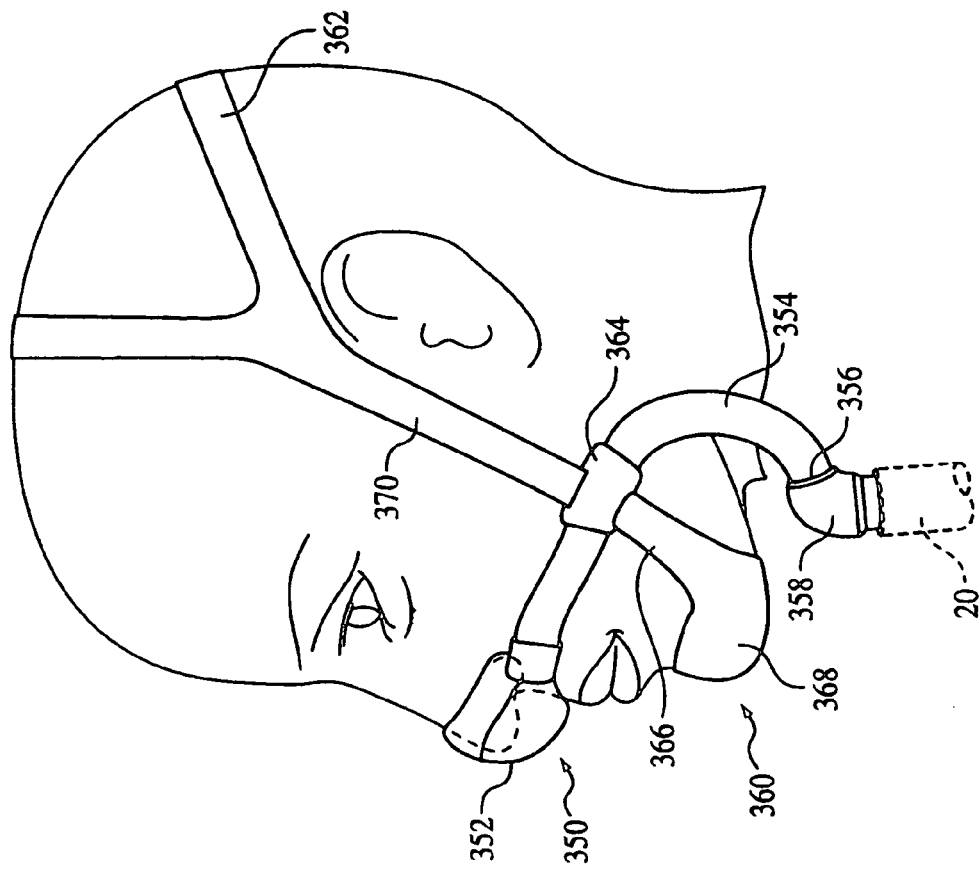
FIG. 39 is a side view of the patient interface assembly of FIG. 38.
Figure 38:
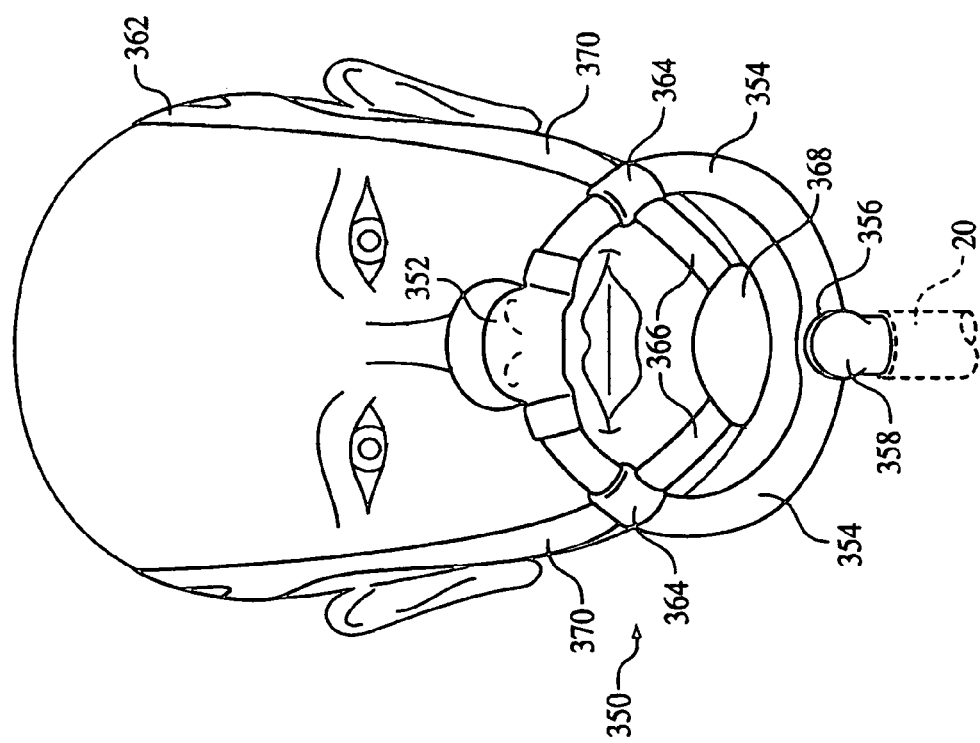
FIG. 38 is a front view of a ninth embodiment of a patient interface assembly according to the principles of the present invention.

Referring now to FIGS. 38 and 39, a ninth embodiment of a patient interface assembly 350 according to the principles of the present invention will be discussed. Patient interface assembly 350 is somewhat similar to patient interface assembly 10 shown in FIGS. 1-5, except that a different configuration is used to support the assembly on the user's mandible.

Patient interface assembly 350 includes a patient interface 352 coupled to conduits 354. In a preferred embodiment of the present invention patient interface 352 is a nasal mask or nasal prong type interface that is rotatably coupled to conduit 354. A patient circuit coupling port 356 is provided at an end of the conduit to couple the patient circuit 20 to the patient interface assembly. The present invention contemplates providing an elbow coupling 358 at port 356 for this purpose.

In an exemplary embodiment, conduits 354 are flexible enough so that they can flex to some degree to conform to the facial features of the patient, yet sufficiently rigid to retain enough structural integrity to support the patient interface on the user's airway. The structural integrity of the conduits can be provided by the materials defining the conduit and/or by separate structure enhancing elements, such as wire or rods coupled to or imbedded in the conduit. The present invention also contemplates that the conduits can be entirely rigid.

Conduits 354, including patient interface 352, are attached to the patient via a chin support assembly, generally indicated at 360, and a headgear assembly 362, both of which are connected to the conduit via an attachment member 364. Chin support assembly 360 includes chin straps 366 and a chin engaging member 368, which are preferably formed from a soft-comfortable material, such as fabric, foam, or an elastomeric material. Examples of such material include a Lycra® foal lamination, neoprene, or TPE. Chin straps 366 and chin engaging member 368 can be formed from the same material, formed integrally with one another, or formed separate from different materials.

Headgear assembly 362 includes headgear straps 370. The headgear assembly includes a headpiece that overlies a portion of the patient's crania, such as cap or bifurcated straps, as shown in FIG. 39. It is to be understood that the present invention contemplates that any conventional configuration or attachment technique can used as the headgear assembly to maintain the patient interface assembly on the patient's head. For example, the present invention contemplates providing a mechanism that allows the length of the headgear straps to be adjusted.

Figure 41:
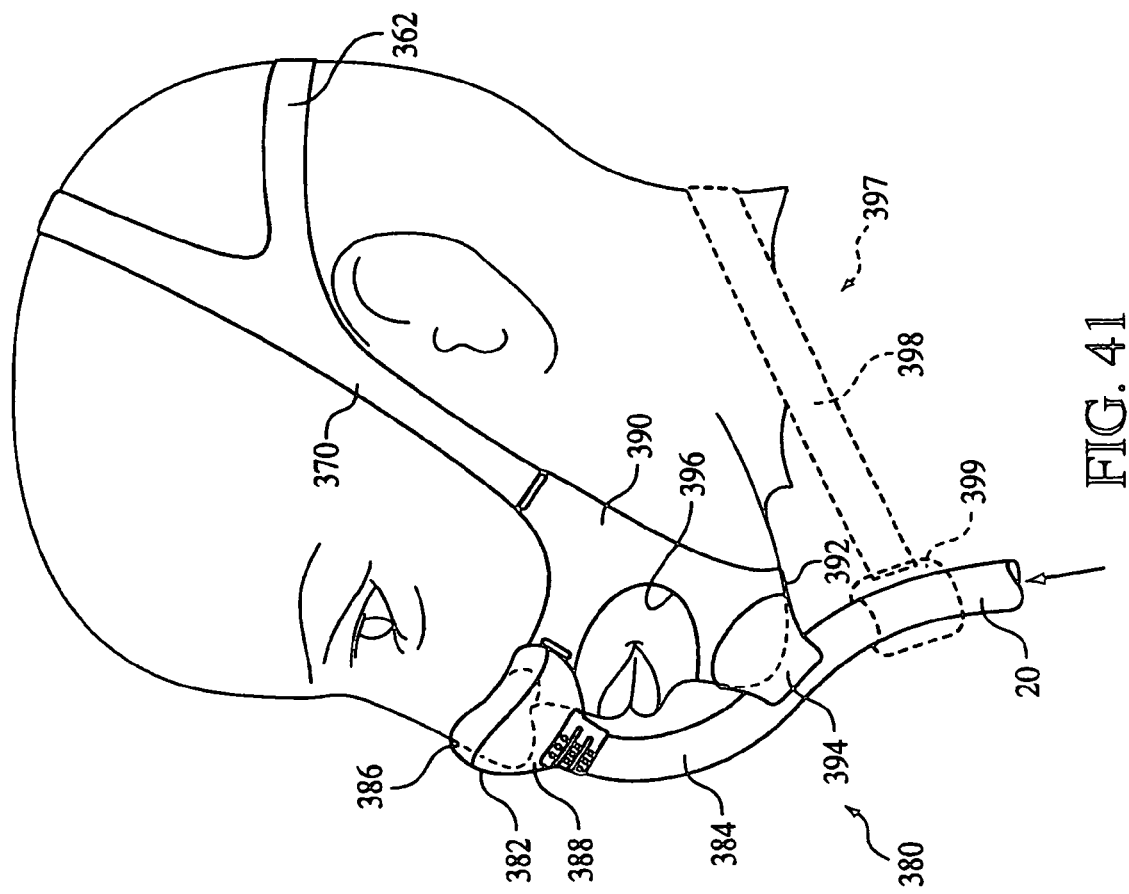
FIG. 41 is a side view of the patient interface assembly of FIG. 40.
Figure 40:
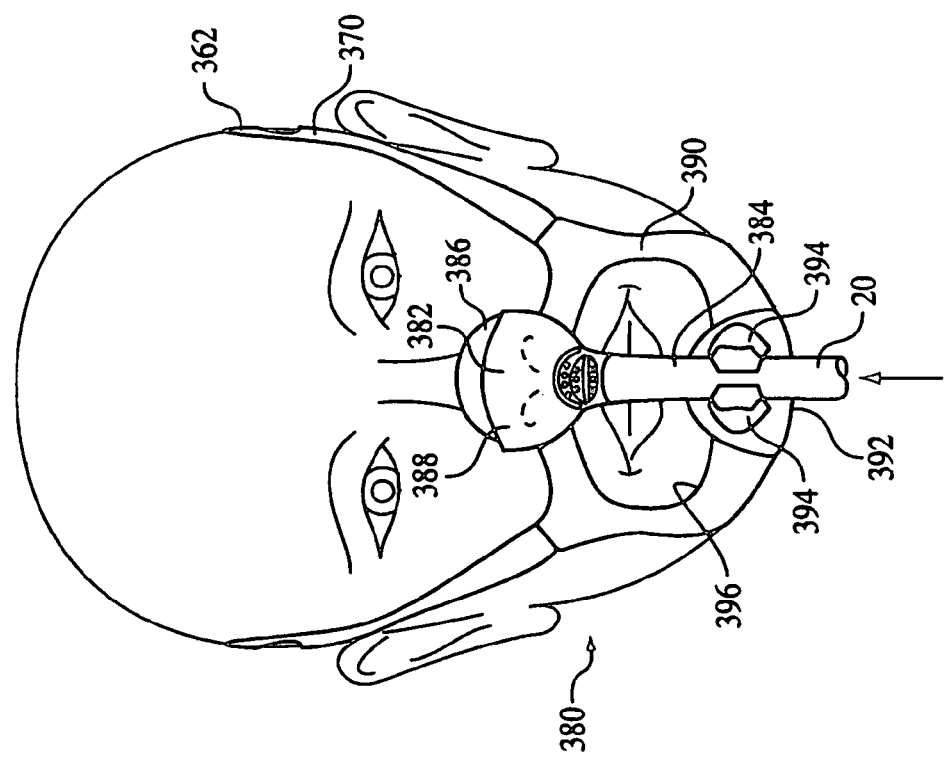
FIG. 40 is a front view of a tenth embodiment of a patient interface assembly according to the principles of the present invention.

FIGS. 40 and 41 illustrate a tenth embodiment of a patient interface assembly 380 according to the principles of the present invention. Patient interface assembly 380 includes a patient interface 382 coupled to a conduit 384, which effectively corresponds to an end of patient circuit 20. In the illustrated embodiment, patient interface 382 is a nasal mask type interface that includes a cushion 386 and a relatively rigid cushion support 388.

Conduit 384 and patient interface 382 are attached to the patient via a chin support assembly 390 that is held on the patient by means of headgear assembly 362. Chin support assembly 390 includes a lower portion 392 that overlies the patient's chin, and is preferably situated under the chin when the patient interface assembly is donned by the patient. A conduit coupling structure is provided on portion 392 to assist in maintaining a proper position for conduit 384 so that a torque force acting on the conduit is not imparted on the patient interface. In the illustrated embodiment the conduit coupling structure includes a pair of engaging arms 394 that pinch or hold the conduit to the support member. Arms 394 allow the conduit to be detached and reattached to chin support assembly 390. In addition, the frictional engagement between the arms and the conduit allowed the conduit to be moved relative to the chin support and maintained in the new position so that the patient interface assembly can be configured to fit on differently sized and shaped patient.

Chin support assembly 390 is configured to correspond to the lower portion of a human face and is preferably configured from a non-rigid material so that the chin support assembly can fit a variety of different sized and shaped faces. An opening 396 is provided in the support member so that the patient's mouth remains exposed. Chin support assembly 390 can be formed integral with the headgear assembly or as a separate element, that is either fixed to or selectively attachable to the headgear assembly.

An optional conduit coupling assembly 397, shown in FIG. 41, can be used in conjunction with patient interface assembly 380. Optional conduit coupling assembly 397 includes a neck strap 398 that attaches to the patient's neck and an attachment 399. Optional conduit coupling assembly 397 provides an additional mechanism for controlling the position of patient circuit 20/conduit 384 to prevent twisting of the patient interface.

Figure 42:
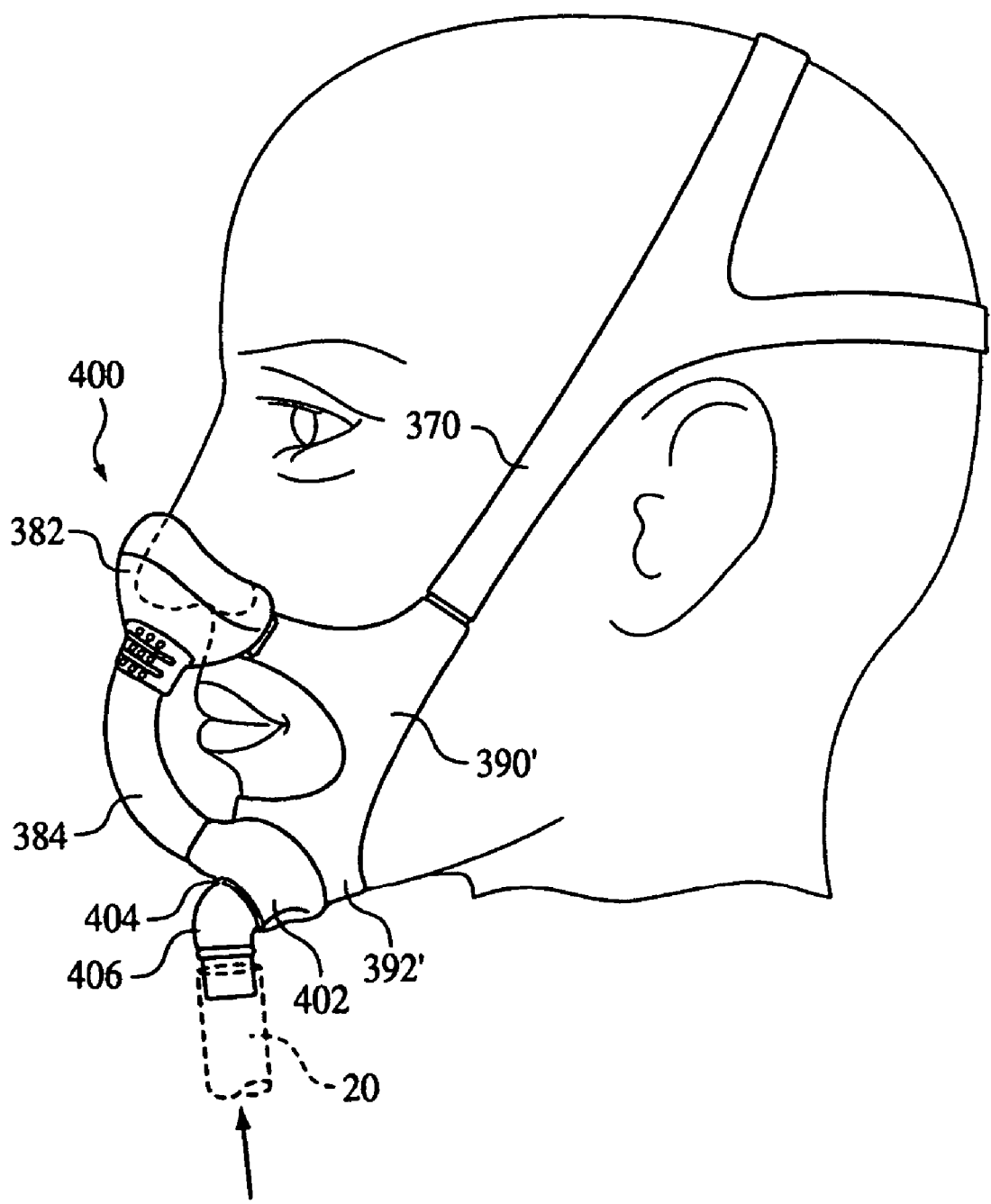
FIG. 42 is a side view of an eleventh embodiment of a patient interface assembly according to the principles of the present invention.

FIG. 42 illustrates an eleventh embodiment of a patient interface assembly 400 according to the principles of the present invention that is similar to patient interface assembly 380. The primary difference between interface assembly 400 and interface assembly 380 is that patient interface assembly 400 includes a swivel connection 402 provided on portion 392' of chin support assembly 390' as the conduit coupling structure. Swivel connection 402 is a relatively rigid member having a patient circuit connection port 404 to which the patient circuit is attached. In the illustrated embodiment, an elbow coupling 406 is provided to couple the patient circuit to portion 404. Of course, this elbow coupling can be eliminated. Conduit 384 communicates gas from swivel connection 402 to patient interface 382.

Figure 44:
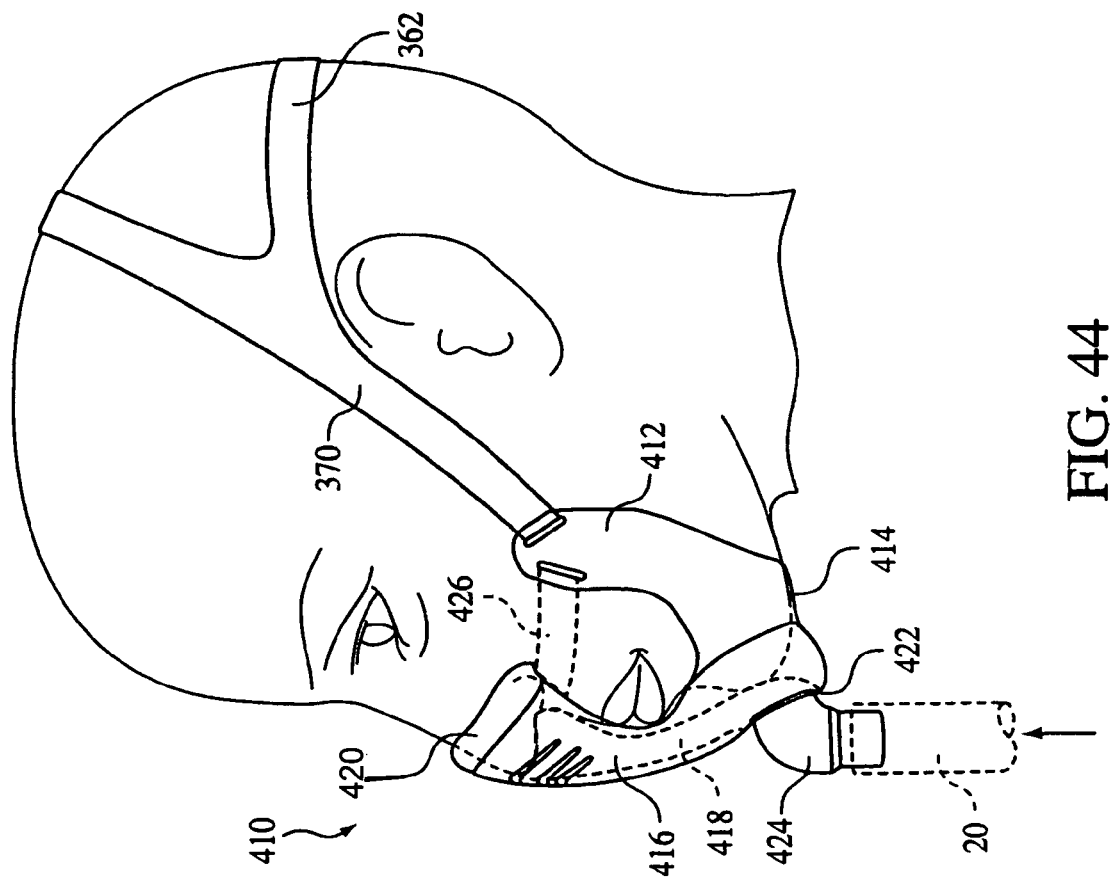
FIG. 44 is a side view of the patient interface assembly of FIG. 43.
Figure 43:
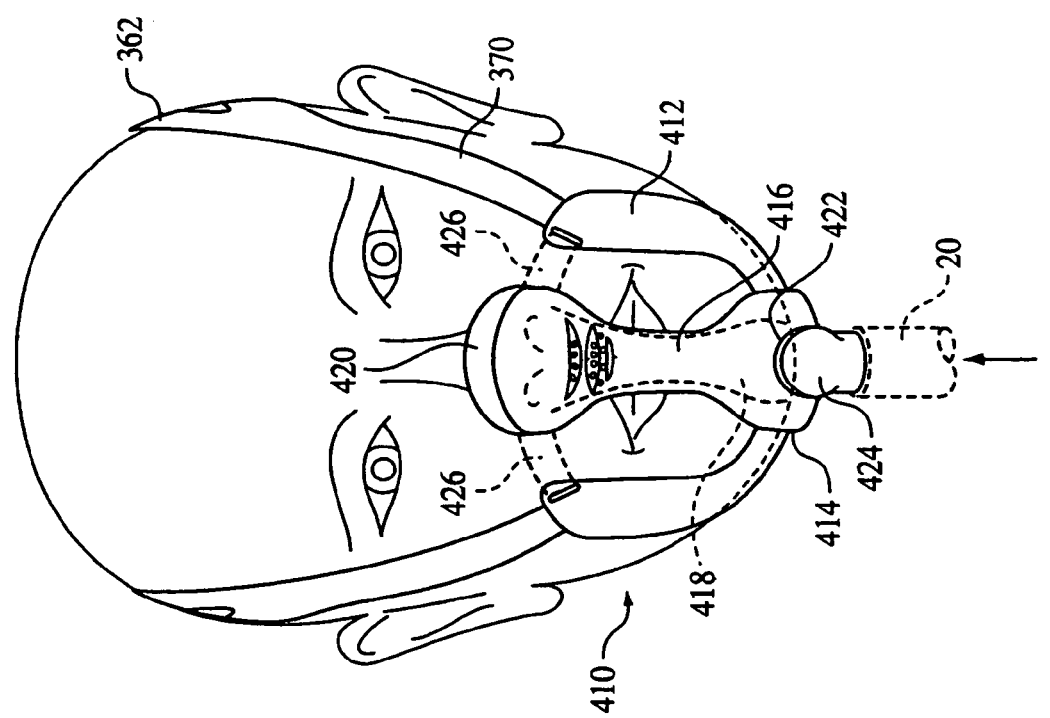
FIG. 43 is a front view of a twelfth embodiment of a patient interface assembly according to the principles of the present invention.

A twelfth embodiment of a patient interface assembly 410 according to the principles of the present invention is shown in FIGS. 43 and 44. Patient interface assembly 410 includes a chin support assembly 412 that is held on the patient by means of headgear assembly 362. Chin support assembly 412 is a relative rigid U-shaped structure contoured to correspond to the lower portion of the user's face. In particular, chin support assembly 412 includes a portion 414 that is disposed under the user's mandible to provide a relatively stable platform for mounting the patient interface portion on the patient. The central opening of the U-shape leaves the patient's mouth and nose exposed.

A rigid support 416 is coupled to portion 414 of chin support assembly 412 such that the rigid support is aligned with a centerline of the patient. A flexible conduit 418 is provided in support 416 to communicate a flow of gas from patient circuit 20 to a cushion 420 disposed at an end portion of support 416. Thus, support 416 and cushion 420 effectively act as the patient interface. A patient interface coupling port 422 is provided in support 416 to couple the patient circuit to conduit 418 such that patient circuit can rotate relative to support 416. In the illustrated embodiment, an elbow coupling 424 is provided to couple the patient circuit to the coupling port. Of course, the elbow coupling is not required.

The present invention contemplates that the connection of support 416 to chin support assembly 412 should be sufficient to maintain the cushion on the airway of the patient. That is, the cantilever type attachment is sufficient to hold cushion 420 over the patient's airway. However, if additional force is needed to keep the cushion on the patient, optional cross straps 426 can be provided that connect each leg of the U-shaped support member to the free end of support 416.

Figure 46:
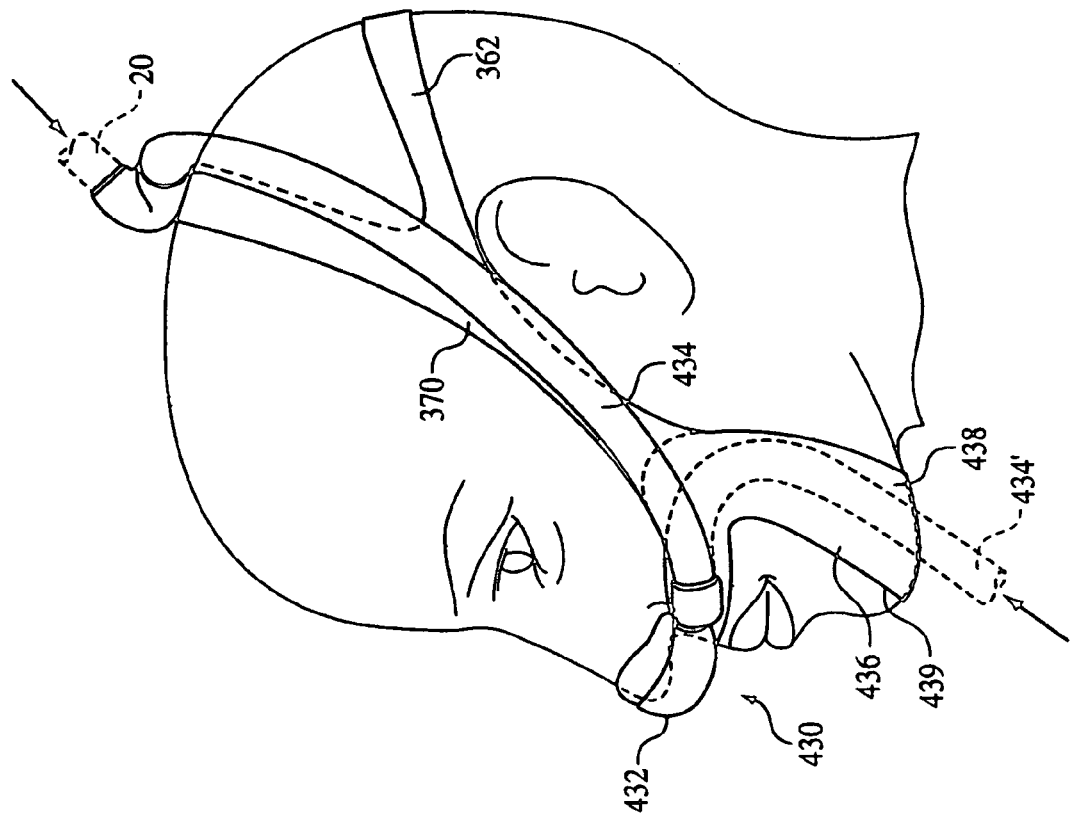
FIG. 46 is a side view of the patient interface assembly of FIG. 45.
Figure 45:
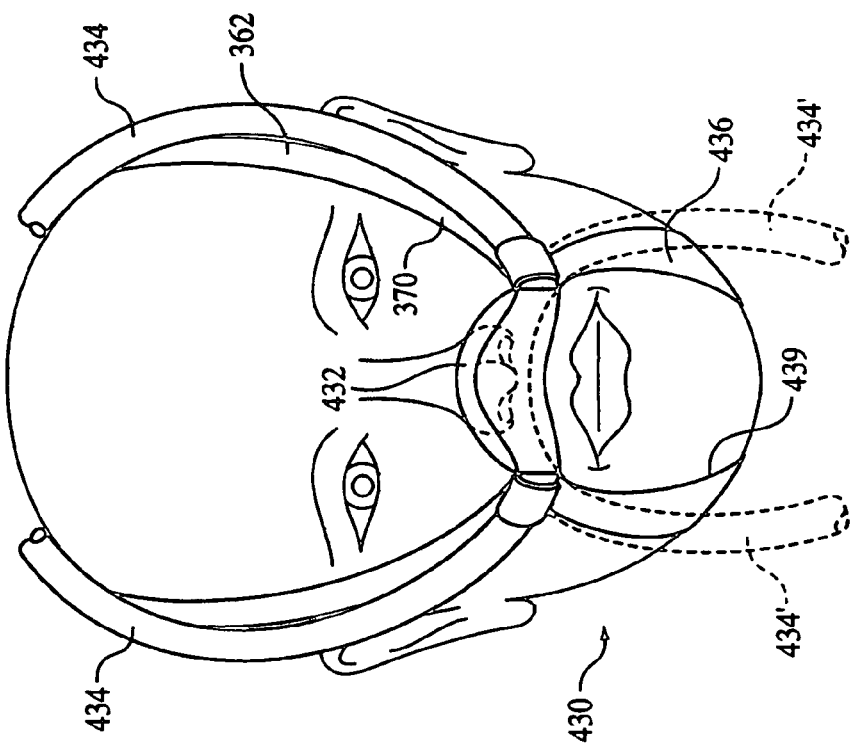
FIG. 45 is a front view of a thirteenth embodiment of a patient interface assembly according to the principles of the present invention.

FIGS. 45 and 46 illustrate a thirteenth embodiment of a patient interface assembly 430 according to the principles of the present invention. Patient interface assembly 430 includes a patient interface 432 coupled to conduits 434 that are disposed on either side of the patient's face and extend to a location above the patient's head where they attach to patient circuit 20. In the illustrated embodiment, patient interface 382 is a nasal mask type interface having ends that are rotatably coupled to conduits 434. However, the present invention contemplates that a nasal prong type interface can be used as the patient interface.

Conduits 434 are coupled to a chin support assembly 436 that loops around the patient's mouth and includes a portion 438 that is disposed under the mandible. The chin support assembly defines an opening 439 so that the mouth is exposed. Headgear straps 370 hold chin support assembly 436 on the patient's face. In an alternative configuration shown by the dashed lines in FIGS. 45 and 46, conduits 434' are disposed on either side of the patient's face and extend to a location below the patient's head where they attach to the patient circuit.

Figure 48:
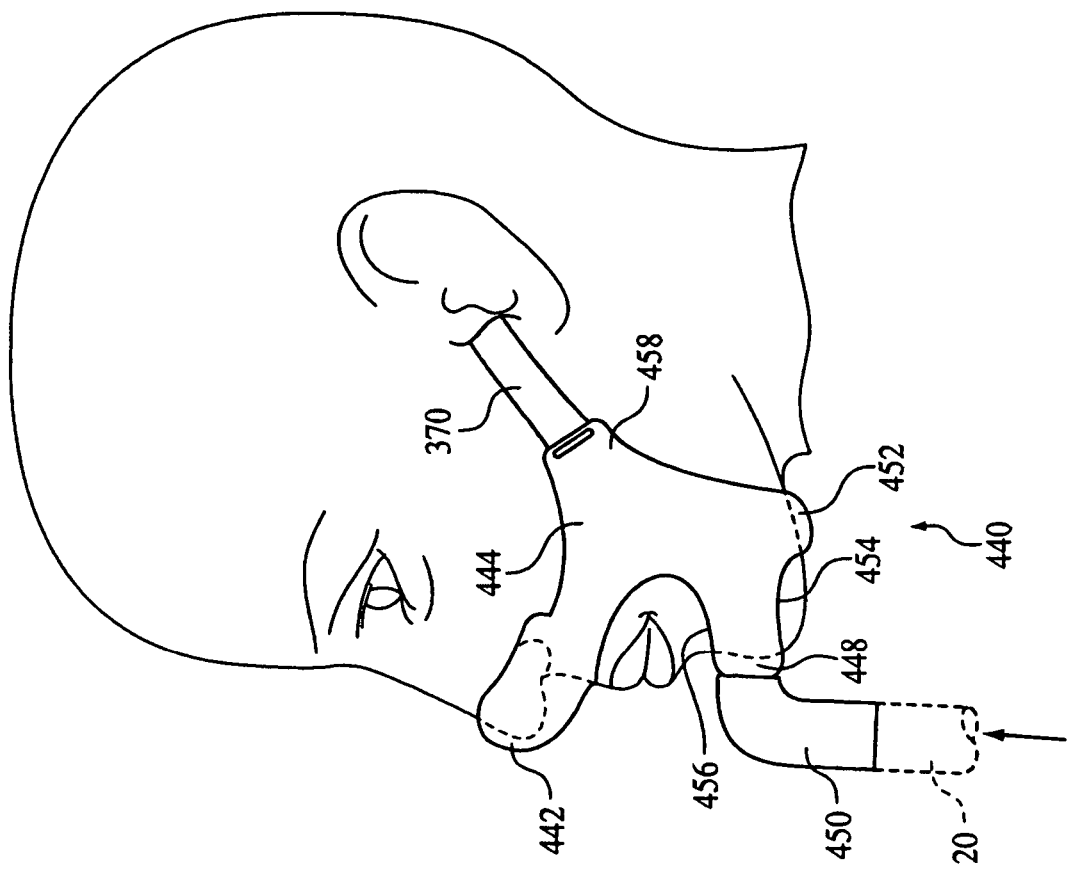
FIG. 48 is a side view of the patient interface assembly of FIG. 47.
Figure 47:
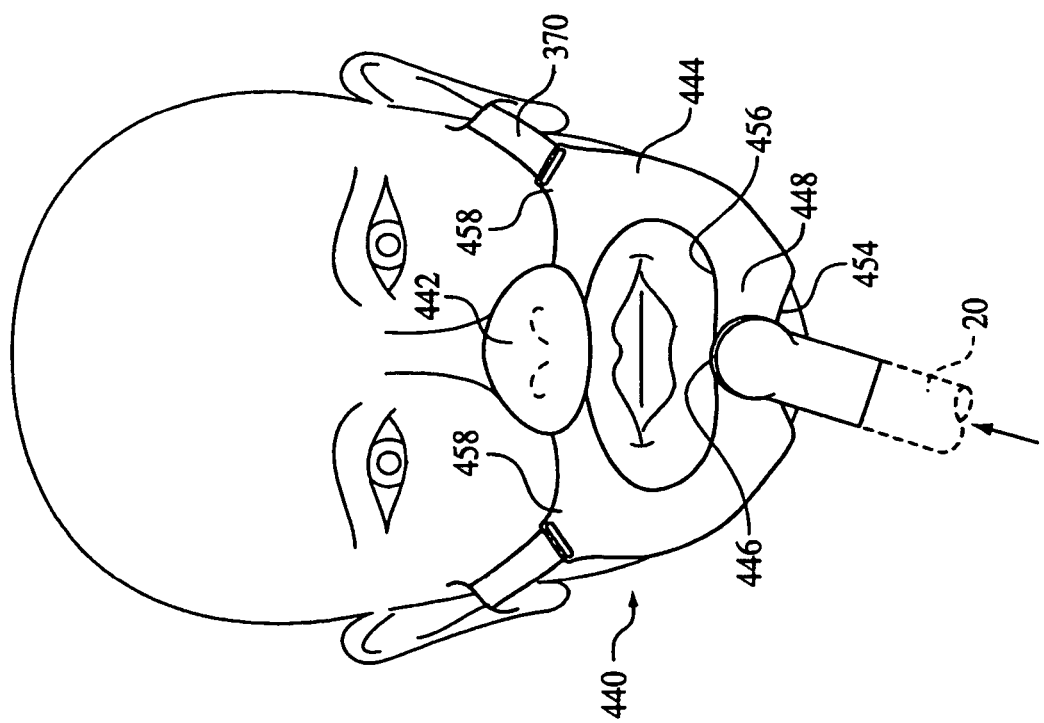
FIG. 47 is a front view of a fourteenth embodiment of a patient interface assembly according to the principles of the present invention.

FIGS. 47 and 48 illustrate a fourteenth embodiment of a patient interface assembly 440 according to the principles of the present invention. Patient interface assembly 440 includes a patient interface 442 coupled to a chin support assembly 444. Patient interface 442 corresponds to any of the interfaces discussed herein and is either fixed or rotatably attached to chin support 444.

Chin support assembly 444 is a relatively rigid structure so as to support the patient interface, contoured to correspond to the facial features of a human, and includes a sufficient degree of flexibility so that it can conform or flex to fit a variety of patients. Chin support assembly 444 is also hollow, or includes a gas carrying conduit, to communicate a flow of gas from patient circuit 20 to patient interface 442. A patient circuit coupling port 446 is provided at a frontal, lower portion 448 of chin support assembly 444 to rotatably couple the patient circuit to the chin support. In the illustrated embodiment, an elbow coupling 450 is provided to couple the patient circuit to portion 448. Of course, this elbow coupling can be eliminated.

A lower portion 452 of the chin support assembly is disposed under the patient's mandible when the patient interface assembly is being worn. Portions 448 and 452 effectively encircle the patient's chin such that the chin is disposed in an opening 454. Another opening 456 is defined in the chin support assembly so that patient's mouth is exposed. A connection piece 458 is coupled to chin support 444 to attach the headgear straps to the chin support assembly.

Figure 49:
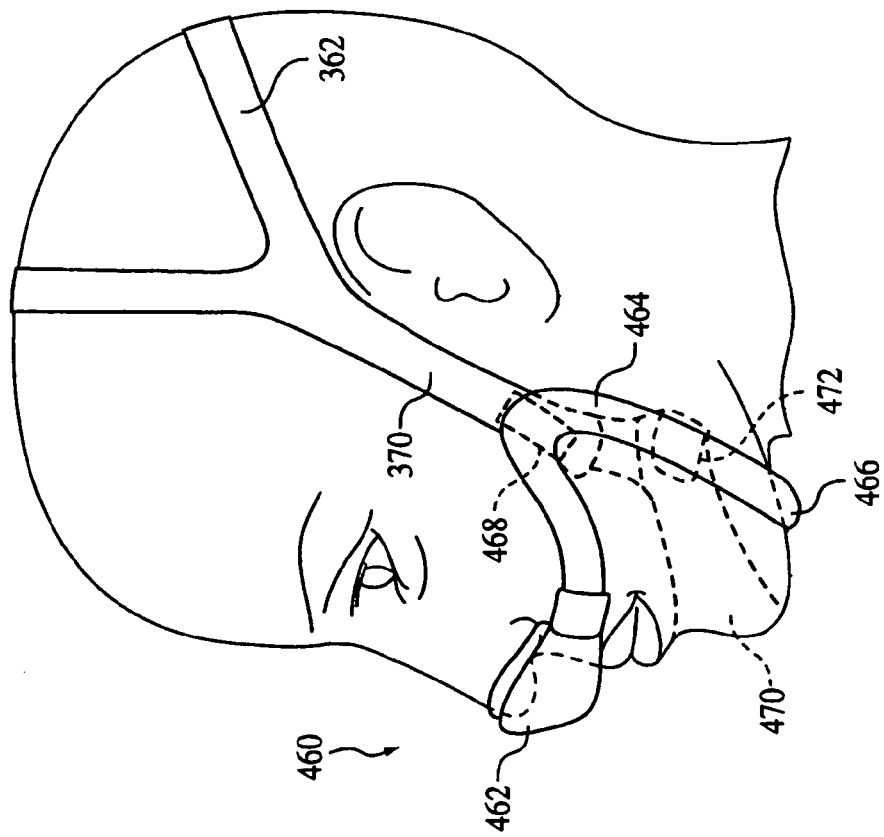
FIG. 49 is a side view of a fifteenth embodiment of a patient interface assembly according to the principles of the present invention.

A fifteenth embodiment of a patient interface assembly 460 according to the principles of the present invention is shown in FIG. 49. Patient interface assembly 460 includes a patient interface 462 coupled to a conduit 464 which functions as the chin support. Patient interface 462 corresponds to any of the interfaces discussed herein and is either fixed or rotatably attached to conduit 464. Conduit 464 includes sub-mandible portion 466 that is disposed under and engages the patient's mandible. Conduit 464 is a rigid or semi-rigid structure, at least when gas is provided by the pressure generating system, so that it effectively functions as the chin support.

Please note that FIG. 49 illustrates only one side of the patient. A mirror image of the patient interface assembly shown in FIG. 49 is also provided on the other side of the patient. Please also note that FIG. 49 does not show the connection of conduit 464 to a patient circuit. It is to be understood that this connection can be provided in an manner discussed herein or in any conventional manner.

A headgear assembly 362 is coupled to conduit 464 to hold the patient interface assembly on the patient. In the illustrated embodiment, a headgear fastener 468 is provided for connecting the conduit to headgear strap 370. It is to be understood that the headgear fastener can have any configuration suitable for connecting to the conduit, such as a loop that encircles the conduit.

The present invention contemplates providing an optional chin strap 470 that connects to conduit 464 by means of a chin strap fastener 472 for providing additional stability for the patient interface assembly. Chin strap 470 can also be attached to or integral with the headgear assembly.

Figure 50:
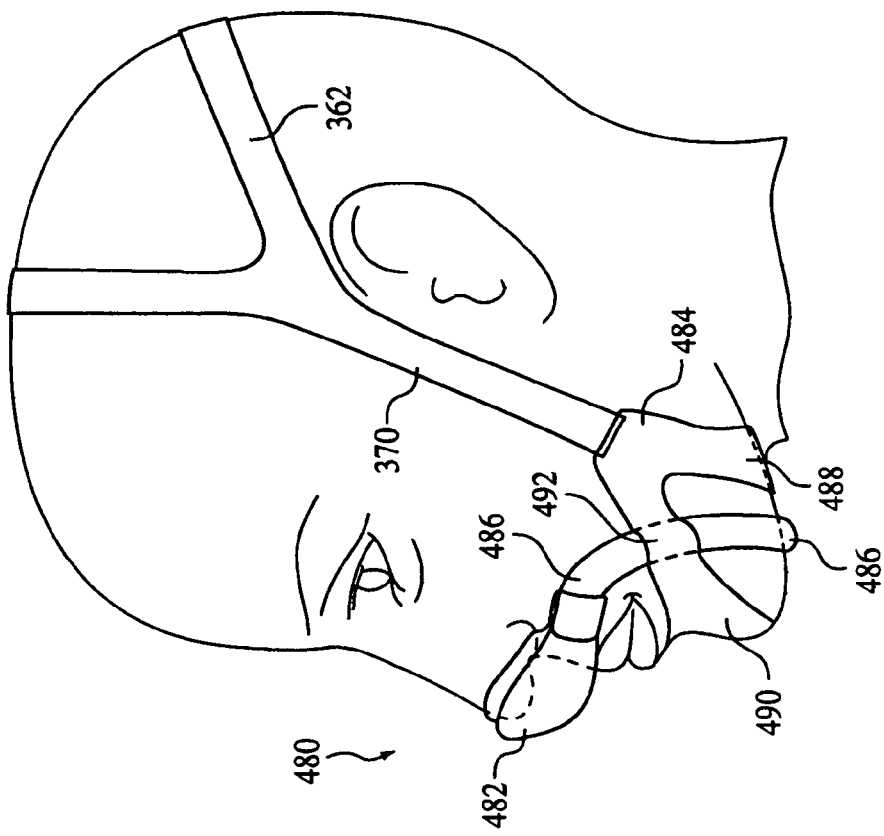
FIG. 50 is a side view of a sixteenth embodiment of a patient interface assembly according to the principles of the present invention.

FIG. 50 illustrates a sixteenth embodiment of a patient interface assembly 480 according to the principles of the present invention. Patient interface assembly 480 includes a patient interface 482 coupled to a chin support assembly 484. Patient interface 482 corresponds to any of the interfaces discussed herein and is either fixed or rotatably attached to a conduit 486.

Chin support assembly 484 includes a first portion 488 that is disposed under and engaged with the patient's mandible and a second portion 490 that contacts the user's face below the lips, generally at the chin. Conduit 486 is coupled to chin support assembly 484. In the illustrated embodiment, a conduit receiving loop 492 is provided in the chin support through which the conduit passes. The present invention also contemplates passing the conduit under the chin support assembly, i.e., between the patient and the chin support assembly.

Figure 52:
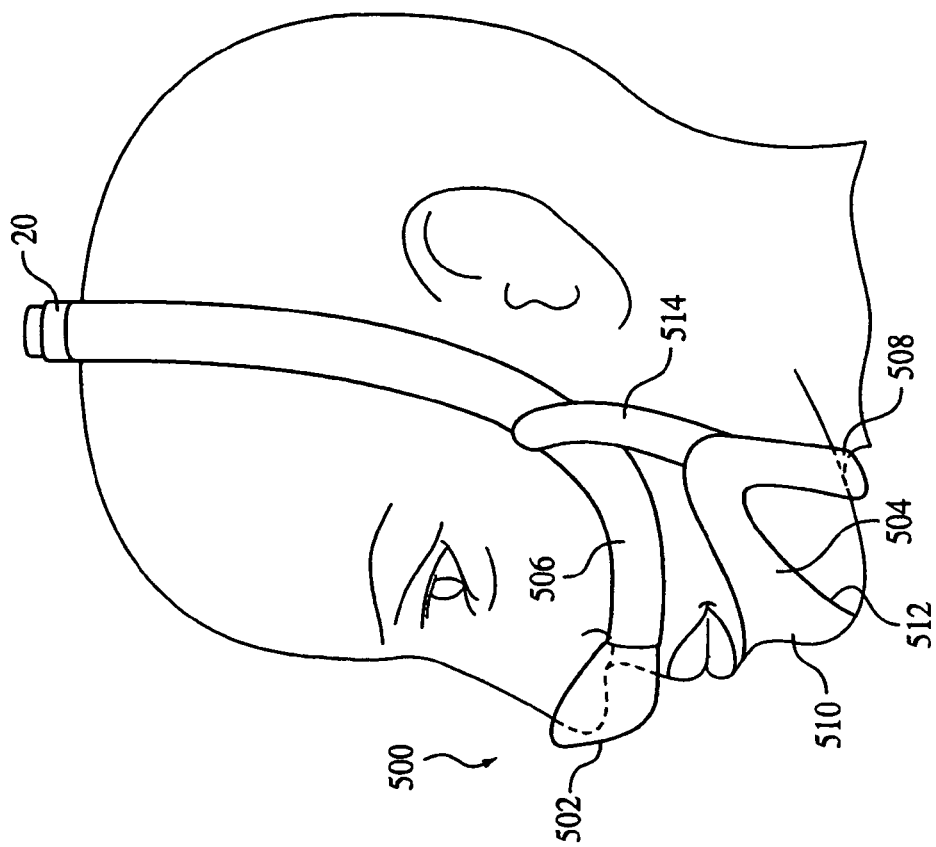
FIG. 52 is a side view of the patient interface assembly of FIG. 51.
Figure 51:
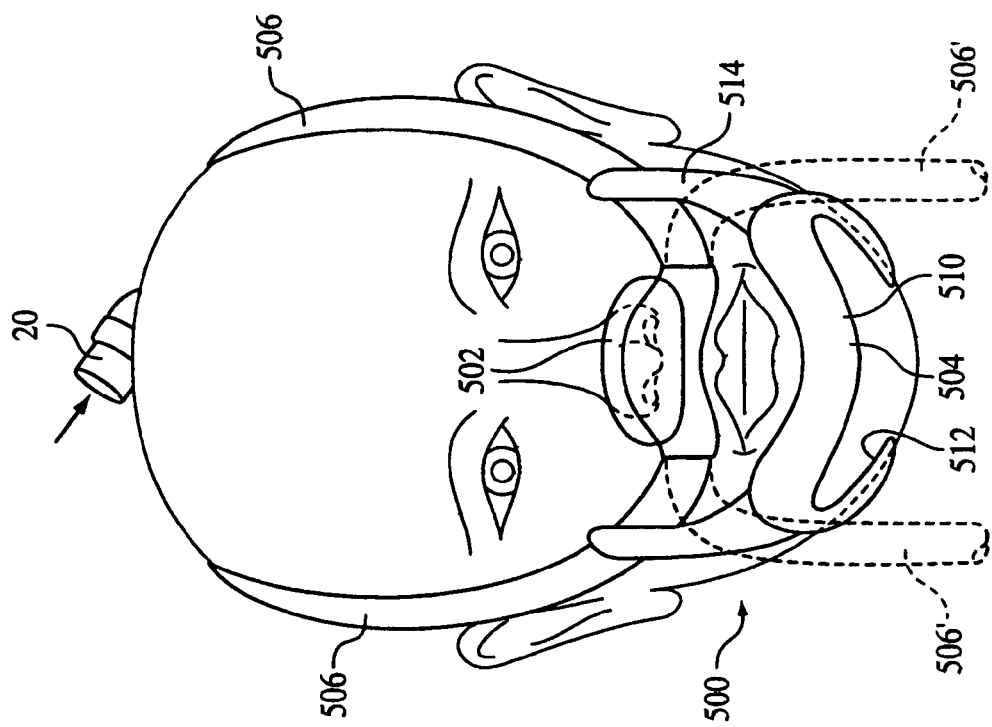
FIG. 51 is a front view of a seventeenth embodiment of a patient interface assembly according to the principles of the present invention.

FIGS. 51 and 52 illustrate a seventeenth embodiment of a patient interface assembly 500 according to the principles of the present invention. Patient interface assembly 500 includes a patient interface 502 coupled to a chin support assembly 504. Patient interface 502 corresponds to any of the interfaces discussed herein and is either fixed or rotatably attached to conduits 506, which are, in turn, attached to chin support assembly 504.

Chin support assembly 504 is a cup-like structure having a first portion 508 disposed under the mandible and a second portion 510 disposed at the front of the patient below the lips and at or above the chin. Preferably, an opening 512 is provided in the chin support assembly to minimize contact with the patient. Coupling members 514 attach chin support assembly 504 to conduits 506. In the illustrated exemplary embodiment, coupling members 514 are permanently attached to chin support assembly 504 and are selectively attached to conduits 506. For example, the present invention contemplates forming the coupling members from a strip of material, such as a fabric, having one end fixed to the chin support. The strip of material is sized and configured to loop over (and around, if desired) the conduits. The free end of the strip of material is attached back onto itself or the chin support using any conventional technique, such as a hook and loop type fastener.

In one embodiment, conduits 506 extend up from the patient interface device to a location proximate to the top of the patient's head where it attaches to patient circuit 20. An alternative embodiment of the present invention, which is shown by dashed lines in FIG. 51, contemplates extending conduit 506' to a location below the patient, where it attaches to the patient circuit. If this alternative embodiment is used, a headgear assembly, similar to that discussed herein, should be used to couple the chin support to the patient. For example, the present invention contemplates attaching conduit 506' to the chin support assembly and attaching the chin support assembly to a headgear via coupling members 514.

Figure 53:
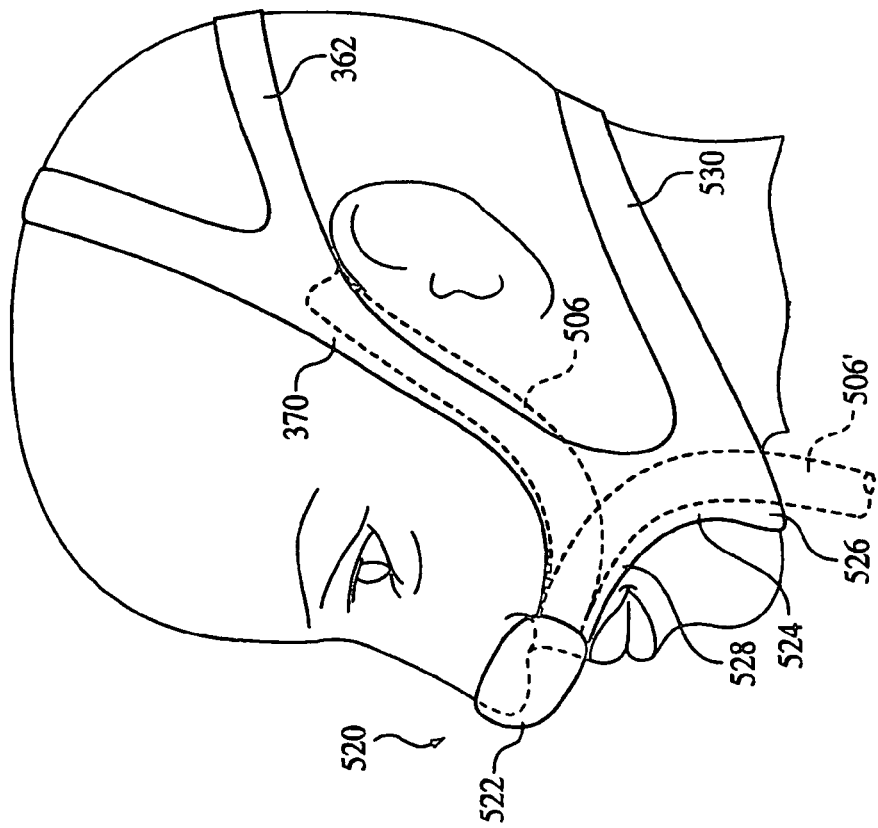
FIG. 53 is a side view of an eighteenth embodiment of a patient interface assembly according to the principles of the present invention.

An eighteenth embodiment of a patient interface assembly 520 according to the principles of the present invention is shown in FIG. 53. Patient interface assembly 520 includes a patient interface 522 coupled to a chin support assembly 524. Patient interface 502 corresponds to any of the interfaces discussed herein and is either fixed or rotatably attached to conduits 506 or 506', which are, in turn, attached to chin support assembly 524. Conduits 506 and 506' show two alternative arrangements for locating the gas delivery conduit on the patient. In both embodiments, the conduits are secured to the chin support in any conventional fashion. The patient interface is connected to the one end of the conduit in either a fixed or rotatable fashion, and the other end of the conduit is coupled to the patient circuit.

It should be understood that FIG. 53 illustrates only one side of the patient. A mirror image of the patient interface assembly shown in this figure is also provided on the other side of the patient. The connection of the conduit to a patient circuit is also not show. It is to be understood, however, that this connection can be provided in an manner discussed herein or in any conventional manner.

Chin support assembly 524 is attached to a headgear assembly 362 and includes a first portion 526 that is disposed under the mandible and a second portion 528 that extends from the first portion to the patient interface. The chin support assembly also includes a neck strap 530 that extends around the patient, generally at the neck. This embodiment leaves a substantial portion of the chin exposed and uses the rear of the jaw and neck to provide stability for the patient interface assembly.

Figure 54:
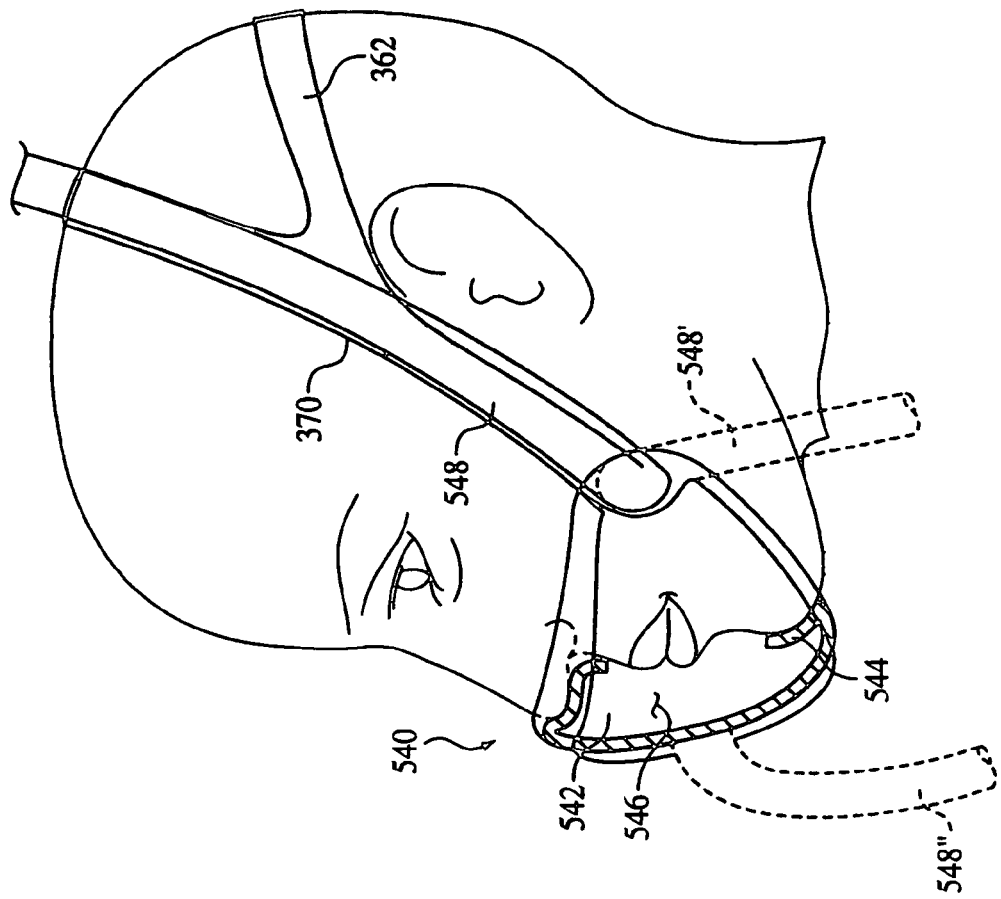
FIG. 54 is a side view of a nineteenth embodiment of a patient interface assembly according to the principles of the present invention.

A nineteenth embodiment of a patient interface assembly 540 according to the principles of the present invention is shown in FIG. 54. In this embodiment, a patient interface 542 provides the function of the chin support, in that a portion of the patient interface is disposed at the chin, under the mandible, or at both locations. For example, portion 544 of the seal or cushion portion of the patient interface contacts the user's chin. This portion is shown in section in FIG. 54. An interior chamber 546 is defined in the patient interface, and a conduit 548 communicates with chamber 546. A headgear assembly 362 is coupled to patient interface 542 to hold the patient interface assembly on the patient. The patient interface shown in this embodiment is a nasal/oral mask in that it encompasses the nose and mouth. It is to be understood that the patient interface can be a oral-only mask that encompasses only the mouth.

It should again be understood that FIG. 54 illustrates only one side of the patient interface assembly. A mirror image of the patient interface assembly shown in this figure is also provided on the other side of the patient. Also, the connection of the conduit to a patient circuit is also not shown. It is to be understood, however, that this connection can be provided in an manner discussed herein or in any conventional manner.

In the illustrated embodiment, conduits 548 extend up from the patient interface device to a location proximate to the top of the patient's head where it attaches to patient circuit 20. Conduit 548 can be attached to headgear assembly 362, if desired. An alternative embodiment of the present invention, which is shown by dashed lines in FIG. 54, contemplates extending conduit 548' to a location below the patient, where it attaches to the patient circuit. Yet another alternative embodiment of the present invention, contemplates attaching conduit 548" to the front of the patient interface 542, preferably in a rotatable fashion.

Figure 56:
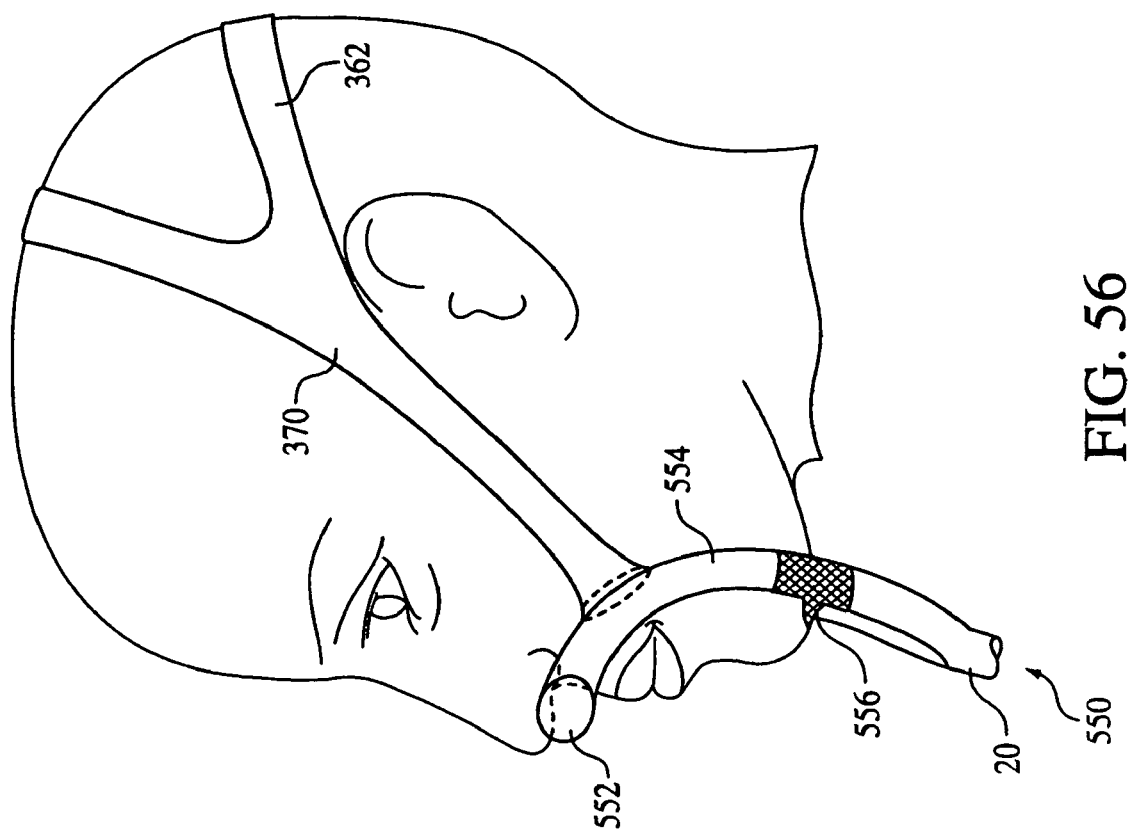
FIG. 56 is a side view of the patient interface assembly of FIG. 55.
Figure 55:
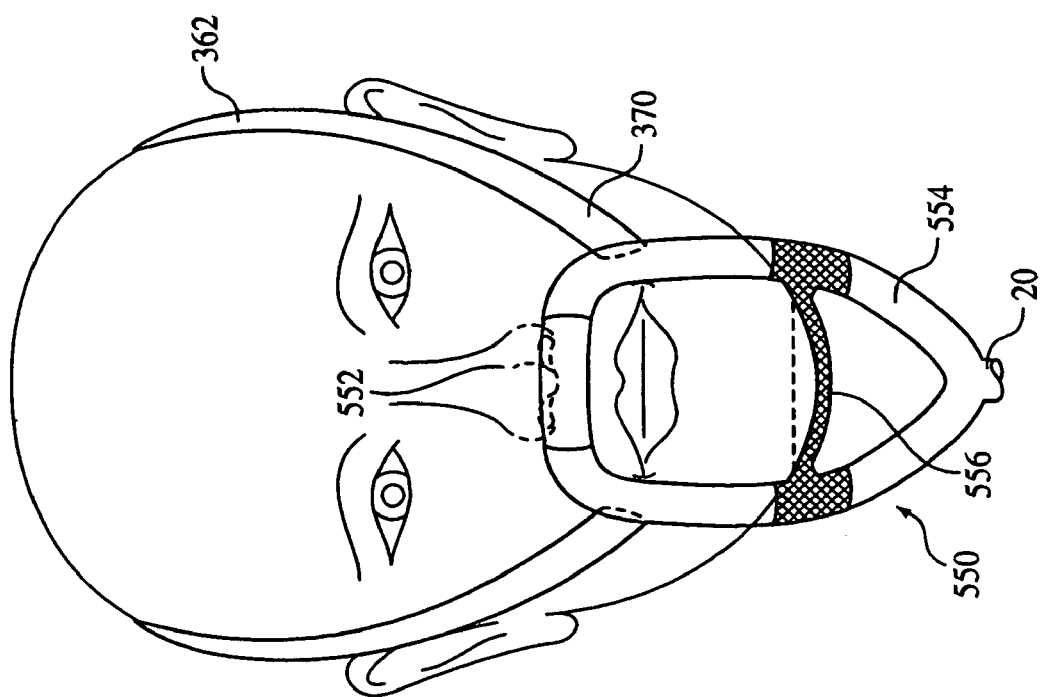
FIG. 55 is a front view of a twentieth embodiment of a patient interface assembly according to the principles of the present invention.

FIGS. 55 and 56 illustrate a twentieth embodiment of a patient interface assembly 550 according to the principles of the present invention. Patient interface assembly 550 includes a patient interface 552 coupled to conduits 554. Patient interface 552 corresponds to any of the interfaces discussed herein and is either fixed or rotatably attached to conduits 554. A chin support assembly 556 is coupled to conduits 554 such that a portion of the chin support is disposed under the patient's mandible. Chin support assembly 556 is preferably a flexible structure, for example, a cloth material that is attached to conduits 554 in any conventional manner. The patient interface assembly is held on the patient by means of headgear assembly 362. More specifically, headgear straps 370 are coupled to conduits 554 in any conventional fashion.

Figure 58:
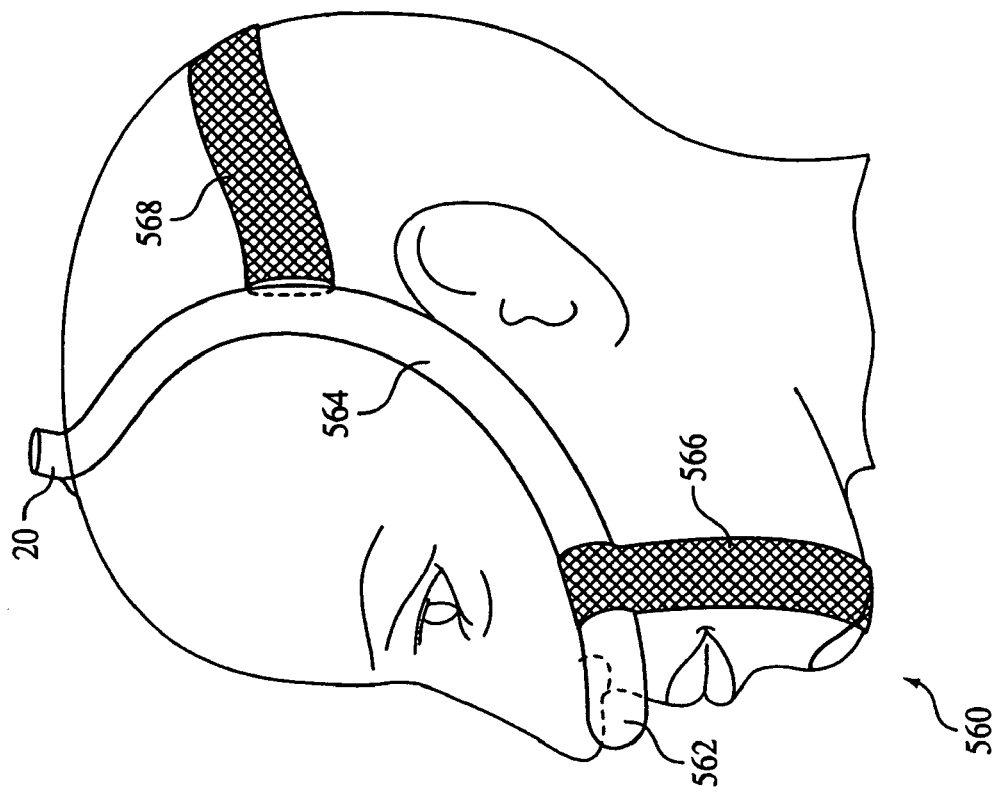
FIG. 58 is a side view of the patient interface assembly of FIG. 57.
Figure 57:
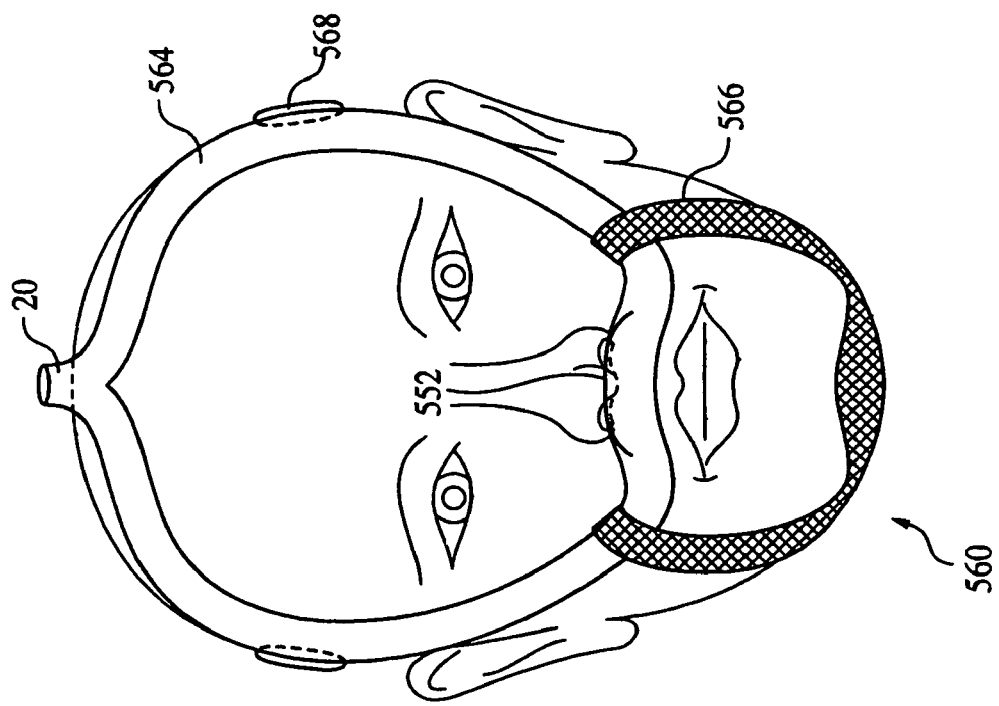
FIG. 57 is a front view of a twenty-first embodiment of a patient interface assembly according to the principles of the present invention.

FIGS. 57 and 58 illustrate a twenty-first embodiment of a patient interface assembly 560 according to the principles of the present invention. Patient interface assembly 560 includes a patient interface 562 coupled to conduits 564, which are connected to patient circuit 20. A chin support assembly 566 is coupled to conduits 546 such that the mouth remains exposed and a portion of the chin support passes under the mandible. Chin support assembly 566 is preferably formed from a flexible material, such as cloth or fabric. A head strap 568 that connects to conduits 546 across the back of the patient's head is provided for facilitating the attachment of the conduits on the user's head.

Figure 59:
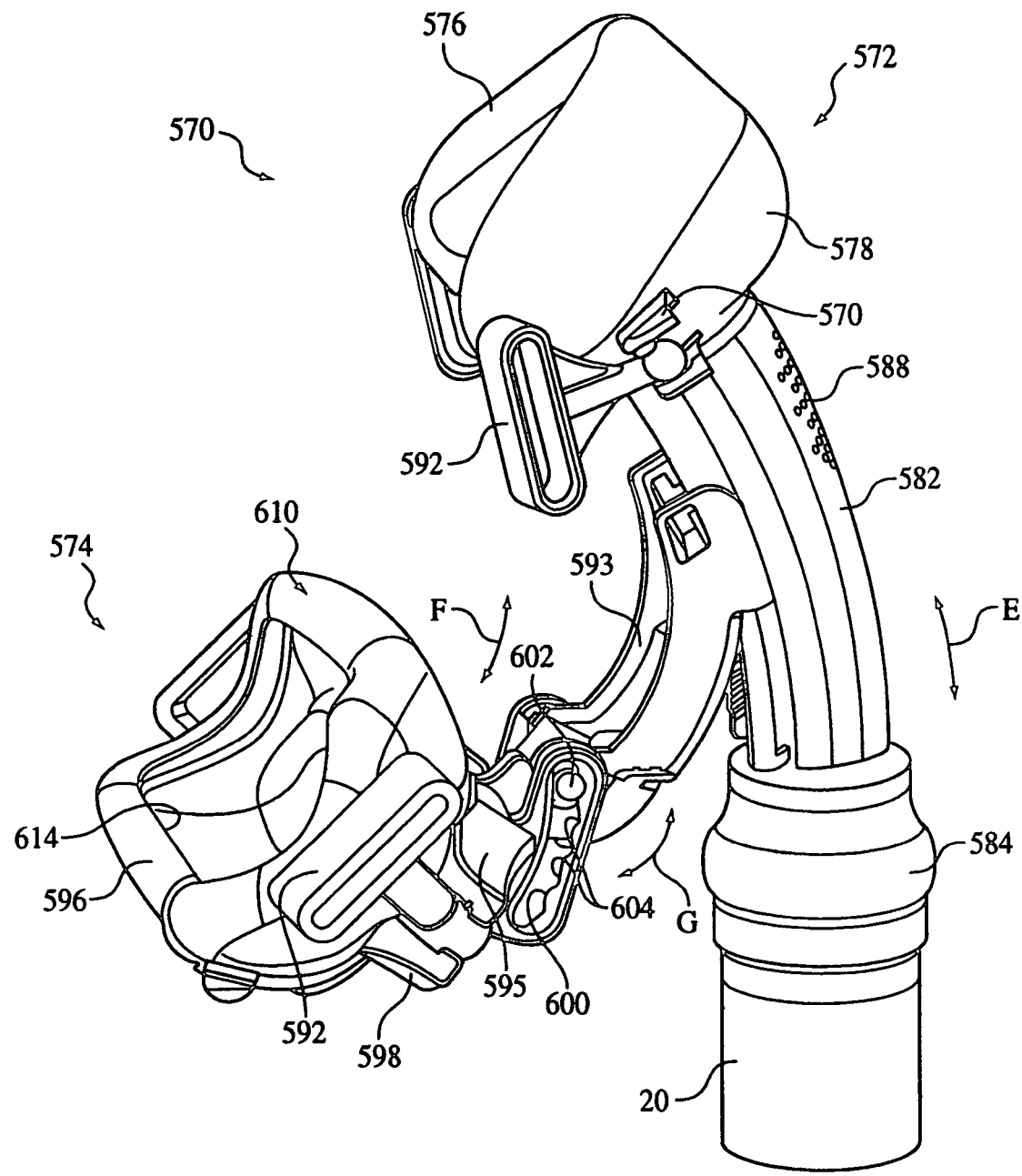
FIG. 59 is a side perspective view of a twenty-second embodiment of a patient interface assembly according to the principles of the present invention.
Figure 60:
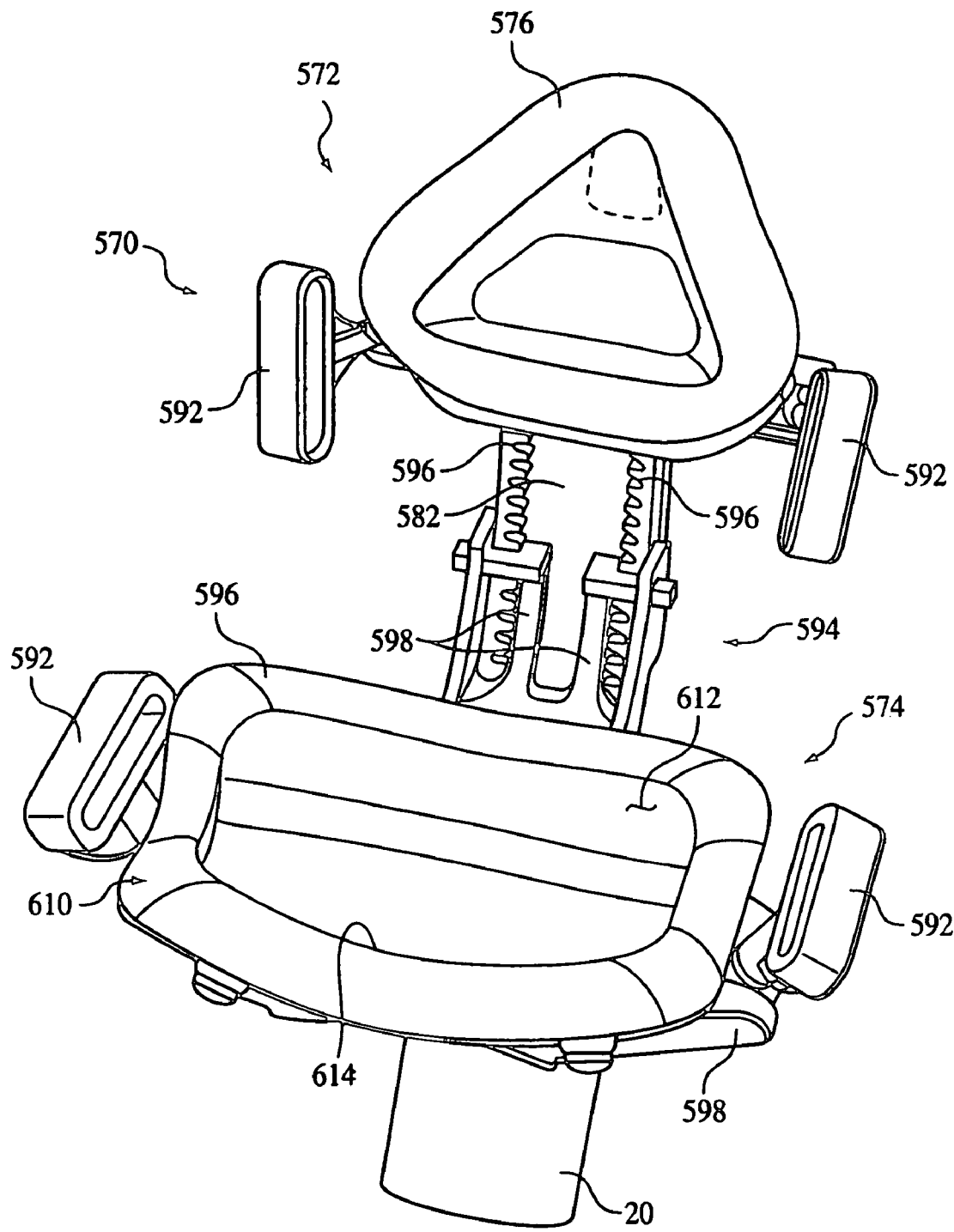
FIG. 60 is a rear view of the patient interface assembly of FIG. 59.

FIGS. 59 and 60 illustrate a twenty-second embodiment of a patient interface assembly 570 according to the principles of the present invention. Patient interface assembly 570 is similar in many respect to patient interface assembly 270 shown in FIGS. 32 and 33. The two main differences between patient interface assembly 570 and patient interface assembly 270 are the configuration for an arm 582 and the configuration for a chin pad 596.

Patient interface assembly 570 includes a patient interface 572 and a chin support assembly 574. Patient interface 572 also includes a cushion 576 and a cushion support 578. As in the previous embodiments, the cushion support and cushion can have a variety of different configurations, only one of which is shown in the figures. Arm 582 couples to patient circuit 20 to the patient interface via a coupling member 584.

In the illustrated embodiment, arm 582 is a curved member form as a single, arcuate tube, thereby minimizing changes in direction for the flow of gas to the patient. It is to be understood that the present invention contemplates connecting the patent circuit to arm 582 using any suitable coupling technique, i.e., any suitable structure for coupling member 584. Gas from the pressure generating system is provided to a cavity defined by cushion 576 via patient circuit 20 and through the hollow interior of arm 582.

An exhaust element 588 is also provided on arm 582. Exhaust element 588 and headgear mounting elements 590 are provided on cushion support 578. In this embodiment, the exhaust elements include a plurality of holes provided in arm 582. FIGS. 59 and 60 show headgear connectors 592 connected to the headgear mounting elements 590. Headgear connectors 592 can have any suitable configuration. In addition, any conventional configuration for attaching the headgear strap to the cushion support 278 are contemplated by the present invention, not just that shown in the figures.

In the illustrated embodiment, cushion 576 is a nasal mask type interface and rests against the underside of the patient's nose. As with cushion 276, cushion 576 is formed from any suitable material, such as foam, silicone, rubber, gel, or any combination thereof, and is can be detachable from cushion support 578 so that it can be cleaned, or so that different sizes of cushions can be used on one size of cushion support. Of course, the present invention contemplates that cushion 576 (or 276) can have any other configuration.

Chin support assembly 574 includes a chin support arm 593 and a chin support bracket 595. Chin support bracket 595 is a substantially rigid member that supports chin pad 596. Chin support assembly 574 includes headgear mounting elements 598 provided on chin support bracket 595 that are similar to headgear mounting elements 590. It is to be understood that the present invention contemplates using any conventional connection assembly for attaching the headgear straps to the chin support assembly.

Chin support arm 593 is adjustably coupled to arm 582 so that chin support assembly 574 is adjustable relative to cushion support 578. In this illustrated exemplary embodiment, a ratchet mechanism 594 couples arms 582 and 593 so that the relative position of these two member can be set to discrete locations. In particular, arm 582 includes a plurality of teeth 596 disposed on arm 582. A ratchet arm (or plurality of ratchet arm) 598 are coupled to arm 593 so as to selectively engage the teeth. Arm 593 is capable of moving along an axis or curve, as indicated by arrow E, relative to arm 582.

Chin support bracket 595 is adjustably connected to an end portion of chin support arm 293 via a slide-and-rotate arrangement. This is accomplished by providing a slot 600 on chin support bracket 595 and a pin 602 on arm 593 that is provided in slot 600. Slot 600 includes detents 604 to allow the pin to be provided and held at discrete locations along the length of the slow. This configurations allow chin support bracket 595 to both slide and rotate with respect to chin support arm 593. It can be appreciated that this configuration for the chin support bracket provides three independent positional adjustments for the chin support bracket relative to cushion support 578. First, the chin support bracket is capable of moving in a lengthwise direction, as indicated by arrow E. Second, the chin support bracket moves in a sliding direction, as indicated by arrow F. Finally, chin support bracket 595 pivots about pin 602, as indicated by arrow G.

Chin pad 596, like chin pad 296, can have any one of a variety of configurations. On such configuration is shown in U.S. patent application Ser. No. 10/953,642, the contents of which are incorporated herein by reference. Any suitable configuration is shown in FIGS. 59 and 60. In this embodiment, the chin pad is formed form a pliable, resilient material, such as silicone, and includes a patient contacting surface 610 that is shaped to correspond, in general, to the shape of a human chin. Chin pad 596 also includes a hollow interior, i.e., a chamber 612 is defined in the interior of the chin pad. In the illustrated exemplary embodiment, chamber 612 is exposed by means of an opening 614 provided in the patient contacting side of the chin pad.

In the illustrated embodiment, opening 614 has a shape that generally matches an outer edge or perimeter of the chin pad. It is to be understood, however, that opening 614 can have a variety of other configurations. In addition, multiple opening can be provided to chamber 612. Moreover, multiple chambers can be provided in the chin pad by providing walls within the interior of chin pad to define the separate chambers. Such separate chambers or areas can be completely isolated from other portions of the interior of the chin pad or can be connected. The walls of the chin pad provide the cushion-type support for the user's chin.

Figure 61:
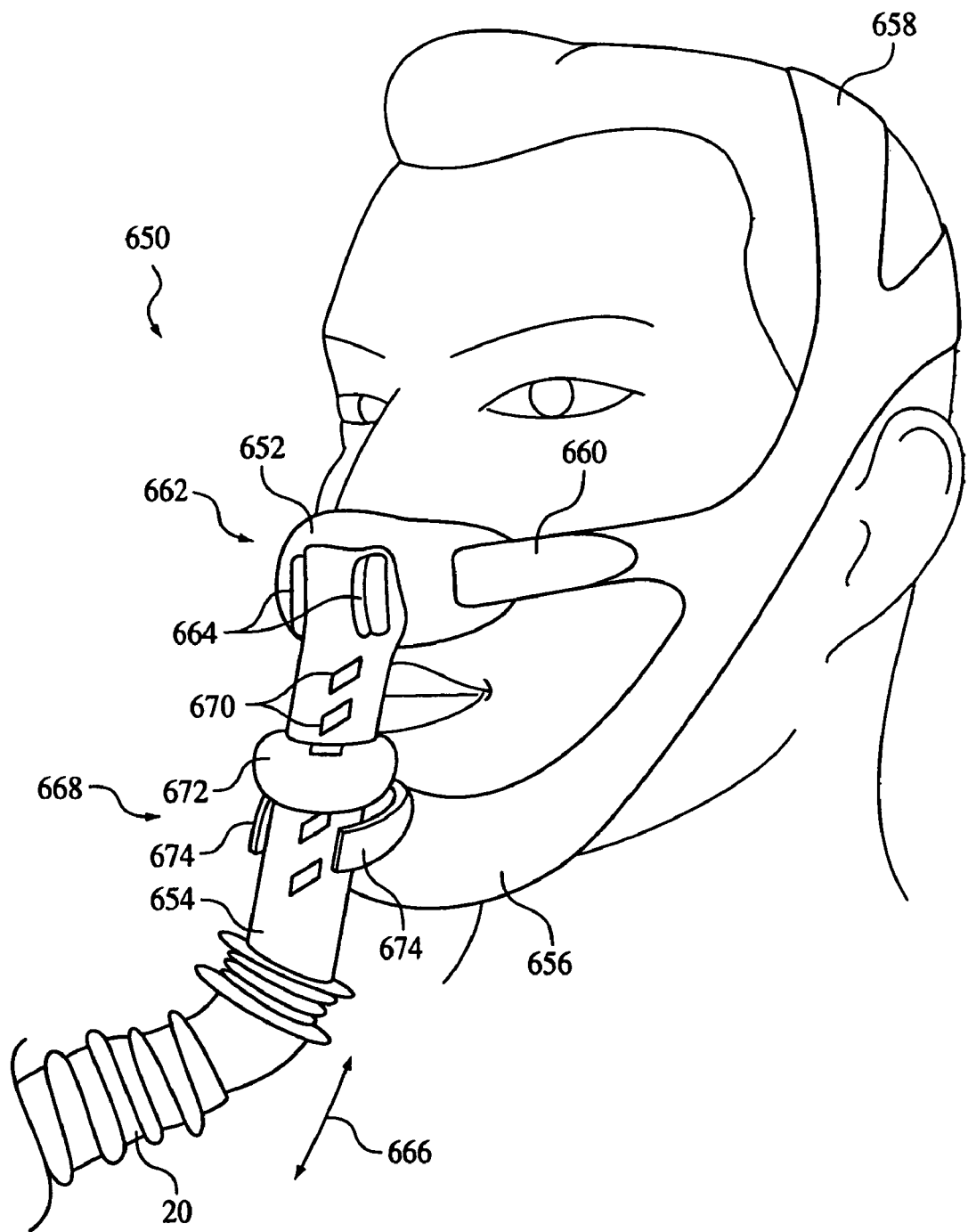
FIG. 61 is a side perspective view of a twenty-third embodiment of a patient interface assembly according to the principles of the present invention.

FIG. 61 illustrates a twenty-third embodiment of a patient interface assembly 650 according to the principles of the present invention. Patient interface assembly 650 includes a patient interface 652 coupled to a conduit 654 that is provided at the end of patient circuit 20. Patient interface 652 includes a cushion and may include a faceplate, i.e., a rigid or semi-rigid member that supports the cushion. Conduit 654 is a relatively rigid conduit that is coupled to the patient circuit via an elbow, ball and socket, or any suitable connecting member. Conduit 654 is attached to the patient via a chin support assembly 656 that overlies the user's chin and is connected about the head via a headgear 658.

Patient interface 652 is also coupled to headgear 658 using connecting members 660. In the illustrated embodiment, connecting members 660 are straps that tread through slots (not shown) provided on the patient interface. The length of the straps is made adjustable by providing a hook and loop fastener, or any suitable fastener, to attached the free end at a selected location along the length of the strap. Of course, the present invention contemplates that any suitable mechanism can be used to couple the patient interface to the headgear. In an exemplary embodiment, the coupling member should allow patient interface 652 to be detached from headgear 658, for example by unthreading the straps from the slots provided on the patient interface.

The present invention also contemplates that patient interface 652 and conduit 654 are detachable so that the conduit can be detached from the patient interface while leaving the patient interface in place on the user. To accomplish this function, a quick release mechanism 662 is provided on the distal end of conduit 654. Quick release mechanism 662 can be any device, assembly, or arrangement that allows the end of conduit 654 to be releasably connected to patient interface 652. For example, the quick release mechanism shown in FIG. 23 can be used for this purpose. In the embodiment shown in FIG. 61, a pair of tabs 664 are provided to unlock or lock the conduit to the patient interface manually. Obviously, when connected, the lumen defined in conduit 654 should be in fluid communication with the interior or patient interface 652.

Another feature of the patient interface assembly 650 is the ability to adjust the position of conduit 654 relative to chin support 656, as indicated by arrow 666. This feature of the present invention allows the distance, i.e., the length of conduit 652, between a chin portion 668 of chin support 656 and patient interface 652 to be controlled and adjusted to accommodate patients of different sizes. The patient interface assembly illustrated in FIG. 61 includes an adjustment mechanism 668 that enables this length adjustment. In the illustrated exemplary embodiment, adjustment assembly 668 includes threads 670 provided on conduit 654 and a movable member 672. Moveable member 672 includes threads (not shown) that engage threads 670 such that rotating the moveable member around the conduit moves the moveable member up or down the conduit. This provides an infinite degree of adjustment between the moveable member and the locking mechanism. In the illustrated embodiment, locking mechanism 674 includes a pair of arms that frictionally engage the moving member so as to selectively attaché the moveable member to the locking mechanism.

The engagement between the locking mechanism and the moveable member can be fixed, so that there is no relative movement between these two component when locked together, or moveable, so that the locking member (and the conduit) rotate relative to the chin support even when the moveable member is locked into a locking mechanism. Providing the moveable member and locking mechanism with a ball-and-socket configuration is one exemplary way to accomplish this latter function.

It can thus be appreciated that the patient interface assembly shown in FIG. 61, by including quick release mechanisms 662 and 668, allows the conduit to be removed from the patient, leaving the chin support and the patient interface on the patient. This gives be patient the ability to quickly and easily detach himself or herself from the pressure support system, for example, to use the restroom during the night, and reattach himself or herself to the pressure support system without changing any of the adjustable components of the patient interface assembly.

Figure 62:
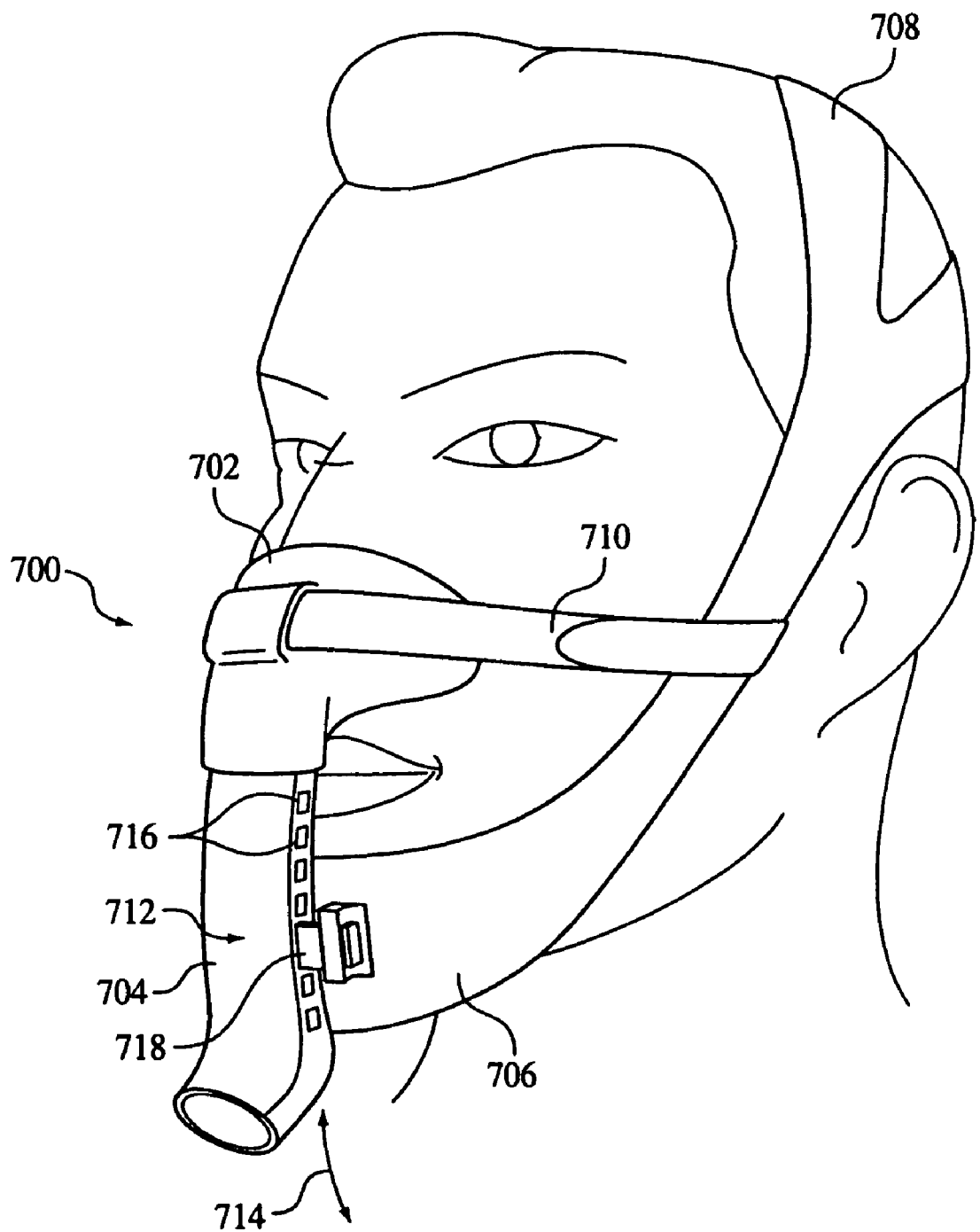
FIG. 62 is a side perspective view of a twenty-forth embodiment of a patient interface assembly according to the principles of the present invention.

FIG. 62 illustrates a twenty-forth embodiment of a patient interface assembly 700 according to the principles of the present invention. Patient interface assembly 700 includes a patient interface 702 coupled to a conduit 704. Conduit 704 is coupled to the end of a patient circuit (not shown) using any conventional coupling technique, including any technique discussed above. Patient interface 702 includes a cushion and may include a faceplate, i.e., a rigid or semi-rigid member that supports the cushion. Conduit 704 is a relatively rigid conduit that is attached to the patient via a chin support assembly 706 that overlies the user's chin and is connected about the head via a headgear 708.

In the illustrated embodiment, patient interface assembly 700 includes an connecting member 710 that connects patient interface 702 to chin support assembly 706/headgear 708. It is to be understood, however, that this connecting member is optional. If eliminated, the patient interface is held against the airway of the patient by conduit 704. In the illustrated embodiment, connecting member 710 is an adjustable length strap that passes through a slot in the patient interface and connects to the chin support assembly/headgear on each side of the patient. It is to be understood that any device for securing the patient interface to the chin support assembly/headgear, which includes a detachable and/or adjustably connection.

Patient interface assembly 700 further includes an adjustment mechanism 712 that connects conduit 704 to chin support 706 and provides the ability of the conduit to be moved relative to the chin support, as indicated by arrow 714 over a plurality of discrete positions. In the illustrated exemplary embodiment, adjustment assembly 712 includes slots 716 provided on conduit 704 and an engaging member 718 that engage the slots. The slots and engaging member can have any one of a number of different configurations, only one example of which is shown in FIG. 62. In this embodiment, the slots are provided on each side of the conduit and an engaging member is disposed on the chin support also on each side of the conduit to grapple to the conduit via the slots. Any suitable release mechanism can be used to maintain the engaging member in an engaged relationship with the conduit. It should be noted that the one portion of the adjustment assembly is shown in FIG. 62, the other portion being on the other side of conduit 704.

By disengaging conduit 708 from chin support 706 via adjustment mechanism 712, the patient interface and conduit can be easily and quickly decoupled from the patient interface assembly, leaving the chin support and headgear on the patient. Likewise, the patient interface and conduit can also be easily reattached to the chin support, without changing any of the adjustable components of the patient interface assembly so that the patient interface assembly does not need to be readjusted when it is donned by the user.

The embodiments of the invention discussed above described only a few techniques for selectively attaching the conduit to the chin support. It should be understood that other techniques for accomplishing this function are contemplated by the present invention. The conduit can be attached to the chin support such that it is fixed, i.e., does not move, or is adjustable. The position of the conduit relative to the chin support can be adjusted in discrete steps, for example, using a ratchet or that shown in FIG. 62, or it can have an infinite number of positions, using a sliding friction lock (FIGS. 40, 41) or a treaded screw (FIG. 61). The present invention also contemplates using a hook and loop adhesive type of attaching mechanism so that the conduit can be detached from the chin support, moved to a desired position, reattached to the chin support, and maintained in the new position by the hoop and loop fastener.

In the above-described embodiments for the patient interface assembly of the present invention, the pads that attach to the chin support assemblies and that contact the surface of the patient were discussed briefly. It is to be understood that the present invention contemplates attaching any conventional pad to the present forehead support assemblies and the chin support assemblies. For example, various types of patient contacting pads that are suitable for use with the present invention are described in U.S. provisional patent application Ser. No. 10/884,060, (Publication no. US 2005-0011522 A1), the contents of which are incorporated herein by reference. Those skilled in the art will understand, however, that other pads, and materials for the pad (such as gels, foams, silicon, and fabric) can be used in conjunction with the patient interface device of the present invention.

It can also be appreciated that the description of the present invention, while discussing some different embodiments for the cushion and mask, is not intended to be an exhaustive listing of the seals and masks suitable for use with the patient interface device of the present invention. On the contrary, those skilled in the art can appreciate that the mask shell can have almost any configuration or size and still be used in conjunction with the patient interface device of the present invention. Likewise, the cushion can comprise multiple cushions or flaps and can have almost any configuration and size so long as it provides a sealed contact between the patient interface and the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface assembly comprising:
   a substantially rigid support having a first end and a second end opposite the first end;
   a patient interface device coupled to the first end of the support;
   a first arm coupled to a first side of the support;
   a second arm coupled to a second side of the support;
   a generally U-shaped cross member having a first end coupled to the first arm and a second end coupled to the second arm and spanning between the first arm and the second arm, the generally U-shaped cross member having a central portion located midway between the first and second ends of the generally U-shaped cross member, wherein a first side of the second end of the substantially rigid support is coupled to the central portion of the U-shaped cross member such that a longitudinal axis of the substantially rigid support is aligned with a centerline of the patient responsive to the patient interface assembly being worn by the patient, wherein a coupling port having an exterior side and an interior side opposite the exterior side is provided at a second side of the second end of the substantially rigid support opposite the first side of the second end of the substantially rigid support, wherein the exterior side of the coupling port is structured to be coupled to a patient circuit; and
   a flexible conduit provided within the substantially rigid support having a first end coupled to the interior side of the coupling port and a second end coupled to the patient interface device, wherein the flexible conduit extends within the substantially rigid support from the first end of the substantially rigid support to the second end of the substantially rigid support and from the interior side of the coupling port to the patient interface device.

2. The patient interface assembly of claim 1, further comprising a headgear assembly operatively coupled to the U-shaped cross member and adapted to overlie a portion of a patient's head responsive to the patient interface assembly being donned by such a patient.

3. The patient interface assembly of claim 1, wherein the cross member is flexible, rigid, or semi-rigid.

4. The patient interface assembly of claim 1, wherein the patient interface device is a nares element or a nasal cushion.

5. The patient interface assembly of claim 1, wherein the patient interface device is selectively detachable from the support.

6. The patient interface assembly of claim 1, further comprising a headgear attachment element disposed on the first arm and the second arm.

7. The patient interface assembly of claim 1, further comprising an exhaust assembly associated with the support.

* * * * *